(12) United States Patent
Dietz et al.

(10) Patent No.: US 9,114,245 B2
(45) Date of Patent: Aug. 25, 2015

(54) ULTRASONIC SURGICAL APPARATUS AND METHODS FOR USE THEREOF

(75) Inventors: Timothy G. Dietz, Terrace Park, OH (US); Foster B. Stulen, Mason, OH (US); William A. Olson, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 991 days.

(21) Appl. No.: 12/857,373

(22) Filed: Aug. 16, 2010

(65) Prior Publication Data

US 2011/0040212 A1 Feb. 17, 2011

Related U.S. Application Data

(60) Provisional application No. 61/233,945, filed on Aug. 14, 2009.

(51) Int. Cl.
*A61N 7/00* (2006.01)
*B06B 3/00* (2006.01)
(Continued)

(52) U.S. Cl.
CPC .......... *A61N 7/00* (2013.01); *A61B 17/320068* (2013.01); *B06B 3/00* (2013.01);
(Continued)

(58) Field of Classification Search
CPC .............. A61B 17/320068; A61B 2017/2253; A61B 2017/306; A61N 7/00; A61N 2007/0078; A61N 2007/082; A61N 2007/0034; B03B 3/00
See application file for complete search history.

(56) References Cited

U.S. PATENT DOCUMENTS

| | | |
|---|---|---|
| 3,526,219 A | 9/1970 | Balamuth |
| 3,589,363 A | 6/1971 | Banko et al. |

(Continued)

FOREIGN PATENT DOCUMENTS

| | | |
|---|---|---|
| FR | 2926731 | 7/2009 |
| JP | 07-024311 | 5/1995 |

(Continued)

OTHER PUBLICATIONS

PCT, Written Opinion of the International Preliminary Examining Authority, International Application No. PCT/US2010/045622 (Oct. 28, 2011).

(Continued)

*Primary Examiner* — Long V Le
*Assistant Examiner* — Angela M Hoffa

(57) ABSTRACT

Ultrasound surgical apparatus are disclosed, including: medical ultrasound handpieces with proximally mounted ultrasound radiators configured to create a distally-focused beam of ultrasound energy, in combination with distal guide members for control of focal point depth; medical ultrasound handpieces with proximally mounted ultrasound radiators configured to create a distally-focused beam of ultrasound energy, in combination with distal rolling members for manipulability and control of focal point depth; medical ultrasound handpiece assemblies with coupled end effectors providing a probe with a probe dilation region configured to have an average outside diameter that is equal to or greater than the average outside diameter of a probe tip and neck; as well as junctions to an ultrasonically inactive probe sheath; medical ultrasound handpiece assemblies with coupled end effectors having positionable, ultrasonically inactive probe sheath ends slidably operable to both cover and expose at least a probe tip; and ultrasound transducer cores including a transducing structure affixed to a longitudinally elongated, generally planar, single crystal or polycrystalline material waveguide.

10 Claims, 39 Drawing Sheets

(51) Int. Cl.
    *A61B 17/32*         (2006.01)
    *A61B 17/225*       (2006.01)
    *A61B 17/30*         (2006.01)

(52) U.S. Cl.
    CPC ... *A61B2017/2253* (2013.01); *A61B 2017/306* (2013.01); *A61N 2007/0034* (2013.01); *A61N 2007/0078* (2013.01); *A61N 2007/0082* (2013.01)

(56) References Cited

U.S. PATENT DOCUMENTS

| | | | |
|---|---|---|---|
| 3,990,452 A | | 11/1976 | Murry et al. |
| 4,428,748 A | | 1/1984 | Peyman et al. |
| 4,750,902 A | | 6/1988 | Wuchinich et al. |
| 5,084,012 A | | 1/1992 | Kelman |
| 5,322,055 A | | 6/1994 | Davison et al. |
| 5,569,968 A | | 10/1996 | Lal et al. |
| 5,595,328 A | * | 1/1997 | Safabakhsh et al. ........... 228/1.1 |
| 5,683,592 A | | 11/1997 | Bartholomew et al. |
| 5,728,089 A | | 3/1998 | Lal et al. |
| 5,911,699 A | * | 6/1999 | Anis et al. ........................ 604/22 |
| 5,954,736 A | | 9/1999 | Bishop et al. |
| 5,984,904 A | * | 11/1999 | Steen et al. .................... 604/264 |
| 6,036,661 A | | 3/2000 | Schwarze et al. |
| 6,082,180 A | | 7/2000 | Greenwood |
| 6,278,218 B1 | | 8/2001 | Madan et al. |
| 6,283,981 B1 | | 9/2001 | Beaupre |
| 6,309,400 B2 | | 10/2001 | Beaupre |
| 6,325,811 B1 | | 12/2001 | Messerly |
| 6,423,082 B1 | | 7/2002 | Houser et al. |
| 6,440,121 B1 | | 8/2002 | Weber et al. |
| 6,638,249 B1 | | 10/2003 | Lal et al. |
| 6,666,825 B2 | | 12/2003 | Smith et al. |
| 6,699,237 B2 | * | 3/2004 | Weber et al. ....................... 606/2 |
| 6,740,058 B2 | | 5/2004 | Lal et al. |
| 6,869,420 B2 | | 3/2005 | Lal et al. |
| 6,923,790 B2 | | 8/2005 | Lal et al. |
| 6,939,317 B2 | | 9/2005 | Zacharias |
| 7,105,103 B2 | | 9/2006 | Keenan et al. |
| 7,285,096 B2 | * | 10/2007 | Burba et al. .................. 600/459 |
| 7,387,742 B2 | | 6/2008 | Daskal et al. |
| 7,396,484 B2 | | 7/2008 | Daskal et al. |
| 8,334,635 B2 | * | 12/2012 | Voegele et al. .......... 310/323.12 |
| 8,348,967 B2 | * | 1/2013 | Stulen ............................ 606/169 |
| 8,372,102 B2 | * | 2/2013 | Stulen et al. ................... 606/169 |
| 8,394,115 B2 | * | 3/2013 | Houser et al. ................. 606/169 |
| 8,430,898 B2 | * | 4/2013 | Wiener et al. ................. 606/169 |
| 8,882,792 B2 | * | 11/2014 | Dietz et al. .................... 606/169 |
| 2001/0016804 A1 | * | 8/2001 | Cunningham et al. ............ 703/7 |
| 2001/0025190 A1 | * | 9/2001 | Weber et al. ..................... 607/89 |
| 2002/0077550 A1 | | 6/2002 | Rabiner et al. |
| 2002/0091404 A1 | | 7/2002 | Beaupre |
| 2002/0179162 A1 | | 12/2002 | Lal et al. |
| 2002/0193817 A1 | | 12/2002 | Lal et al. |
| 2003/0195468 A1 | | 10/2003 | Lal et al. |
| 2003/0199165 A1 | | 10/2003 | Keenan et al. |
| 2004/0054364 A1 | | 3/2004 | Aranyi et al. |
| 2005/0101869 A1 | * | 5/2005 | Burba et al. .................. 600/459 |
| 2005/0188548 A1 | | 9/2005 | Daskal et al. |
| 2005/0266680 A1 | | 12/2005 | Daskal et al. |
| 2006/0015130 A1 | * | 1/2006 | Voorhees et al. ............. 606/190 |
| 2006/0090956 A1 | | 5/2006 | Peshkovskiy et al. |
| 2006/0235306 A1 | * | 10/2006 | Cotter et al. .................. 600/459 |
| 2007/0016040 A1 | | 1/2007 | Nita |
| 2007/0118170 A1 | * | 5/2007 | Kieturakis et al. ............. 606/192 |
| 2007/0239028 A1 | * | 10/2007 | Houser et al. ................. 600/471 |
| 2007/0260172 A1 | * | 11/2007 | Nita ................................ 604/22 |
| 2008/0027328 A1 | | 1/2008 | Klopotek et al. |
| 2008/0194999 A1 | * | 8/2008 | Yamaha et al. .................... 601/2 |
| 2008/0202550 A1 | * | 8/2008 | McDermott et al. ............. 134/1 |
| 2008/0214967 A1 | | 9/2008 | Aranyi et al. |
| 2008/0234710 A1 | | 9/2008 | Neurohr et al. |
| 2008/0234711 A1 | | 9/2008 | Houser et al. |
| 2008/0243162 A1 | * | 10/2008 | Shibata et al. ................ 606/185 |
| 2008/0300611 A1 | * | 12/2008 | Houser et al. ................. 606/167 |
| 2009/0018471 A1 | * | 1/2009 | Dorawa et al. .................... 601/2 |
| 2009/0030311 A1 | * | 1/2009 | Stulen et al. .................. 600/439 |
| 2009/0030438 A1 | | 1/2009 | Stulen |
| 2009/0036914 A1 | * | 2/2009 | Houser ........................ 606/169 |
| 2009/0069830 A1 | | 3/2009 | Mulvihill et al. |
| 2009/0143795 A1 | | 6/2009 | Robertson |
| 2011/0040213 A1 | * | 2/2011 | Dietz et al. ........................ 601/2 |
| 2011/0082486 A1 | * | 4/2011 | Messerly et al. .............. 606/169 |
| 2011/0087213 A1 | * | 4/2011 | Messerly et al. ................ 606/34 |
| 2011/0087216 A1 | * | 4/2011 | Aldridge et al. ................. 606/34 |
| 2011/0087256 A1 | * | 4/2011 | Wiener et al. ................. 606/169 |
| 2011/0196404 A1 | * | 8/2011 | Dietz et al. .................... 606/169 |
| 2012/0022525 A1 | * | 1/2012 | Dietz et al. ...................... 606/45 |
| 2012/0022526 A1 | * | 1/2012 | Aldridge et al. ................. 606/45 |
| 2012/0078244 A1 | * | 3/2012 | Worrell et al. ................... 606/33 |
| 2012/0116261 A1 | * | 5/2012 | Mumaw et al. .................... 601/2 |
| 2012/0116263 A1 | * | 5/2012 | Houser et al. ...................... 601/2 |
| 2012/0116364 A1 | * | 5/2012 | Houser et al. ..................... 606/1 |
| 2012/0116366 A1 | * | 5/2012 | Houser et al. ..................... 606/1 |
| 2012/0116367 A1 | * | 5/2012 | Houser et al. ..................... 606/1 |
| 2012/0116379 A1 | * | 5/2012 | Yates et al. ....................... 606/33 |
| 2012/0116391 A1 | * | 5/2012 | Houser et al. .................... 606/41 |
| 2012/0269676 A1 | * | 10/2012 | Houser et al. ..................... 422/1 |
| 2012/0289984 A1 | * | 11/2012 | Houser et al. ................. 606/169 |
| 2012/0310262 A1 | * | 12/2012 | Messerly et al. .............. 606/169 |
| 2012/0310263 A1 | * | 12/2012 | Messerly et al. .............. 606/169 |
| 2012/0310264 A1 | * | 12/2012 | Messerly et al. .............. 606/169 |
| 2013/0023875 A1 | * | 1/2013 | Harris et al. ..................... 606/47 |
| 2013/0053831 A1 | * | 2/2013 | Johnson et al. .................. 606/1 |
| 2013/0090576 A1 | * | 4/2013 | Stulen et al. ....................... 601/2 |

FOREIGN PATENT DOCUMENTS

| | | |
|---|---|---|
| JP | 08-084740 | 4/1996 |
| JP | 2006-034651 | 2/2006 |
| JP | 2007-175509 | 7/2007 |
| JP | 2009-266916 | 11/2009 |
| WO | 98/38927 | 9/1998 |
| WO | 02/09812 | 2/2002 |
| WO | 02/081025 | 10/2002 |
| WO | 03/030754 | 4/2003 |
| WO | 2006/082573 | 8/2006 |
| WO | 2007/140331 | 12/2007 |

OTHER PUBLICATIONS

PCT, Invitation to Pay Additional Fees and Partial International Search Report, International Application No. PCT/US2010/045622 (Oct. 22, 2010).

Lal, A., Micromachined Silicon Ultrasonic Longitudinal Mode Actuators: Theory and Applications to Surgery, Pumping, and Atomization (254 pages) (1996).

Brünahl, J., "Physics of Piezoelectric Shear Mode Inkjet Actuators" (109 pages) (2003).

Lee, J.E-Y. et al., "A Single-Crystal-Silicon Bulk-Acoustic-Mode Microresonator Oscillator," *IEEE Electron Device Letters*, vol. 29, No. 7, pp. 701-703 (Jul. 2008).

Product information entitled, "Designing with Piezoelectric Transducers: Nanopositioning Fundamentals," by Physik Instrumente (PI) GmbH & Co. (49 pages) (Sep. 2005).

Uchino, K., "Introduction to Micromechatronics," Report prepared on behalf of the International Center for Actuators and Transducers (122 pages) (Jun. 2003).

Zakel, E. et al., Process Makes Electroless Nickel/Gold Wafer Bumping Economical for Flip-Chip Packaging (6 pages) (2003).

Chidambaram, P.R. et al., "Fundamentals of Silicon Material Properties for Successful Exploitation of Strain Engineering in Modern CMOS Manufacturing," *IEEE Transactions on Electron Devices*, vol. 53, No. 5, pp. 944-964 (May 2006).

Weichel, S. et al., "Silicon-to-silicon wafer bonding using evaporated glass," *Sensors and Actuators*, A 70, pp. 179-184 (1998).

Sergent, J.E., "Chapter 8: Materials and Processes for Hybrid Microelectronics and Multichip Modules," *Electronic Materials and Processing Handbook, Third Edition*, pp. 8.1-8.103 (2004).

(56) References Cited

OTHER PUBLICATIONS

Hwang, J.S, "Chapter 5: Solder Technologies for Electronic Packaging and Assembly," *Electronic Materials and Processing Handbook, Third Edition*, pp. 5.1-5.109 (2004).

Lassner, E. et al., "Chapter 6: Tungsten Alloys," *Tungsten Properties, Chemistry, Technology of the Element, Alloys and Chemical Compounds*, pp. 255-282 (1999).

PCT, International Search Report, International Application No. PCT/US2010/045622 (Jan. 31, 2011).

CN, Notification of the First Office Action (English translation), Chinese Application No. 201080046527.8, dated Aug. 30, 2013.

EP, Search Report and Search Opinion, European Application No. 14166440.9, dated Sep. 30, 2014.

JP, Notification of Reasons for Refusal (English translation), Japanese Application No. 2012-524932, dated Apr. 15, 2014.

PCT, International Search Report and Written Opinion, International Application No. PCT/US2014/010899, dated Oct. 9, 2014.

\* cited by examiner

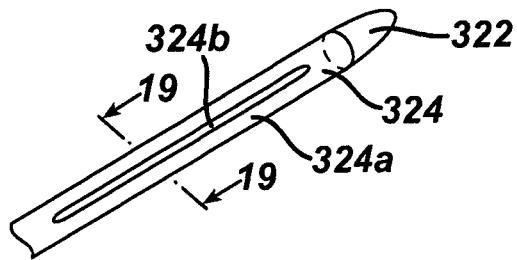
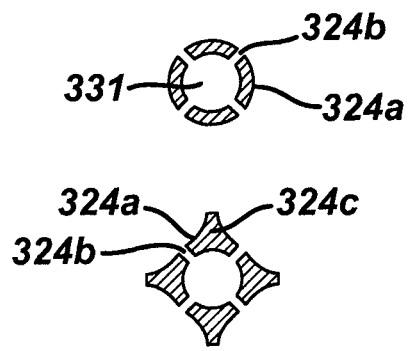
FIG. 18
FIG. 19
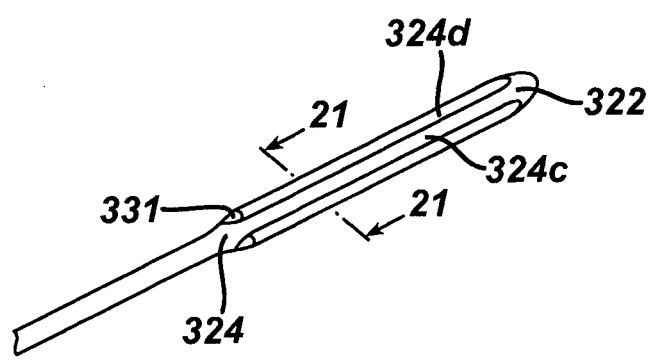
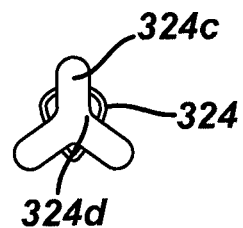
FIG. 20
FIG. 21

ULTRASONIC SURGICAL APPARATUS AND METHODS FOR USE THEREOF

CROSS-REFERENCE TO RELATED APPLICATIONS

This application claims the benefit of U.S. Provisional Application No. 61/233,945, filed on Aug. 14, 2009, the entire contents of which are incorporated herein by reference.

FIELD

The various embodiments relate to an ultrasonic surgical apparatus and, more particularly, to ultrasonic surgical instruments and methods for shear-thinning dermal fillers.

BACKGROUND

Human skin is composed of two major layers, the epidermis and the dermis. Below these layers lies the hypodermis, which is not usually classified as a layer of skin. The thinner outer layer of the skin, the epidermis, provides a barrier to the external environment. The epidermis is typically about 0.05 to 1.5 mm thick (varying from its minimum at the eyelids to its maximum over the palms and soles of the feet). It is composed of many different cell types including keratinocytes, melanocytes, and langerhan cells. Keratinocytes are the major cell type (being about 75 to 80% of the total number of cells), and are responsible for keeping water in the body and keeping other harmful chemicals and pathogens out. The epidermis is made up of a stratified squamous epithelium with an underlying basement membrane. It contains no blood vessels, and is nourished by diffusion from the dermis.

The thicker inner layer of the skin, the dermis, is the major component of human skin. The dermis, or corium, is typically about 0.3 to 5 mm thick (varying from its minimum at the eyelids to its maximum over the back). It is composed of a network of connective tissue, which provides strength, elasticity, and thickness to the skin, and contains other structures including capillaries, nerve endings, hair follicles, smooth muscle, glands, and lymphatic tissue. The main cell type of the dermis is the fibroblast, which is responsible for the synthesis and secretion of dermal matrix components such as collagen, elastin, and glycosaminoglycans. Collagen provides the strength, elastin the elasticity, and glycosaminoglycans the moistness and plumpness of the skin. With ageing, the thickness of the dermal layer is reduced, and this is believed to be partially responsible for the formation of wrinkles in ageing skin.

The hypodermis, also commonly referred to as the subcutaneous fat layer or subcutaneous tissue, lies below the dermis. Its purpose is to attach the skin to underlying bone and muscle as well as to supply the dermis with blood vessels and nerves. It is made up of loose connective tissue and elastin. The main cell types are fibroblasts, macrophages, and adipocytes. The hypodermis contains about 50% of total body fat, the fat serving as padding, insulation, and an energy reserve for the body.

Facial aging occurs as the result of several factors: inherent changes within the skin, the effects of gravity, the effects of facial muscles acting on the skin (dynamic lines), soft tissue loss or shift, bone loss, and a gradual loss of tissue elasticity. The epidermis begins to thin, causing the junction with the dermis to flatten. Collagen also decreases, and bundles of collagen, which give the skin turgor, become looser and lose strength. When the skin loses elasticity it is less able to resist stretching. The skin begins to wrinkle as a result of gravity, muscle pull, and tissue changes. Water loss and a breakdown of the connective bonds between cells also weakens the barrier function of the skin, which can cause the skin's pore size to increase.

As a person ages, the face loses volume, soft tissue, and fat. The appearance of jowls and folds is usually caused by the drooping of facial tissues and the folding of skin over areas where it is attached to and supported by the muscles below. Due to the reduction in soft tissue, the face appears more hollow. In various facial areas such as the forehead, eyes, nose, midface, and lower face, changes relating to aging have been well documented. For example, in the forehead area, the forehead and brow droop over time, which lowers the eyebrows and causes the upper eyelid skin to bunch. Forehead lines appear when one tries to hold the brows and eyelids up to counteract these changes. It is well known that the eye area is often the first facial feature to show signs of aging. Skin changes around the eyes occur earlier than in the rest of the face since the skin is thinnest here. The skin in this area also contains fewer glands and is subjected to constant blinking, squinting, rubbing, and pulling.

The midface area ages when the cheeks begin to droop, causing nasolabial folds, which are the lines that run from the sides of the nose to the corners of the mouth. It is known to treat these folds with facial fillers. In the nose area, the nose appears to elongate. Common causes of elongation are thinning of the soft tissue and loss of elasticity, which causes "drooping of the tip" and unmasking of the bone, creating a new hump.

In the lower face area, facial tissues descend, causing so-called "laugh lines". It is known to treat these folds and lines with facial fillers. Further down on the lower face, the corners of the mouth may droop, and a descent of the jowls can create folds often referred to as "marionette lines." Furthermore, jowls form when the cheeks sag around a fixed point along the jaw where the facial muscles attach to the jawbone.

Various injectables have been used for restoring tissue loss in the face. Since the 1980s, injectable collagen has been used as a soft-tissue filler to fill wrinkles, lines, and scars on the face. Collagen is a naturally occurring protein that supports various parts of the body including skin, tendons, and ligaments. Fat injections have also been used to add volume, fill wrinkles and lines, and enhance the lips. Fat injections involve taking fat from one part of a patient's body (typically the abdomen, thighs, or buttocks) and reinjecting it beneath the facial skin. Botulinum toxins, which were first approved for the treatment of neck spasms, cranial nerve disorders, and eye spasms, have also been used "off-label" for cosmetic purposes. With the recent FDA approval of Botox for cosmetic use in the glabellar region, the drug is becoming widely used for the temporary treatment of dynamic lines. In contrast to fillers, the botulinum toxin is injected into facial muscles, temporarily blocking nerve impulses and relaxing the muscles to smooth so-called "worry lines."

Hyaluronic acid is one of most commonly used cosmetic dermal fillers. Hyaluronic acid is a linear polysaccharide that exists naturally in all living organisms, and is a universal component of the extra-cellular spaces of body tissues. The identical structure of hyaluronic acid in all species and tissues makes this polysaccharide an ideal substance for use as a bio-material in health and medicine. Hyaluronic acid is present in many places in the human body. It gives volume to the skin, shape to the eyes, and elasticity to the joints. The highest concentrations of hyaluronic acid are found in connective tissues, and most of the hyaluronic acid produced by the human body (about 56%) is found in the skin.

Various forms of hyaluronic acid are provided commercially by a number of manufacturers. The most commonly used hyaluronic acid is a non-animal stabilized hyaluronic acid (NASHA), distributed in a clear gel form and produced by bacterial fermentation using streptococci bacteria. Different from animal derived hyaluronic acid, the non-animal derived hyaluronic acid is free from animal proteins. This limits the risk of animal-based disease transmission or the development of an allergic response. The most known non-animal stabilized hyaluronic acid is manufactured by Q-med AB of Seminariegatan, Uppsala, Sweden and commercially available under the tradename Restylane®. Since its commercialization in 1996, it is estimated that over 2,500,000 treatments have been carried out worldwide. Other non-animal stabilized hyaluronic acid products include Perlane® from Q-med, which has larger particles than Restylane®, and Captique™ from Genzyme Corporation. Another commonly used filler is hyaluronic acid derivative manufactured by Genzyme Corporation and commercially available under the tradename Hylaform Plus. Hylaform Plus is a sterile, nonpyrogenic, viscoelastic, clear, colorless, transparent gel implant composed of cross-linked molecules of hyaluronan. Although hyaluronic acid and its derivatives are the most commonly used dermal fillers, they have limited long-term viability. The material must be reinjected periodically, typically every 4 to 12 months, due to hyaluronan metabolism in the body.

To increase the longevity of dermal fillers, high molecular weight formulations are being developed. However, increasing molecular weights result in higher and higher viscosities. The higher the viscosity, the more difficult it is to inject the desired amount of dermal filler into the desired location, or to extract any excess. In addition, because the dermal filler must be injected within the existing skin layers, and there is minimal ability to create a pocket for the filler to reside in, it is difficult to manipulate high molecular weight fillers within existing skin tissue to achieve the desired cosmetic effect. Also, once injected, high molecular weight dermal fillers may shift to a different location and create an undesirable cosmetic defect. Current methods which seek to use a lysing agent to remove excess or unwanted filler do not provide much differential action with respect to native tissue, causing damage to adjacent tissues and substantially increasing the risk of a poor aesthetic outcome.

Ultrasonic energy can be used to shear-thin highly viscous materials, and the applicants have found that ultrasonic energy can successfully be used to shear-thin collagen-based dermal fillers. The energy can be applied via direct contact ultrasound (at frequencies of 20-200 kHz) or via high intensity, focused, field effect ultrasound or "HIFU" (at frequencies of 50 kHz-20 MHz). Since a non-thermal shearing action will be desired from the HIFU source, the frequencies of interest will dip below the traditional lower frequency limit of high frequency medical ultrasound, 500 kHz, to at least 100 kHz. The lower frequency limit will typically defined by the desired resolution of the focal point for treatment. Ultrasonic energy can also be used to undermine or dissect tissue, to release folds, or to create pockets within tissue.

The requirements and construction of devices for delivering contact ultrasound and HIFU will be different. Contact devices must come into direct contact with a filler in order for an ultrasonic element to shear-thin the filler material. HIFU devices, on the other hand, focus field effect ultrasound so as to sheer thin the filler material without direct contact between the ultrasound radiator and the filler. However, readily known devices are deficient in that contact devices are generally designed for the macroscopic coagulation or ablation of tissue surfaces, while HIFU devices are generally designed for the image-guided hyperthermic, coagulative, or cavitation-induced destruction of tissue at depth. Accordingly, improved ultrasonic apparatuses that are safe and effective for non-thermal, shallow depth dermatological treatments are required. In addition, methods for manipulating high molecular weight, high viscosity dermal fillers and shallow facial tissues are desired.

SUMMARY

A first embodiment of an ultrasonic surgical apparatus includes a medical ultrasound handpiece having a distal end and an ultrasound radiator mounted proximally from the distal end. The ultrasound radiator is configured to create a beam of ultrasound energy having a focal point at a predetermined distance from the ultrasound radiator in the direction of the distal end, and has at least one monolithic ultrasound source with a focused emitting surface or at least one array ultrasound source configured as an electronically focusable array. The first embodiment also includes a guide member for placement around a facial feature, whereupon the ultrasound handpiece is slidably engaged with the guide member to position the focal point within the skin.

A method of using the device of the first embodiment includes the steps of: injecting a dermal filler into the dermis of a facial feature; placing the distal guide member of the first embodiment on the surface of the skin so as to surround the facial feature; applying an acoustic gel to the skin over the facial feature; engaging the distal end of the ultrasound handpiece of the first embodiment with the emplaced guide member; and slidably translating the ultrasound handpiece upon the emplaced guide member to position the focal point of the ultrasound radiator within the injected dermal filler, then subsequently powering the ultrasound radiator to shear-thin the dermal filler.

A second embodiment of an ultrasonic surgical apparatus includes a medical ultrasound handpiece having a distal end, a distal rolling member for placement over a facial feature, and a ultrasound radiator mounted proximally from the distal end. The ultrasound radiator is configured to create a beam of ultrasound energy having a focal point at a predetermined distance from the ultrasound radiator in the direction of the distal end, and has at least one monolithic ultrasound source with a focused emitting surface or at least one array ultrasound source configured as an electronically focusable array. In certain expressions of the embodiment, the distal rolling member is externally coupled to the ultrasound radiator through an acoustic coupling medium generally contained within the medical ultrasound handpiece. In other expressions of the embodiment, the distal rolling member is internally coupled to the focusing ultrasound radiator, which is contained within the distal rolling member.

A method of using the device of the second embodiment includes the steps of: injecting a dermal filler into the dermis of the facial feature; placing the distal rolling member of the device of the second embodiment on the surface of the skin over the facial feature; applying an acoustic gel to the skin over the facial feature; and rollingly translating the distal rolling member over the skin to position the focal point of the focusing ultrasound radiator within the injected dermal filler, then subsequently powering the ultrasound radiator to shear-thin the dermal filler.

A third embodiment of an ultrasonic surgical apparatus includes a medical ultrasound handpiece assembly having an ultrasound transducer and an end effector coupled to the ultrasound transducer. The end effector has, in order, a distal probe tip, a probe neck, a probe dilation region, and ultrasonically active shaft, with the shaft being coaxially held within an ultrasonically inactive probe sheath. The probe dilation region is configured to have an average outside diameter that is equal to or greater than the average outside diameter of the probe tip and the average outside diameter of the probe neck. The probe sheath is configured to have an outside diameter that is approximately equal to the outside diameter of the probe dilation region so as to create a uniform junction between the probe sheath and the probe dilation region. In certain expressions of the embodiment, the junction may be tight between the probe sheath and the probe dilation region. In other expressions of the embodiment, the junction may be loose but self-cleaning.

A method of using the device of the third embodiment includes the steps of: injecting a dermal filler into a facial feature; inserting at least the distal probe tip of the device of the third embodiment beneath the surface of the skin and into the injected dermal filler; powering the ultrasound transducer to operate the probe tip; and inserting at least the distal probe tip into the injected dermal filler. A preferred method further includes the step, following the powering step, of inserting the probe dilation region beneath the surface of the skin to protect the surface of the skin from unintended contact with ultrasonically active portions of the probe.

A fourth embodiment of an ultrasound surgical apparatus includes a medical ultrasound handpiece assembly having an ultrasound transducer and an end effector coupled to the ultrasound transducer. The end effector has, in order, a distal probe tip, a probe neck, and an ultrasonically active shaft, with the shaft coaxially being held within an ultrasonically inactive probe sheath. The probe sheath is configured such that the distal end of the probe sheath is slidably operable to both cover and expose at least the probe tip. In certain expressions of the embodiment, the distal end of the probe sheath is configured to slidably retract when the probe sheath experiences a certain longitudinal resistance. In other expressions of the embodiment, the proximal end of the probe sheath is coupled to an adjustment mechanism for slidably retracting and extending the distal end of the probe sheath.

A method of using the device of the fourth embodiment includes the steps of: inserting at least the distal probe tip of the device of the fourth embodiment beneath the surface of the skin; powering the ultrasound transducer to operate the distal probe tip; inserting the distal end of the ultrasonically inactive probe sheath beneath the surface of the skin while the ultrasound transducer is powered; advancing the probe tip while the ultrasound transducer is powered; and retracting the distal end of the probe sheath to expose a greater length of the distal probe tip. A preferred method for use with devices including an adjustment mechanism further includes the step, following the insertion of the distal probe tip, of inserting the distal end of the probe sheath beneath the surface of the skin to protect the surface of the skin from unintended contact with the ultrasonically active portions of the probe. The method may be applied to injected dermal fillers and blepheroplasty.

A fifth embodiment of an ultrasonic core for an ultrasound surgical apparatus includes a transducing structure affixed to a longitudinally elongated, generally planar, single crystal or polycrystalline material waveguide. The waveguide has, in order, a first resonator or proximal end portion, a transduction portion, and a second resonator. The fifth embodiment may also include a single or polycrystalline material end effector portion monolithically or resonantly coupled to the waveguide to serve at least as an ultrasonically active shaft.

Other aspects of the disclosed ultrasonic apparatus and method for shear-thinning dermal fillers will become apparent from the following description, the accompanying drawings, and the appended claims. Several benefits and advantages are obtained from one or more of the expressions of the embodiments of the invention. In one example, the ultrasound apparatuses disclosed herein help enable the economic manipulation of high molecular weight, high viscosity dermal fillers in vivo. In another example, the ultrasound apparatuses disclosed herein provide for the ultrasonic manipulation of tissues within specific layers or at specific depths while shielding overlying tissue. In yet another example, the methods of shear-thinning dermal filler materials disclosed herein help enable the in vivo reshaping of previously injected dermal fillers. In other examples, devices and methods are used in microsurgical applications such as blepheroplasty. In general, contact and non-contact devices are disclosed which can be beneficially used to instantaneously decrease the viscosity of a dermal filler material without permanently decreasing the molecular weight of the material and/or the ability of the material to 'gel,' thereby increasing the long-term viability of injectable dermal filler treatments. Features of the devices allowing for the finely controlled application of ultrasound near or within sensitive soft tissues, such as the epidermis and dermis, are of course useful in other types of dermatological and microsurgical procedures.

BRIEF DESCRIPTION OF THE DRAWINGS

FIGS. 18 and 20 are perspective views of probe necks (including blunt distal probe tips). FIGS. 19 and 21 are cross-sectional end views of the respective probe necks.

DETAILED DESCRIPTION

Figure 1:
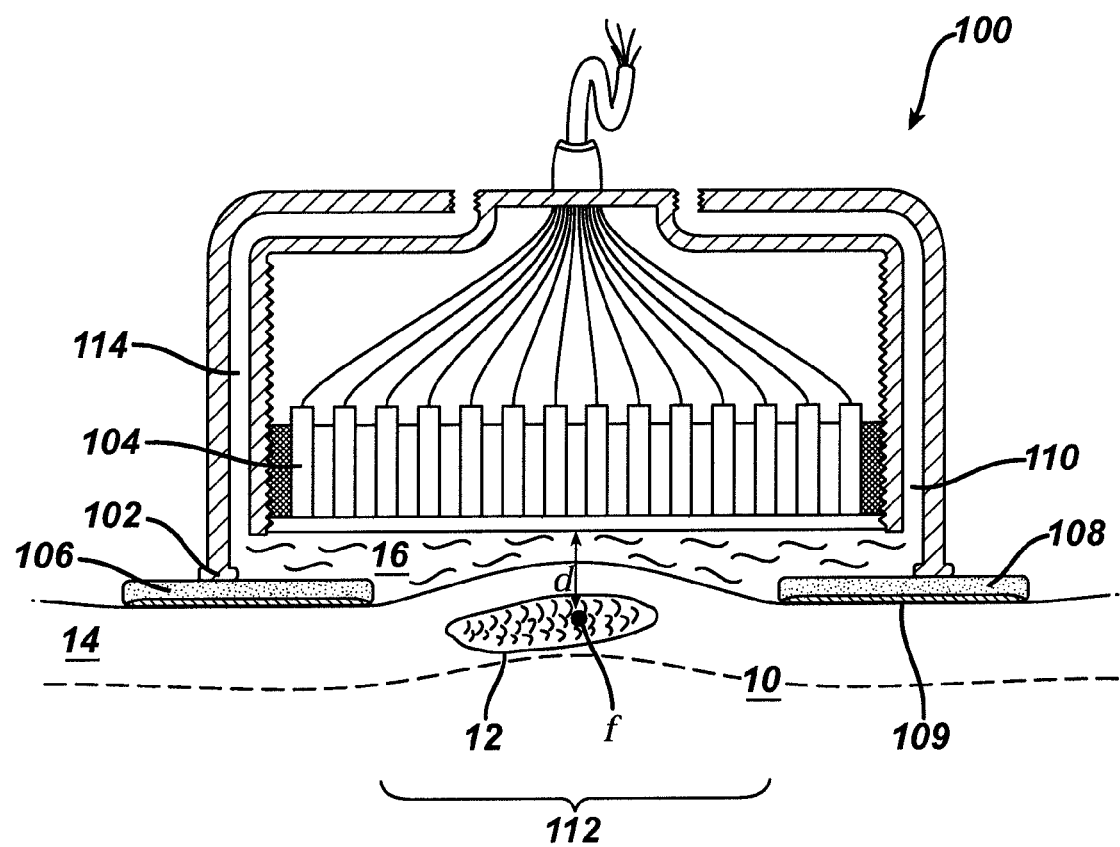
FIG. 1 is a cross-sectional side view of a medical ultrasound handpiece and guide member

Before explaining the several embodiments of the present invention in detail, it should be noted that the expressions and embodiments are not limited in their application or use to the details of construction and arrangement of parts and steps illustrated in the accompanying drawings and description. The illustrative expressions and embodiments may be implemented or incorporated in other expressions, embodiments, variations, and modifications, and may be practiced or carried out in various ways. Furthermore, unless otherwise indicated, the terms and expressions employed herein have been chosen for the purpose of describing the illustrative embodiments of the present invention for the convenience of the reader, and are not for the purpose of limiting the invention.

It is further understood that any one or more of the following-described expressions, embodiments, examples, etc. may be combined with any one or more of the other following-described expressions, embodiments, examples, etc. Such modifications and variations are intended to be included within the scope of the claims.

A first embodiment of the invention is shown in FIGS. 1-4. The first embodiment includes a medical ultrasound handpiece 100 having a distal end 102 and a focusing ultrasound radiator 104 mounted proximally from the distal end. The ultrasound radiator 104 is configured to create a beam of ultrasound energy having a focal point, f, at a predetermined distance, d, from the ultrasound radiator 104 in the direction of the distal end 102. This configuration is used to focus ultrasound energy within a facial feature 10 having a pocket of dermal filler 12 implanted in the dermis (including the dermal junctions) to cause shear-thinning of the dermal filler 12. The ultrasound radiator 104 has at least one monolithic source with a focused emitting surface, at least one array source configured as an electronically focusable array, or a combination of such ultrasound sources. Examples of array sources are disclosed in PCT Application Publication No. WO/2006/082573, the entire contents of which are incorporated herein by reference.

Figure 6:
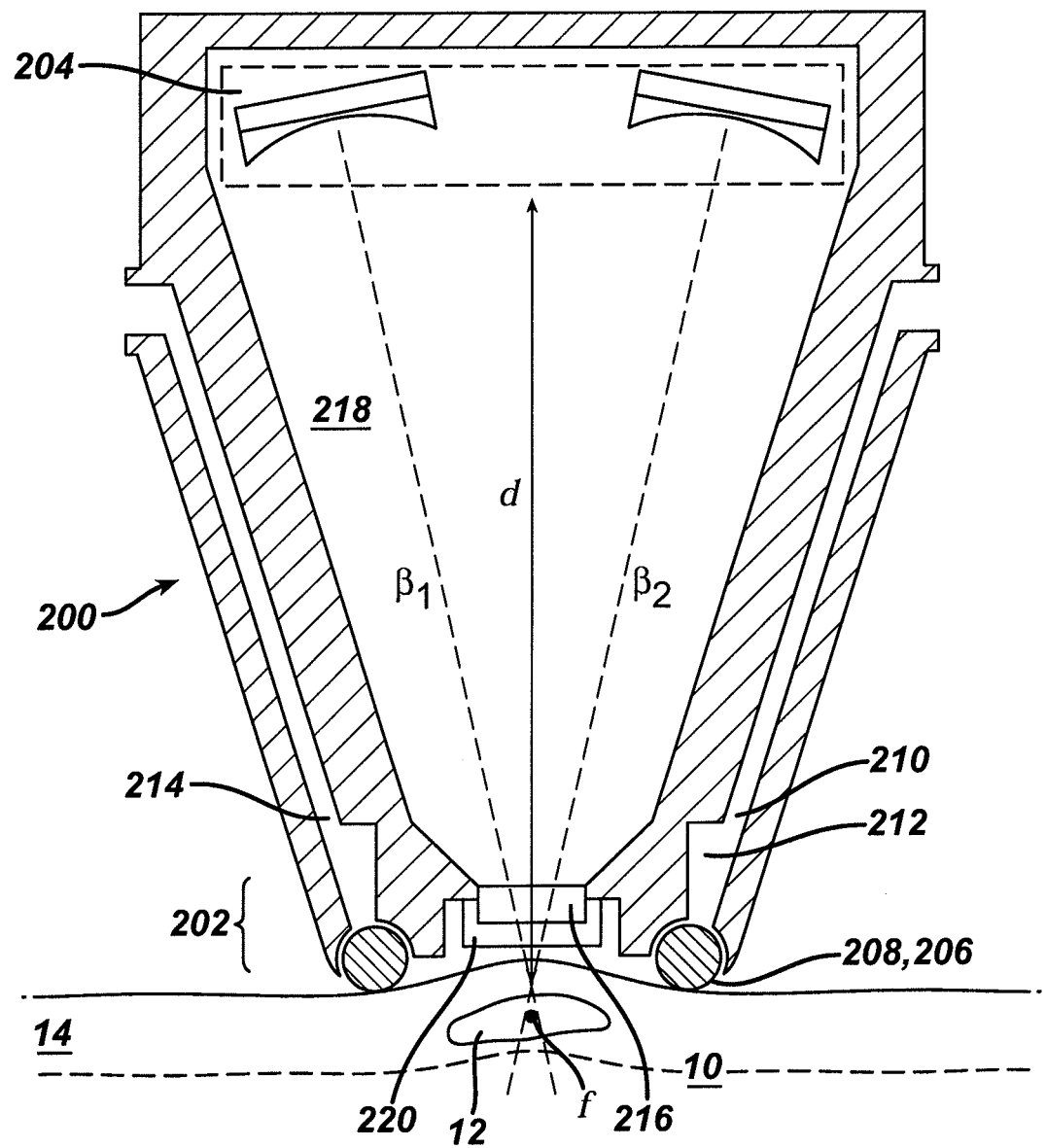

Because a focused monolithic source generates a shear which is strongest at the perimeter of the generated acoustic wave profile, additional sources may configured so that the beam axes, $B_1$ through $B_n$, of the sources generally converge upon the focal point f to enhance the ability of device to create shear proximate the focal point. A configuration of multiple ultrasound sources in a non-overlapping, convergingly focused assembly, as illustrated in FIG. 6, can enable this edge effect to be accentuated by varying the relative phases and intensities of the emitted ultrasound energy. However, this advantage is limited as a matter of practicality to devices which include a small plurality of focused monolithic sources, since a large array of transducers operated in this manner approximates the function of a single array source, i.e., multiplicity has rapidly diminishing returns in the face of increasing customization and complexity. The ultrasound radiator 104 is preferably configured to create both longitudinal and transverse acoustic waves, and should be coupled to the skin through an acoustic gel 16, which serves to improve coupling to the skin 14 and to improve the lubricity of the distal end 102 for movement over the skin 14. The use of acoustic gels and the dispensing of such gels are known in the art. See, for example, U.S. Pat. App. Publication No. 2008/0027328. The ultrasound radiator 104 should emit about 1 to 20 watts of effective power, with the heat generated thereby being dissipated or removed via thermal radiation, thermal conduction, or thermal mass or capacitance in order to prevent injury during continuous acoustic excitation. The acoustic gel 16 may be used to assist in such heat dissipation or removal.

It is important to note that if energy delivery is focused too deeply, then vital nerves and/or muscles may be damaged. However, if energy delivery is focused too shallowly, then the epidermis may be burned. The first embodiment also includes a guide member 106 for placement around the facial feature 10. The guide member 106 serves to define an area for treatment and to protect the skin 14 around that area from diffuse ultrasound energy near the focal point (or erroneous manipulation of the handpiece). The predetermined distance d may generally be adjusted electrically within an array ultrasound source, mechanically by varying the thickness of the guide member 106 (or adding additional members 106), and/or mechanically by varying the position of the focusing ultrasound radiator 104 with respect to the distal end 102 with a mechanical positioning system. However, guide member 106 may also serve to resist localized distortion of the skin 14 during application of the handpiece 100 to ensure that the predetermined distance d falls within the dermis (including the dermal junctions), as opposed to the epidermis or hypodermis, during a treatment procedure so as to minimize the need to adjust the distance d during a procedure.

In a first expression of the first embodiment, shown in FIG. 1, the distal guide member 106 may be a locating ring 108 to be positioned around the facial feature 10. In one construction, the locating ring 108 may be adhered to the surface of the skin 14 surrounding the facial feature 10 by an adhesive backing 109. In another construction, the locating ring 108 may be adhered to the surface of the skin 14 surrounding the facial feature 10 by a partial vacuum applied by a vacuum port 110 connected to a chamber 112 defined within locating ring 108 (and between the medical ultrasound handpiece 100 and the skin 14). In these or other constructions, the chamber 112 may be supplied with an acoustic gel 16 through the vacuum port 110, or through a separate fluid port 114. In one exemplary construction, the locating ring 108 is constructed from a flexible foam sheet. The foam is preferably flexible to conform to the face but essentially incompressible under typical loads (up to 5 psi) in order to maintain its shape thickness. The foam is preferably open-celled to provide a path for vacuum and to enhance acoustic protection around the periphery of the chamber 112. Locating ring 108 may define a substantially annular periphery for chamber 112, but may also or alternately be cut by the user to define the periphery of an area for treatment. The distal end 102 is slidably engaged with the locating ring 108 to position the focal point f within the skin 14.

Figure 2:
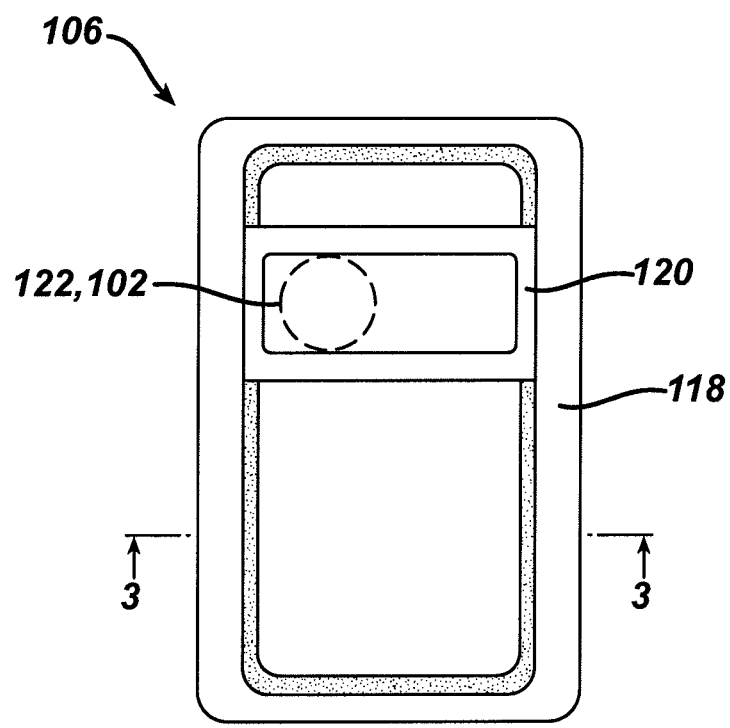
FIG. 2 is a plan view of a guide member, with a distal end of a medical ultrasound handpiece outlined in phantom lines for context.
Figure 3:
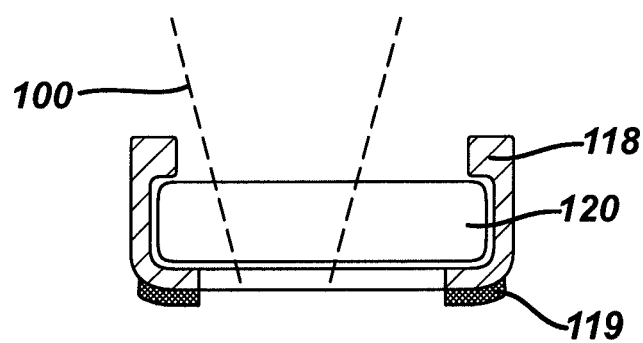
FIG. 3 is a cross-sectional side view of the guide member of FIG. 2, with a medical ultrasound handpiece outlined in phantom lines for context.
Figure 4:
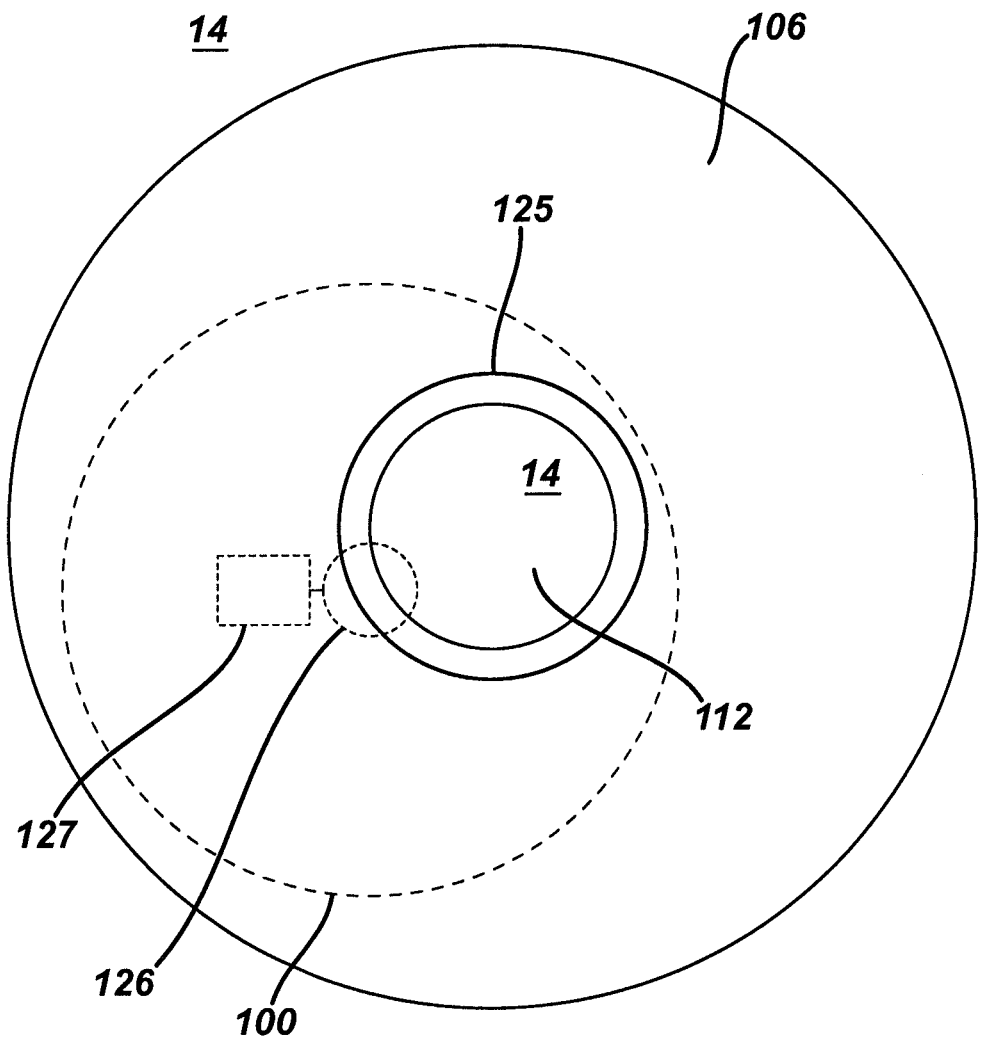
FIG. 4 is a schematic top view of a guide member with a passive wire loop.
A medical ultrasound handpiece with an active wire loop is shown in phantom lines for sake of clarity.

In a second expression of the first embodiment, shown in FIGS. 2 and 3, the distal guide member 106 may be a locating base 118 with a slidable, interlocking shuttle member 120. In one construction, the locating base 118 may be adhered to the surface of the skin 14 surrounding the facial feature 10 by an adhesive backing 119. The shuttle member 120 is configured to receive the distal end 102 of the medical ultrasound handpiece 100, which may serve as or provide a repositionable foot 122. The repositionable foot 122 may treat larger areas or long tracks by enabling the sequential treatment of a series of contiguous 'spots' within the facial feature 10. The repositionable foot 122 may be slidably repositioned within the locating base 118 by the user or under computer control. In one construction, the repositionable foot 122 may be detachable from the medical ultrasound handpiece 100. In one variation, the repositionable foot 122 may be a single use, consumable part. In another variation, the repositionable foot 122 may be a reusable, sterilizable part. In an exemplary construction, one of a plurality of repositionable feet 122 having varying thicknesses may be detachably affixed to the ultrasound handpiece 100 to mechanically vary the position of the focusing ultrasound radiator 104 with respect to the distal end 102, and thus the depth at which the predetermined distance d is found within the skin 14. In another exemplary construction, one of a plurality of repositionable feet 122 having varying areal dimensions may be detachably affixed to the ultrasound handpiece 100 to control the application of diffuse ultrasound energy near the focal point to the skin 14. The distal end 102 is slidably engaged with the locating base 118, via the shuttle 120, to position the focal point f within the skin 14.

In a third expression of the first embodiment, the medical ultrasound handpiece 100 includes a registration system 124 configured to monitor the location and/or track of the focal point f with respect to the distal guide member 106. Registration and tracking systems may include: software for tracking instrument position; electrically resonant rings, defined by a passive wire loop 125 (with a load such as a resistor and capacitor connected in series) affixed to the guide member 106 and an active wire loop 126 excited by a radio frequency element 127 mounted in the ultrasound handpiece 100, for proximity warning; magnetic coupling between the ultrasound handpiece 100 and the guide member 106, established in part by loading the guide member 106 with either a high susceptibility material or a permanent magnet material, for proximity warning; an electrical conductivity sensor (not shown), configured to detect the different electrical conductivities of the guide member 106 and the skin 14, for perimeter violation warnings; or a polarization sensor (not shown), configured to indirectly measure the differential electrical susceptibility of tissue prior to and after ultrasonic treatment, for indirectly tracking instrument position (more precisely, prior treatment positions). The guide member 106 may also be designed to have a very different electrical susceptibility so that the polarization sensor may be used for perimeter violation warnings. The delivery of ultrasound energy may be manually or automatically controlled based on the residence time of the ultrasound handpiece 100 over any particular portion of the facial feature 10 as it is moved back and forth across the surface of the skin 14 within the guide member 106. The delivery of ultrasound energy may also be automatically controlled based on measurements of skin characteristics during ultrasound treatment, such as the electrical susceptibility of pre-treatment and post-treatment tissue during the course of a procedure.

In a method of using the expressions of the first embodiment, a dermal filler 12 is injected into the dermis of the facial feature 10, and a distal guide member 106 is placed on the surface of the skin 14 so as to surround the facial feature 10. The dermal filler 12 may be injected before or after placement of the guide member 106. The medical ultrasound handpiece 100 is placed on the guide member 106, and an acoustic gel 16 is applied to the skin 14 over the facial feature 10. The acoustic gel 16 may be applied before or after placement of the ultrasound handpiece 100 on the guide member 106, depending upon the source of the gel, e.g., separate applicator or application via a handpiece port 110 or 114. The distal end 102 of the ultrasound handpiece 100 is engaged with the guide member 106, and slidably translated upon the guide member 106 to position the focal point f of the focusing ultrasound radiator 104 within the injected dermal filler 12, whereupon the ultrasound radiator 104 is powered to shear-thin the dermal filler 12. In one variation of the method, the ultrasound handpiece 100 is removed from engagement with the guide member 106 and the dermal filler 12 is manipulated from the surface of the skin 14 while in a shear-thinned state. In another variation of the method, both the ultrasound handpiece 100 and the guide member 106 are removed from the skin 14, and the dermal filler 12 is manipulated from the surface of the skin 14 while in a shear-thinned state.

In an implementation of the method, the skin 14 of the facial feature 10 is pulled into the chamber 112 defined by the distal guide member 106 by a partial vacuum. This permits more robust definition of the skin surface plane in the presence of wrinkles, and serves to accurately position the surface of the skin 14 with respect to the focusing ultrasound radiator 104 and focal point f. The focusing ultrasound radiator 104 is subsequently powered to shear-thin the injected dermal filler 12. In another implementation of the method, the skin 14 of the facial feature 10 is placed into tension, and the distal guide member is subsequently adhered onto the tensioned surface of the skin 14. This similarly improves the definition of the skin surface plane, as well as the accuracy of the positioning of the surface of the skin 14 with respect to the ultrasound radiator 104. The ultrasound radiator 104 is subsequently powered to shear-thin the injected dermal filler 12.

A second embodiment of the invention is shown in FIGS. 5-8. The second embodiment includes a medical ultrasound handpiece 200 having a distal end 202, a distal rolling member 206 for placement over a facial feature 10, and a focusing ultrasound radiator 204 mounted proximally from the distal end 202. The ultrasound radiator 204 is configured to create a beam of ultrasound energy having a focal point, f, at a predetermined distance, d, as otherwise described in the context of the first embodiment.

Figure 5:
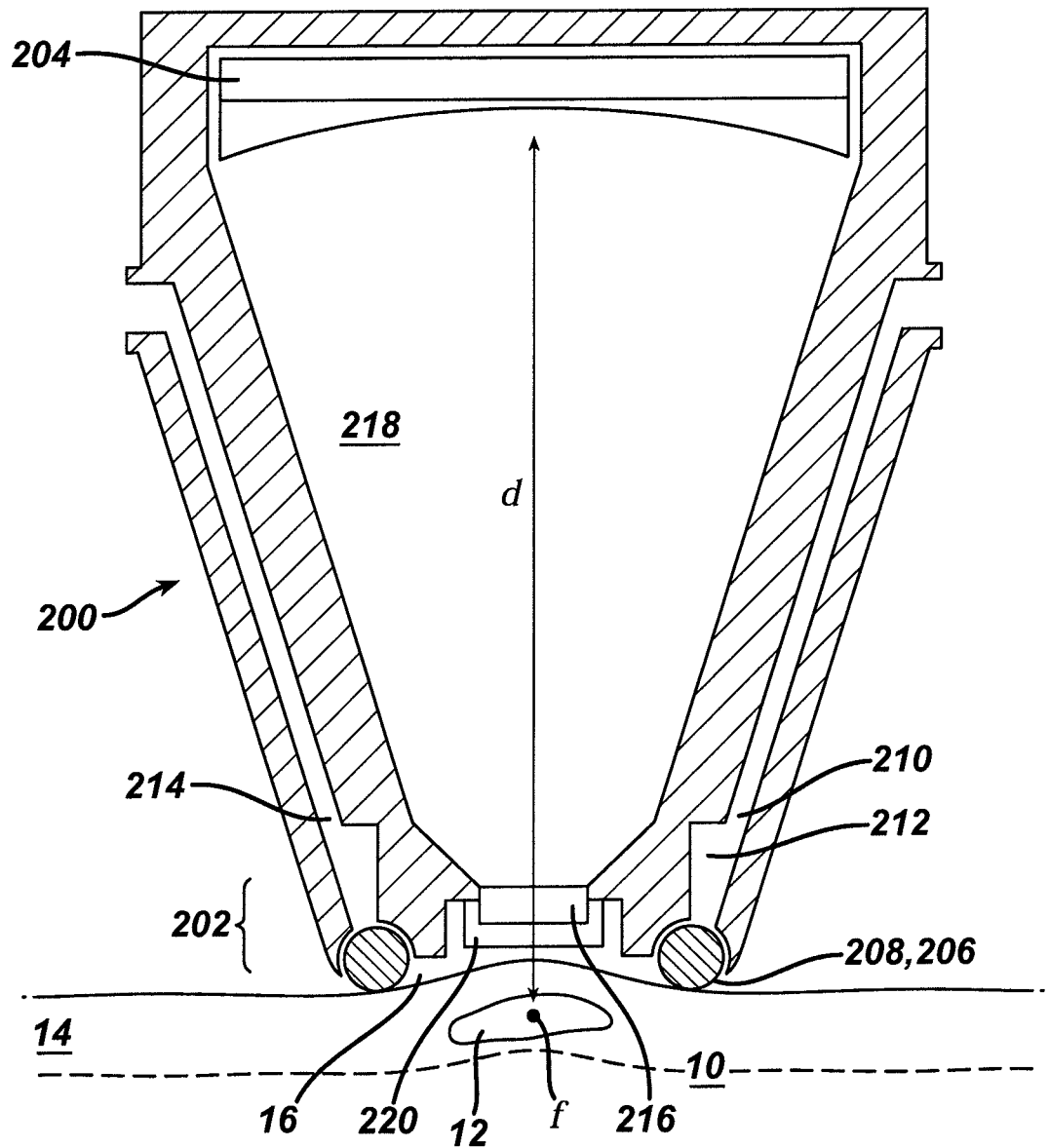
FIGS. 5 and 6 are schematic side views of medical ultrasound handpieces.

In a first expression of the second embodiment, shown in FIGS. 5 and 6, the distal rolling member 206 may be a ring of bearings 208, e.g., roller bearings or ball bearings, disposed at the distal end 202 to facilitate motion across the surface of the skin 14. The distal end 202 of the medical ultrasound handpiece 200 includes an acoustic head 216 coupled to the focusing ultrasound radiator 204 through an internal acoustic coupling medium 218 such as a fluid or gel. The acoustic head 216 is preferably constructed from polysulfone, REXOLITE® (a thermoset material produced by crosslinking polystyrene with divinylbenzene, marketed by C-LEC Plastics of Willingboro, N.J.) or "LOTEN" (marketed by Sigma Transducers of Kennewick, Wash.). Regardless of the material used, the acoustic impedance of the acoustic head 216 should be within a factor of 5 of the acoustic impedance of water, $1.5 \times 10^6$ kg/m$^2$*sec. Additional construction details intended to minimize the reflection of ultrasound energy are known within the art. See, e.g., U.S. Pat. Nos. 6,082,180 and 6,666,825. In one construction, the acoustic head 216 includes a separable interfacial boot 220 configured to shield the acoustic head 216 from contact with the surface of the skin 14. The interfacial boot 220 is preferably constructed from silicone, since it provides a reasonable impedance match and is biocompatible for patient contact. Functionally, silicone may also be stretched across the acoustic head 216 by the user for a tight, gapless fit. The interfacial boot 220 may be treated as a single use, consumable part or a reusable, sterilizable part. In another construction, a partial vacuum may be applied to the skin 14 proximate the distal end 202 by a vacuum manifold 212 to enhance contact between the acoustic head 216 and the skin 14. In this or other constructions, the distal end 202 may be supplied with an acoustic gel 16 through the vacuum manifold 212 or through a fluid port 214 disposed proximate the acoustic head 216. In one variation, the ultrasound handpiece 200 may include both a vacuum manifold 212 and a fluid port 214, with the fluid port 214 being located circumferentially oppositely from a vacuum source 210 within the vacuum manifold 212.

Figure 7:
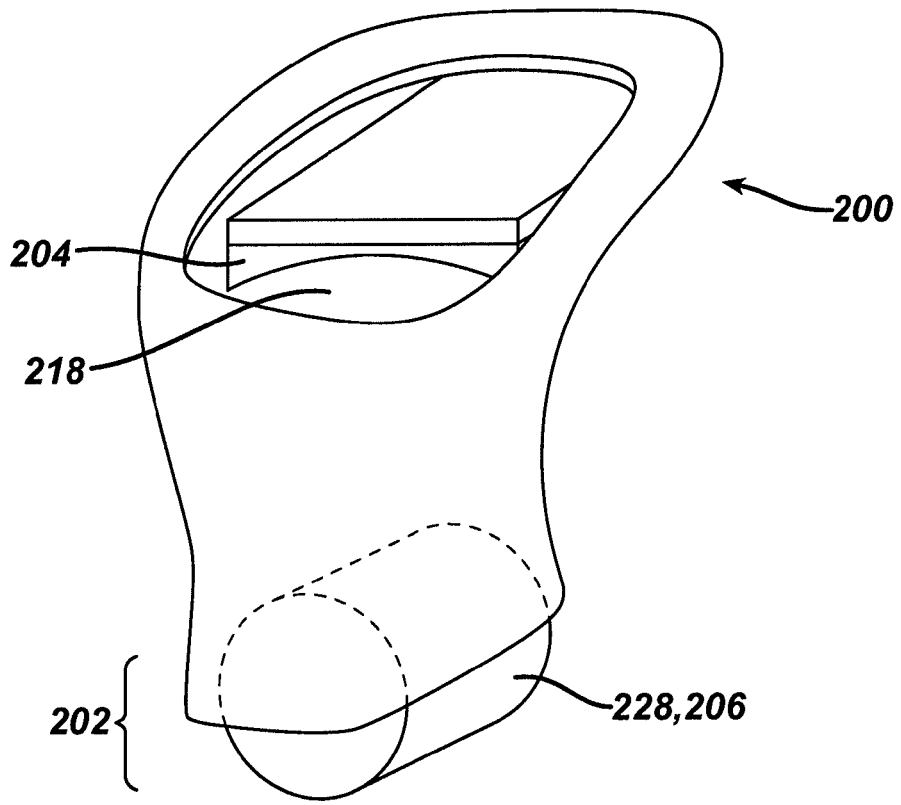
FIG. 7 is a perspective, cut-away view of a medical ultrasound handpiece with a distal rolling member or "ball." Obscured portions of the ball are outlined in phantom lines, and mounting structure, electrical connections, etc, have been omitted.
Figure 8:
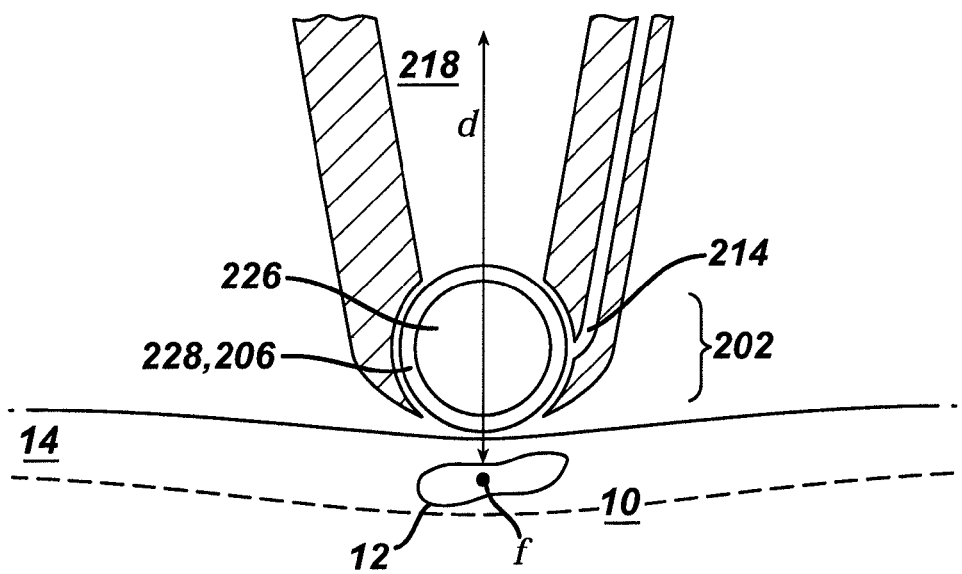
FIG. 8 is a schematic, side detail view of a distal end and distal rolling member.
Figure 9:
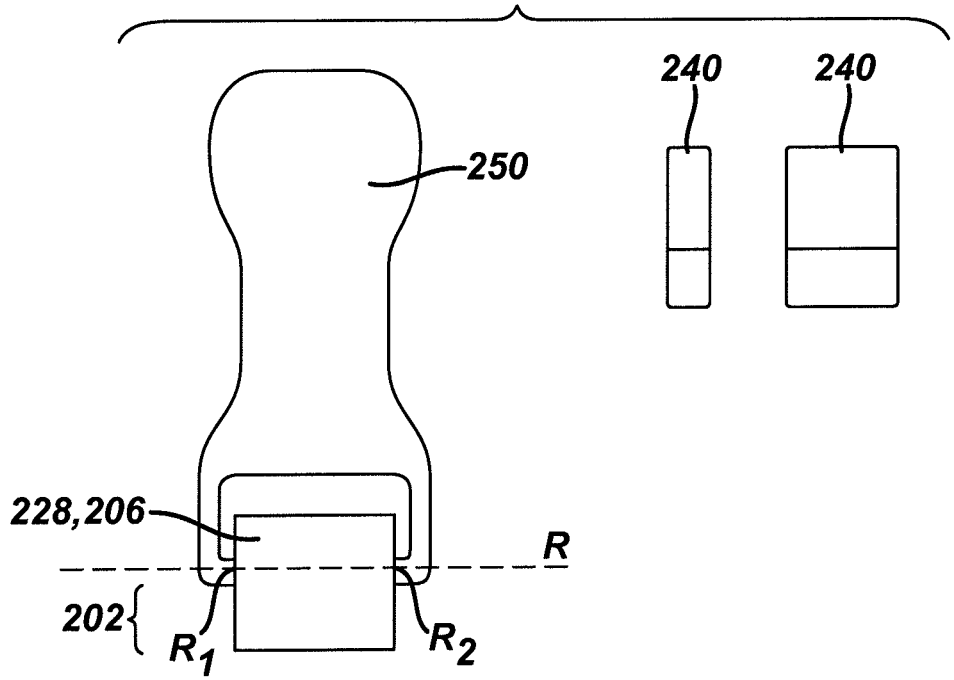
FIG. 9 is a front view of a medical ultrasound handpiece, as well as multiple rings for attachment to a distal rolling member or "ball."
Figure 10:
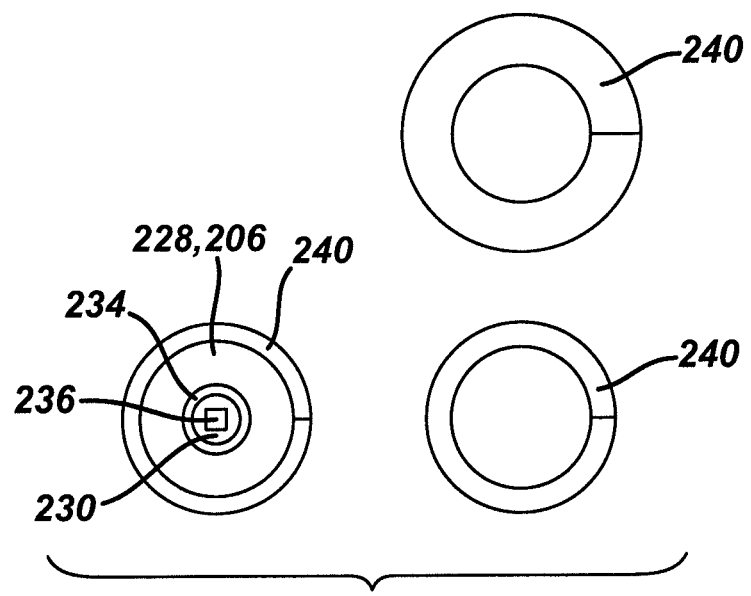
FIG. 10 is a side view of the "ball" of FIG. 9, as well as multiple rings for attachment to the "ball."
Figure 11:
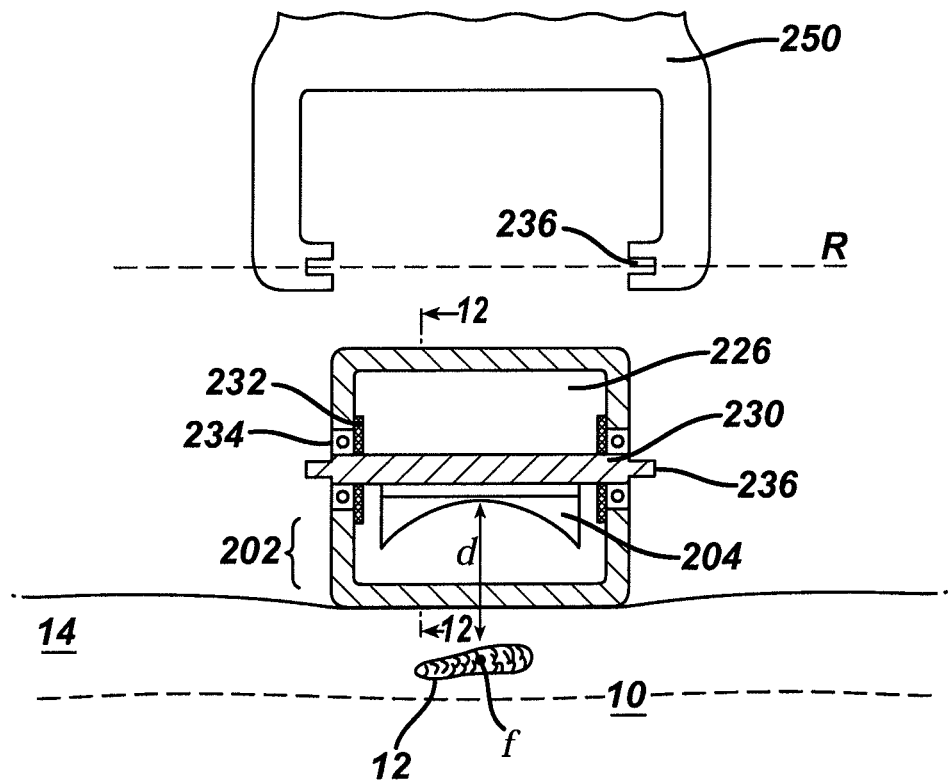
FIG. 11 is a partially exploded, cross-sectional front view of the "ball" of FIGS. 9-10
Figure 12:
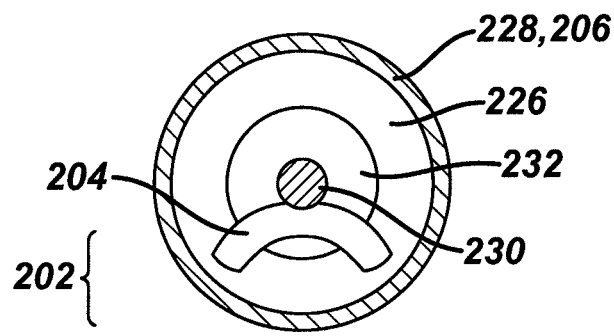
FIG. 12 is a cross-sectional side view of the "ball" of FIGS. 9-11.
Figure 13:
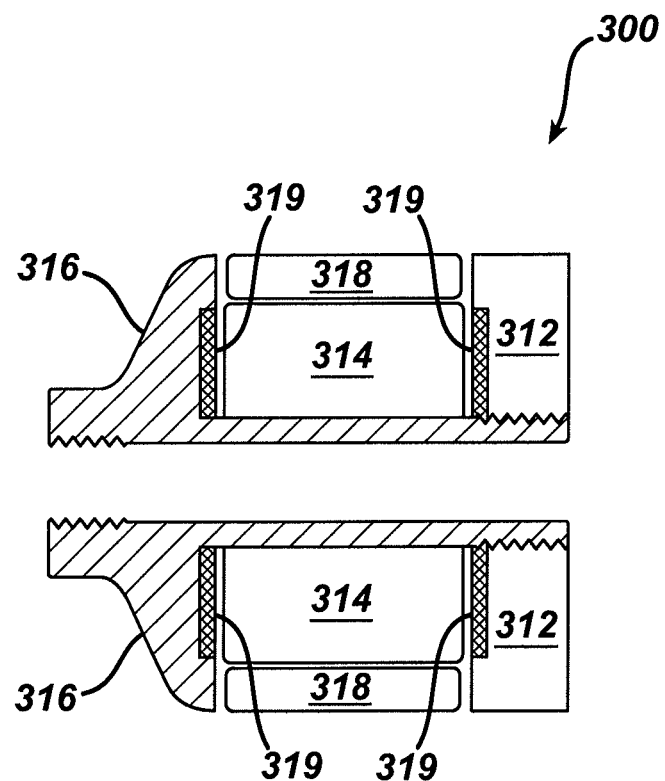
FIG. 13 is a schematic side view of a transducing structure in a medical ultrasound handpiece.

In a second expression of the second embodiment, shown in FIGS. 7 and 8, the distal rolling member 206 may be a cylinder or a generally smoothly curved volume of rotation 228, e.g., truncated ellipsoids, semi-ellipsoids, spheres, and the like, hereinafter generalized under the term "ball," disposed at the distal end 202. The ball 228 is externally coupled to the focusing ultrasound radiator 204 through an acoustic coupling medium 218 generally contained within the medical ultrasound handpiece 200. In one construction, the ball 228 may be formed from an acoustically transparent material. In another construction, the surfaces of the ball may be internally coupled through an acoustic coupling fluid or gel 226 contained within the ball 228. In one construction, acoustic gel 16 may be dispensed from within the ultrasound handpiece 200 as a coating on the surface of the ball 228 for use as a lubricant and acoustic coupling medium between the exposed surface of the ball 228 and the surface of the skin 14. In another construction, acoustic gel 16 may be dispensed onto the ball 228 through a separate fluid port 214 at the distal end 202.

In a third expression of the second embodiment, shown in FIGS. 9-12, the distal rolling member 206 may also be a ball 228. However, the ball 228 may be mounted to the medical ultrasound handpiece 200 for rotation about a predetermined axis, R. The ball 228 in fact serves in part as the distal end 202 of the medical ultrasound handpiece 200, with the focusing ultrasound radiator 204 being located within the ball 228 and the ball 228 being internally coupled to the ultrasound radiator 204 through an acoustic coupling fluid 226 contained within the ball 228. The ball 228 may include a stator 230 extending between the axial ends, $R_1$ and $R_2$, of the axis of rotation of the ball 228, one or more seals 232 disposed about the interface between the stator 230 and the axial ends $R_1$ and $R_2$ and, optionally, bearings 234 disposed at the interface between the stator 230 and the axial ends $R_1$ and $R_2$. The ultrasound radiator 204 is mounted to the stator 230, which may be fixed or user-adjustably fixed in orientation with respect to a handle portion 250 of the ultrasound handpiece 200. In one construction, the stator is fixed in orientation with respect to the handle by a pin-and-plug connection 236 between the stator 230 and the handle portion 250. In another construction, the stator is user-adjustably fixed in orientation with respect to the handle portion 250 by a pin-and-plug connection 236 in which the pin and plug (illustrated for exemplary purposes as rectangular projections and voids) may be conformably interconnected together in any of a plurality of positions. In one variation, the handle portion 250 may be a single use, consumable part. In another variation, the handle portion 250 may be a reusable, sterilizable part.

In an implementation of the third expression, a ring 240 of material may be removably attached to the ball 228. The ring 240 serves as a rotating patient-contact surface. In one variation, the ring 240 may be a single use, consumable part. In another variation, the ring 240 may be a reusable, sterilizable part. In one exemplary construction, one of a plurality of rings 240 having varying material thicknesses may be removably attached to the ball 228 to mechanically vary the position of the focusing ultrasound radiator 204 with respect to the distal end 202, and thus the depth at which the predetermined distance d is found within the skin 14. In another exemplary construction, one of a plurality of rings 240 having varying widths may be removably attached to the ball 228 to mechanically limit the transmission of diffuse ultrasound energy from the ball 228 to portions of the skin 14 adjacent to a linear facial feature 10.

In a method of using the expressions of the second embodiment, a dermal filler 12 is injected into the dermis of the facial feature 10, and the distal rolling member 206 is placed on the surface of the skin 14 over the facial feature 10. An acoustic gel 16 may be applied to the skin 14 over the facial feature 10 before or after placement of the distal rolling member 206 on the skin 14, depending upon the source of the acoustic gel, .e.g, separate applicator, application via a handpiece port 214, or transfer from the surface of the distal rolling member 206. The distal rolling member 206 is rollingly translated over the skin 14 to position the focal point f of the focusing ultrasound radiator 204 within the injected dermal filler 12, whereupon the ultrasound radiator 204 is powered to shear-thin the dermal filler 12. In one variation of the method, ultrasound radiator 204 is depowered and the distal rolling member 206 is further rollingly translated over the skin 14 to manipulate the dermal filler from the surface of the skin 14 while in a shear-thinned state. In another variation of the method, the ultrasound handpiece 200 is removed, and the dermal filler 12 is manipulated from the surface of the skin 14 while in a shear-thinned state.

In an implementation of the method relating to the first expression, the skin 14 of the facial feature 10 is pulled against the acoustic head 216 by a partial vacuum. This permits more robust definition of the skin surface plane in the presence of wrinkles, and serves to accurately position the surface of the skin 14 with respect to the focusing ultrasound radiator 204 and focal point f. The focusing ultrasound radiator 204 is subsequently powered to shear-thin the injected dermal filler 12.

A third embodiment of the invention is shown in FIGS. 13-21. The third embodiment includes a medical ultrasound handpiece assembly 300 having an ultrasound transducer 310, which may be configured as a "Langevin stack." A "Langevin stack" generally includes, in order, a first resonator or end-bell 312, a transducer portion 314, and a second resonator or fore-bell 316, as well as various ancillary components such as mounts, intermediate gain stages, and the like which may be interposed between or mounted around components 312, 314, and 316. Examples of ultrasonic surgical instruments with this general configuration are disclosed in U.S. Pat. Nos. 5,322,055 and 5,954,736. The transducer material in the transducer portion 312 may be piezoelectric, but may alternately be magnetostrictive, with a coils 318 and permanent magnets 319 bracketing the transducer material, or electrostrictive. Unless otherwise indicated, illustrations omitting specialized transducer components as the aforementioned coils and magnets should be understood as being generic, schematic representations rather than limiting disclosures. The ultrasound handpiece assembly 300 and ultrasound transducer 310 are coupled to an end effector 320, as further described below. Examples of medical ultrasound handpieces coupled to ultrasonic blades and other surgical end effectors are disclosed in U.S. Pat. Nos. 6,278,218; 6,283, 981; 6,309,400; 6,325,811; and 6,423,082, as well as U.S.

patent application Ser. No. 11/726,625, entitled "Ultrasonic Surgical Instruments," filed on Mar. 22, 2007, and Ser. No. 11/998,543, entitled "Ultrasonic Surgical Instrument Blades," filed on Nov. 30, 2007, all of which are incorporated by reference herein. The ultrasonic transducer 310 and coupled end effector 320 are preferably an integral number of one-half system wavelengths ($n\lambda/2$) in length. Unless otherwise indicated, illustrations omitting routine components or illustrating partial structures should be understood as being generic, schematic representations rather than limiting disclosures.

The end effector 320 includes, in order, a distal probe tip 322, a probe neck 324, a proximal probe dilation region 326, and an ultrasonically active shaft 328, with the shaft coaxially held within an ultrasonically inactive probe sheath 330 and operatively connected to the dilation region 326. The probe tip 322 is generally rounded or paddle like, but may include a minor distal-most blade portion 323 as described below. The dilation region 326 is configured to have an average outside diameter that is equal to or larger than the average outside diameter of the probe tip 322, as well as that of probe neck 324. The probe sheath 330 is configured to have an outside diameter that is approximately equal to the outside diameter of the dilation region 326. The dilation region 326 is positioned at a proximal anti-node 332, and is used to dilate the surface of the skin 14 so that the insertion force associated inserting with the probe sheath 330 under an initial perforation is minimized. A small initial hole, formed by probe tip 322 or another instrument, followed by reversible dilation appears to create the smallest long term hole in the surface of the skin 14. The end effector should emit about 1 to 20 watts of effective power, but may have an instantaneous requirement of up to about 30 watts during penetration of the skin 14. It is important to note that while dermal filler procedures are a primary application for such devices due to post-surgical cosmetic concerns, the devices may also advantageously be scaled for use in deep blunt dissection or sculpting procedures where the snagging of the probe sheath 330 on tissue surfaces during an insertion transition from the device blade/probe 322-326 to the probe sheath 330 is a concern.

Figure 14:
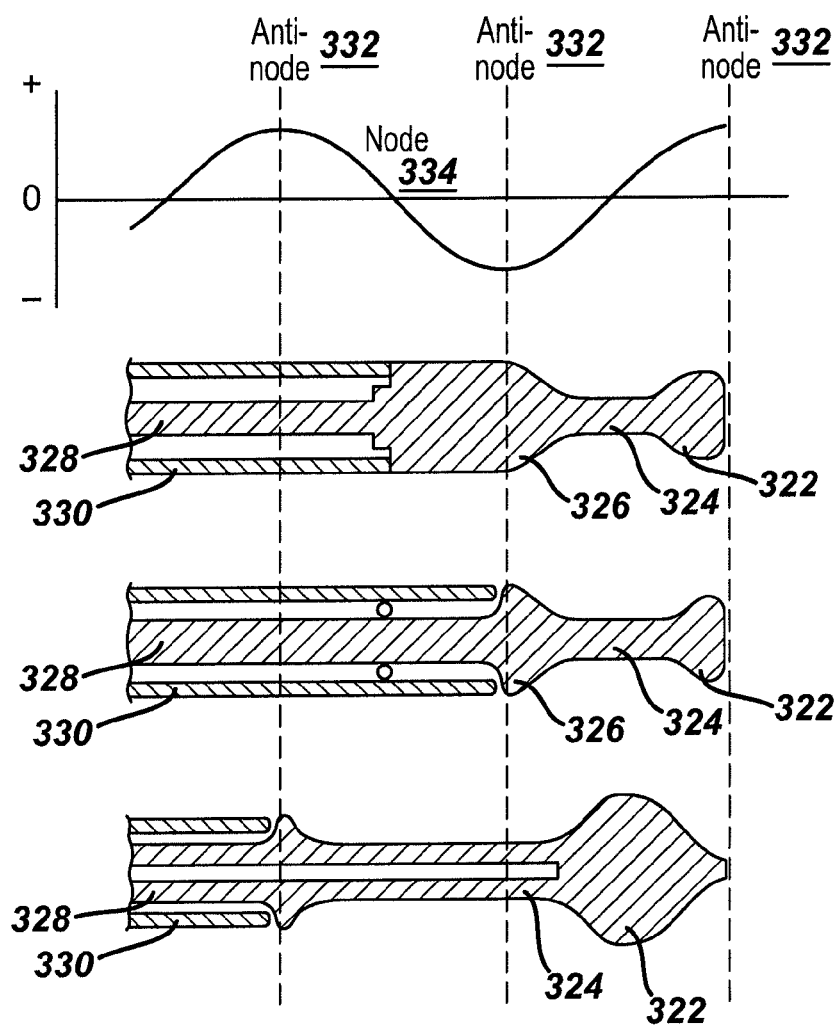
FIG. 14 is a cross-sectional side view of various end effector probe constructions.

In a first expression of the third embodiment, shown in FIG. 14, the probe dilation region 326 is located proximate the first anti-node 332 proximal from the probe tip 322. In variations of the first embodiment, the dilation region could be located proximate an even more proximal anti-node. In one construction, the junction between the dilation region 326 and the ultrasonically inactive probe sheath 330 (when the end effector 320 is closed) may be located at a node 334 proximal from the anti-node 332. This allows for a very tight junction, which minimizes the likelihood of tissue snagging at the interface between the dilation region 326 and the probe sheath 330. In another construction, the junction between the dilation region 326 and the probe sheath 330 (when the end effector 320 is closed) may be located at an anti-node 332. The junction is preferably located at the same anti-node 332 as the transition between the probe neck 324 and the dilation region 326. The latter construction minimizes ultrasound gain impact, but necessitates a gap between the dilation region 326 and the probe sheath 330. The impact of the gap is somewhat mitigated because the ultrasonically active shaft 328 and dilation region 326 are active at the junction and will tend to self-clean.

Figure 15:
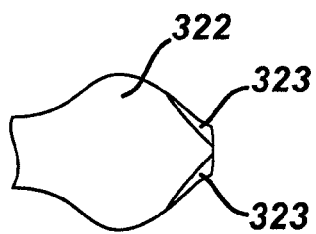
FIG. 15 is a side view of a distal probe tip.
Figure 16:
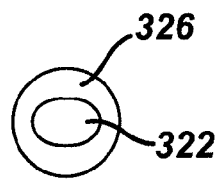
FIGS. 16-17 are front views of the distal probe tips shown in FIG. 15
Figure 17:
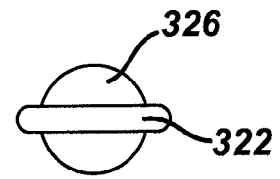

In a second expression of the third embodiment, shown in FIG. 15, the distal probe tip 322 may be sharpened to include a distal-most mechanical blade portion 323 to facilitate rapid penetration with minimal thermal spread. The mechanical blade portion 323, while useful to enable rapid skin penetration, is preferably minimized in size and extent to reduce the likelihood that other tissue structures will be inadvertently damaged or disrupted as the probe tip 322 is wanded back and forth to shear-thin, blunt dissect tissue, and/or emulsify fat. Alternately, in a third expression of the third embodiment, illustrated in the topmost example in FIG. 14 and in an end view in FIG. 16, the probe tip 322 may be dull. A dull tip allows the user to safely push the probe tip 322 around in a blunt dissection mode, while initial penetration and dilation of the skin are accomplished with an unpowered needle or an obturator.

In a fourth expression of the third embodiment, shown in FIGS. 17-21, the surface area of the distal probe tip 322 and/or probe neck 324 is increased, while holding the cross-sectional area of the part(s) constant, by configuring at least one of these structures to have an undulating periphery in cross-section. This improves power transfer efficiency into the dermal filler 12 and/or other target tissues. In one construction, illustrated in the bottommost example in FIG. 14 and in an end view in FIG. 17, the probe tip 322 may have a high aspect ratio, with portions of the probe tip 322 being wider than the width of the probe dilation region 326. A high aspect ratio probe tip 322 allows for an increase in the surface area-to-volume ratio of the device, but may be inserted through, or itself create, a small incision-like slit in the surface of the skin 14. Such constructions are intended to be within the scope of devices where the dilation region 326 has an average outside diameter that is equal to or larger than the average outside diameter of the probe tip 322. In another construction, shown in FIGS. 18 and 19, a portion of the probe neck 324 may be configured to include a plurality of longitudinally extending, circumferentially arrayed slats 324a with openings 324b to an internal lumen 331. The slats 324a may be have a sheet-like cross-sectional profile, or may be configured to include one or more externally protruding structures, such as ribs 324c, in order to increase the surface-area-to-volume ratio of the device. In yet another construction, shown in FIGS. 20 and 21, portions of the distal probe tip 322 and/or probe neck 324 may be configured as a solid rod defining a plurality of longitudinally extending, circumferentially arrayed ribs 324c alternating with plurality of similarly disposed indentations 324d. In one modification of the latter construction, a proximal portion of the probe neck 324 may be configured to provide an internal lumen 331 in fluid communication with the indentations 324d for the injection and/or withdrawal of fluid material proximate the probe tip 322.

Finally, it is important to note that in various constructions, and as illustrated in middle example of FIG. 14, the end effector 320, and particularly the probe tip 322 and/or probe neck 324, may be axisymmetric or axially asymmetric, so that the term diameter should be understood generally as referring to the characteristic width of the referenced part, rather than a geometric diameter determined with respect to a single central longitudinal axis.

Figure 22:
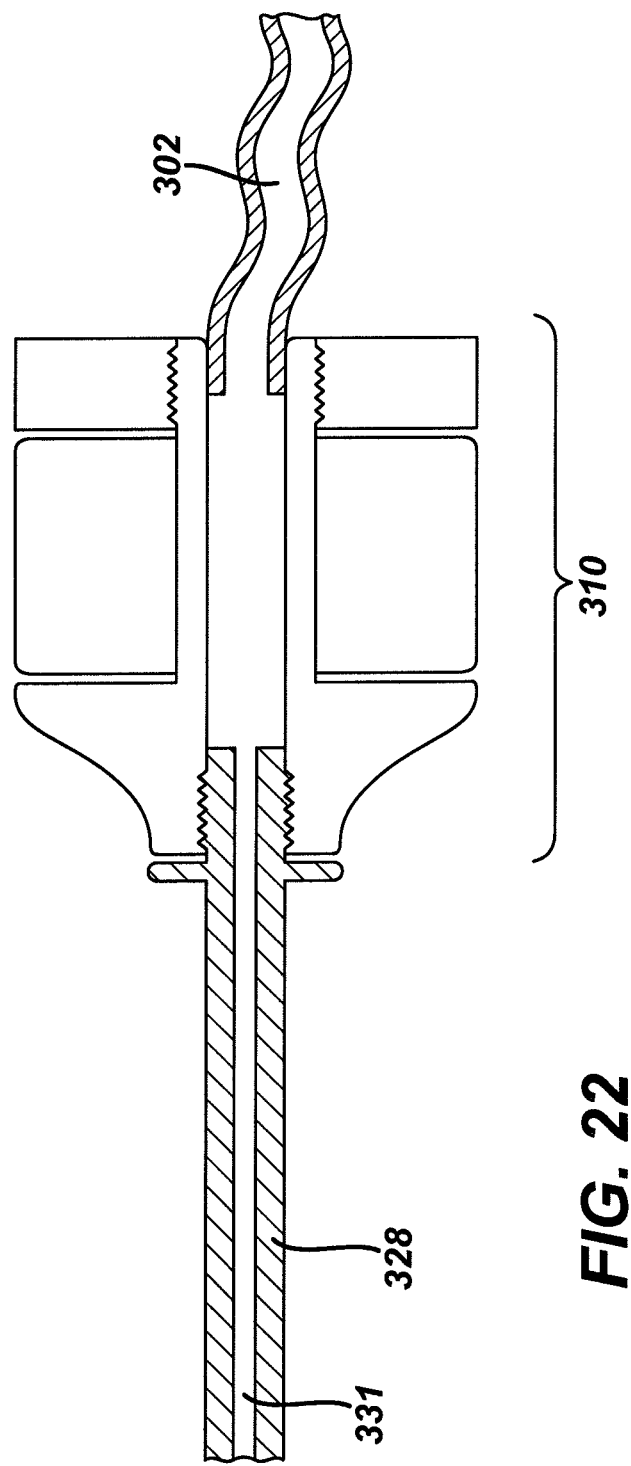
FIGS. 22-24 are schematic side views of aspects of a medical hand piece assembly relating to fluid communications configurations.
Figure 23:
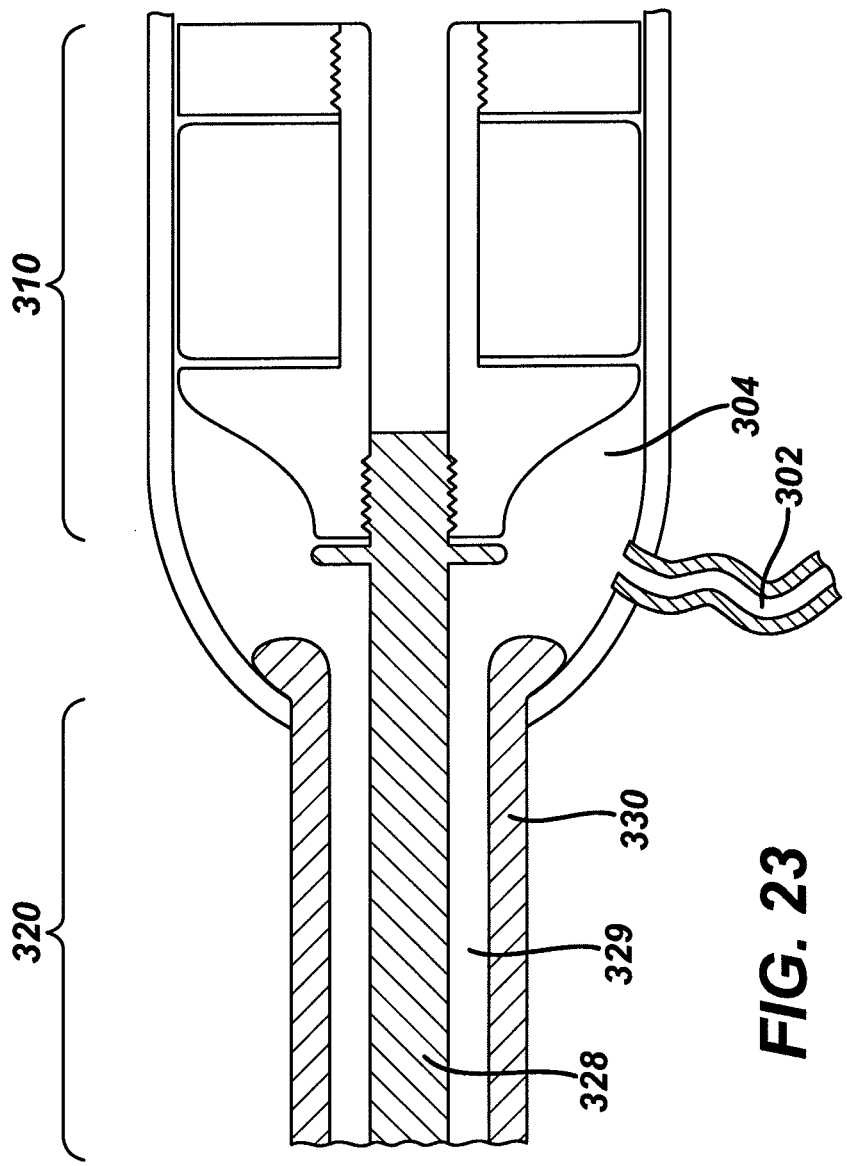

In a fifth expression of the third embodiment, the medical ultrasound handpiece assembly 300 is configured to shear-thin or fluidize a material transiting within one more lumens in the end effector 320. The challenge of injecting precise amounts of dermal filler in a precise location along a facial feature 10, such as the naseolabal fold, increases as the viscosity of the dermal filler increases and the size of the injection needle lumen decreases. Ultrasonic energy may be used to shear-thin the dermal filler while the dermal filler passes from a reservoir on the surgical instrument and through a lumen in the end effector 320. Ultrasonic energy may also be used to shear-thin the dermal filler or to fluidize other materials while those materials are transiting within the end effector 320. Ultrasound handpiece assembly 300 consequently may include at least one fluid lumen 302 in fluid communication with the end effector 320. In one construction, ultrasonically active shaft 328 includes an internal lumen 331, with fluid lumen 302 in fluid communication with internal lumen 331. In one exemplary construction, shown in FIG. 22, shaft 328 is secured to ultrasound transducer 310, which may be configured as a "Langevin stack" with an integrated fluid path. In another construction, the interstitial space 329 between ultrasonically inactive probe sheath 330 and shaft 328 serves as a fluid lumen, with fluid lumen 302 in fluid communication with the proximal end of probe sheath 330 and interstitial space 329. In one exemplary construction, shown in FIG. 23, a fluid lumen 302 bypasses the ultrasound transducer 310 within the handpiece assembly 300 and joins a manifold 304 receiving the proximal end of probe sheath 330 upon assembly of the end effector 320 with the handpiece assembly 300. In one variation, the internal lumen 331 is used to suction material from the distal end of the end effector 320, and the interstitial space 329 is used to inject materials such as dermal filler or irrigation fluids. In another variation, the internal lumen 331 is used to inject materials such as dermal filler or irrigation fluids, and the interstitial space 329 is used to suction material from the distal end of the end effector 320. In other variations, only one structure may serve as a fluid lumen, and both functions may take place through that lumen. Where the interstitial space 329 is used as a fluid lumen, the end effector may be opened by retracting the probe sheath 330 from the dilation region 326. Adjustment mechanisms for retracting the probe sheath 330 are described in detail in the context of the fourth embodiment of the invention, described below.

Figure 24:
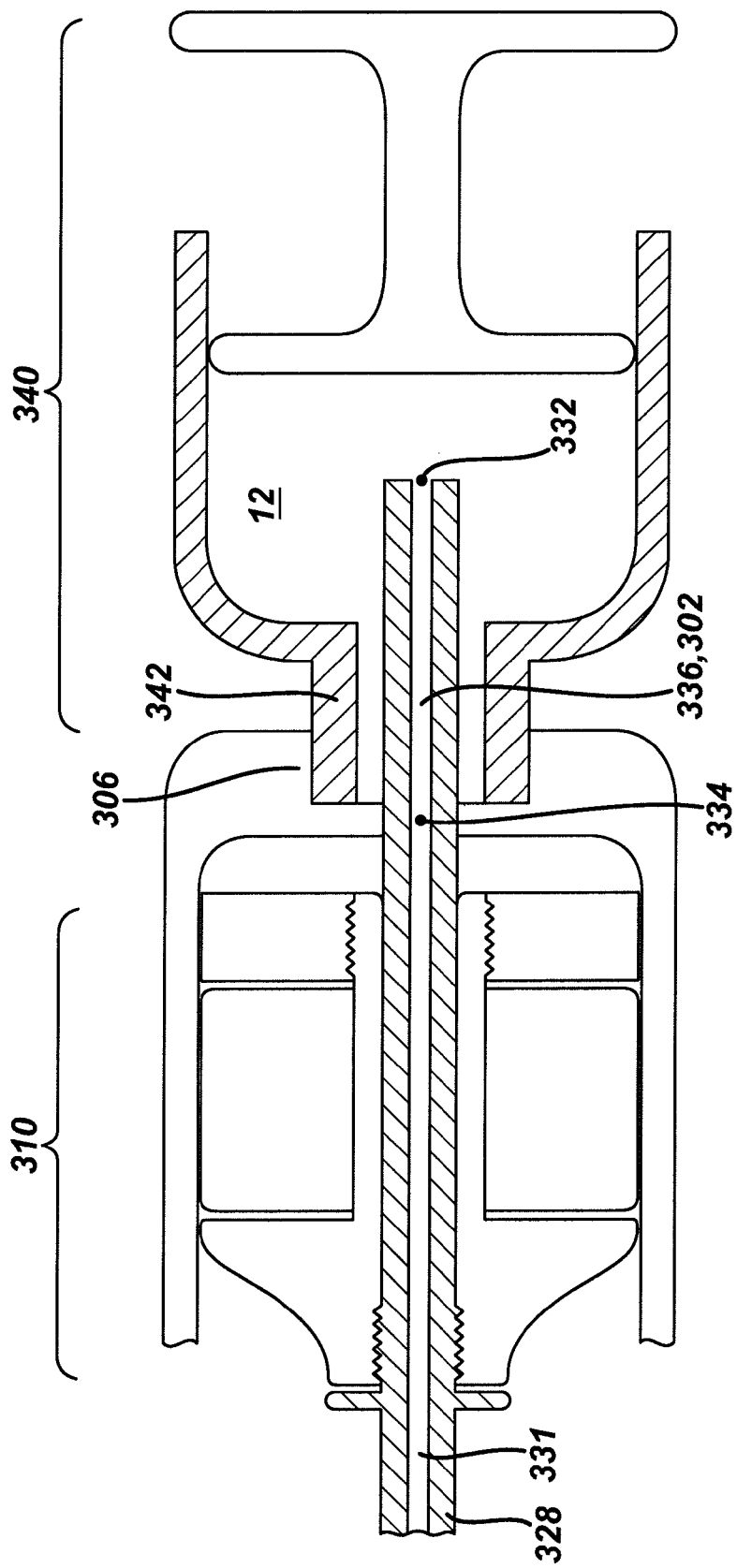

In an implementation of the fifth expression, shown in FIG. 24, ultrasonically active shaft 328 includes an oppositely projecting portion 336 serving as the fluid lumen 302. Portion 336 projects from a proximal end of the ultrasound transducer 310 and within a handpiece port 306 configured for connection to a syringe 340 via, e.g., a complementary-configured port 306 and syringe tip 342 such as those in found luer lock connections. Portion 336 projects within at least the syringe tip 342, whereupon ultrasound energy transmitted to portion 336 during operation of ultrasound transducer shear-thins dermal filler held within syringe 340. The handpiece port 306 is preferably located at a node 334 of the projecting portion 336. The free end of the projecting portion 336 is preferably located at an anti-node 332 so as to maximize shear-thinning at the entrance of the comparatively narrow-bore fluid lumen 302. In other implementations, syringe 340 may be combined within the handpiece assembly 300 as a unit, so that port 306 is an internal point of connection to an integrated syringe structure.

In a method of using the expressions of the third embodiment, a dermal filler 12 is injected into the facial feature 10, and at least the distal probe tip 322 of the device is inserted beneath the surface of the skin 14. The dermal filler 12 may be injected before or after insertion of the distal probe tip 322 within the skin, depending upon the source of the dermal filler, e.g., separate applicator or injection through a fluid lumen of the end effector 320 (such as interstitial space 329 or internal lumen 331). Also, the probe tip 322 may be inserted through an existing perforation in the skin 14 (such as made by an applicator or obturator) or through a perforation made by a distal-most blade portion 323 of the probe tip 322. The ultrasound transducer 310 is powered to operate the probe tip 322, and the probe tip is inserted into the dermal filler 12 to shear-thin the filler. In one variation of the method, the ultrasound transducer 310 is depowered and the dermal filler 12 is manipulated from the surface of the skin 14 while in a shear-thinned state. In another variation of the method, the ultrasound transducer 310 is depowered and the probe tip 322 withdrawn from the skin, whereupon the dermal filler 12 is manipulated from the surface of the skin 14 while in a shear-thinned state.

In a preferred implementation of the method, the probe dilation region 326 is inserted beneath the surface of the skin 14 after the ultrasound transducer 310 is powered, whereupon the ultrasonically inactive probe sheath 430 is inserted beneath the skin to protect the surface of the skin 14 from unintended contact with ultrasonically active portions of the probe. Ultrasound transducer 320 may be depowered prior to removal of the probe sheath 430, dilation region 326, and probe tip 422 to further protect the surface of the skin 14. In a variation of the implementation possible where separate instruments provide initial penetration and dilation of the skin, the dilation region 326 is brought into contact with the surface of the skin, whereupon the ultrasound transducer 320 is powered and the dilation region 326 and probe sheath 430 are inserted beneath the skin.

In another method of using the expressions of the third embodiment, the devices may be used to perform blepheroplasty. The distal probe tip 322 is inserted beneath the surface of the skin above a periorbital fat pad. Although the probe tip 322 may be inserted through an existing perforation in the skin 14 (such as made by an obturator), the skin is preferably perforated by a distal-most blade portion 323 of the probe tip 322. The ultrasound transducer 310 is powered to operate the probe tip 322 and to advance the distal probe tip 322 into the periorbital fat pad. Advantageously, devices scaled for typical dermal filler procedures are also suitably scaled for blepheroplasty, such that the probe dilation region 326 and the ultrasonically inactive probe sheath 330 may be inserted beneath the surface of the skin 14 during advancement of the distal probe tip 322. This isolates the skin 14 from prolonged contact with ultrasonically active portions of the probe. Upon reaching the interior of the periorbital fat pad, the distal probe tip 322, and potentially a distal portion of the probe neck 324, is manipulated within the periorbital fat pad while the ultrasound transducer 310 is powered to fluidize and shift or lyse and remove periorbital fat. The distal probe tip 322 may also be used to shear-thin a dermal filler 12 that has been injected into the periorbital fat pad in order to further shape the pad, or to inject a dermal filler 12 to take the place of previously removed fat.

A fourth embodiment of the invention is shown in FIGS. 25-33. The fourth embodiment is substantially similar to the third embodiment, as heretofore described, but omits the probe dilation region 326, and consequently the junction between the ultrasonically inactive probe sheath 330 and the dilation region 326. In the referenced figures, elements with reference numbers differing only in the lead digit, e.g., distal probe tips 322 and 422, should be understood to be similar or identical to those elements described in the context of the third embodiment, but for the above-indicated points of distinction. With specific regard to the fourth embodiment, ultrasonically active shaft 428 is coaxially held within the ultrasonically inactive probe sheath 430 and operatively connected to the probe neck 424. The probe sheath 430 is configured such that the distal end of the probe sheath 430 is slidably operable to both cover and expose at least the probe tip 422. It is important to note that in some procedures, dermal fillers are injected substantially below the dermis, particularly at or above the interface between the musculature and the periosteum in order to alter facial features such as the jaw line. Consequently, some expressions of the embodiment are adapted for use in this application, or similar microsurgical procedures in which ultrasonic instruments are used to inject material, remove material, or dissect tissues at very precise locations.

Figure 25:
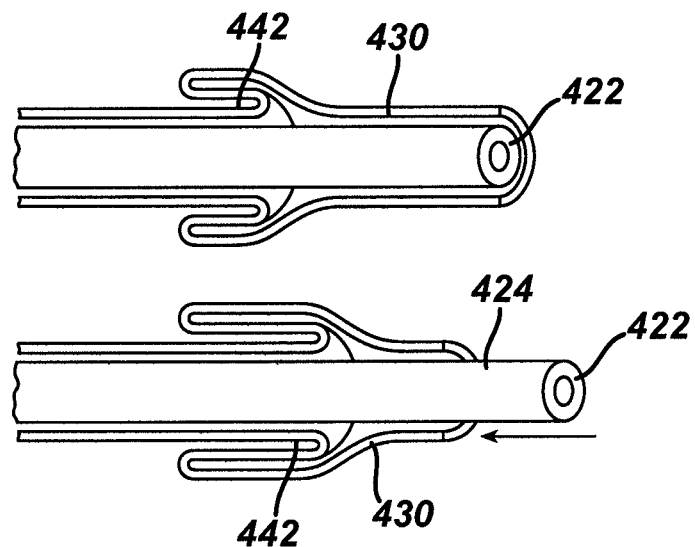
FIG. 25 is a cut-away side view of a probe sheath retraction mechanism.

In a first expression of the fourth embodiment, shown in FIG. 25, at least a portion of the ultrasonically inactive probe sheath 430 is longitudinally flexible and includes an S-shaped crease 442. The crease 442 allows the distal end of the probe sheath 430 to slidably retract in response to a longitudinal resistance to the advancement of the probe sheath 430. Specifically, portions of the probe sheath 430 distally adjacent to the crease 442 may slide proximally over the crease 442, and ultimately be folded under successive distally adjacent portions of the sheath, in response to sufficient and continued longitudinal resistance to advancement. This folding action causes the probe sheath 430 to retract relative to the ultrasonically active portions of the probe, exposing greater lengths of the probe tip 422 and probe neck 424. The stiffness of the probe sheath 430 may be adapted such that portions of the probe sheath 430 distally adjacent to the crease 442 will not fold into the crease as the probe tip 422 and probe sheath 430 are advanced into soft tissue, but will fold into the crease when the probe tip 422 is advanced into stiff tissue such as muscle or hard tissue such bone. The stiffness may also be adapted solely with respect to hard tissue. Soft tissues proximate the insertion track can then be substantially protected from ultrasonically active portions of the probe both during and after advancement of the probe.

Figure 26:
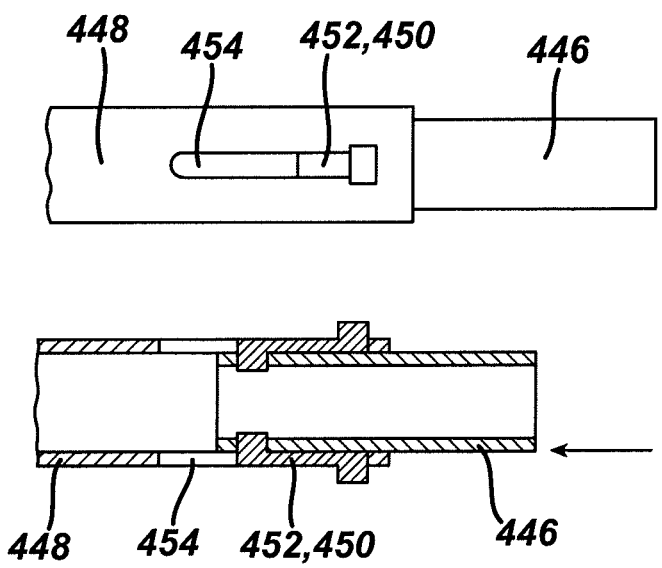
FIG. 26 combines a side view ("Before") and cross-sectional top view ("After") to illustrate another probe sheath retraction mechanism.

In a second expression of the fourth embodiment, shown in FIG. 26, the distal end of the ultrasonically inactive probe sheath 430 includes a spring-biased mechanism 450 configured to normally extend a distal-most segment 446 of the probe sheath 430 out from a proximally adjoining segment 448, but slidably retract the distal-most segment 446 in response to sufficient longitudinal resistance to the advancement of the probe sheath 430. In one construction, the spring-biased mechanism 450 includes at least two circumferentially opposing elastic dogbones 452 having opposing ends anchored to the distal-most segment 446 and the proximal segment 448, respectively. Preferably, the elastic dogbones 452 are configured to stretch within longitudinal slots 454 of the proximal segment so that interference between the proximal ends of the dogbones 452 and the proximal ends of the longitudinal slots 454 limits the travel of the distal-most segment 446 In modifications of the construction, other structures such as internal stops in the interior of the proximal segment 448, external stops on the exterior of distal-most segment 446, and longitudinal grooves in the proximal end of the distal-most segment 446 may serve as travel limiting structures. In other constructions, coil springs or volute springs may be used with various combinations of anchorings, slots, and stops.

The spring force of the spring-biased mechanism 450 may be adapted such that the distal-most segment 446 will not appreciably expose proximal portions of the probe tip 422 as it is advanced into soft tissue, but will operate when the probe tip 422 is advanced into stiff tissue such as muscle or hard tissue such bone. Soft tissues proximate the insertion track can then be substantially protected from the ultrasonically active portions of the probe both during and after advancement of the probe. The probe sheath 430 and sheath segments 446, 448 are constructed from a comparatively rigid material, and preferably constructed from thermoplastic materials such as ULTEM® (a polyetherimide marketed by SABIC Americas, Inc. of Houston, Tex.), fiber reinforced composites (e.g., pultruded glass or carbon fiber tubing), or braided catheter tubing.

Figure 27:
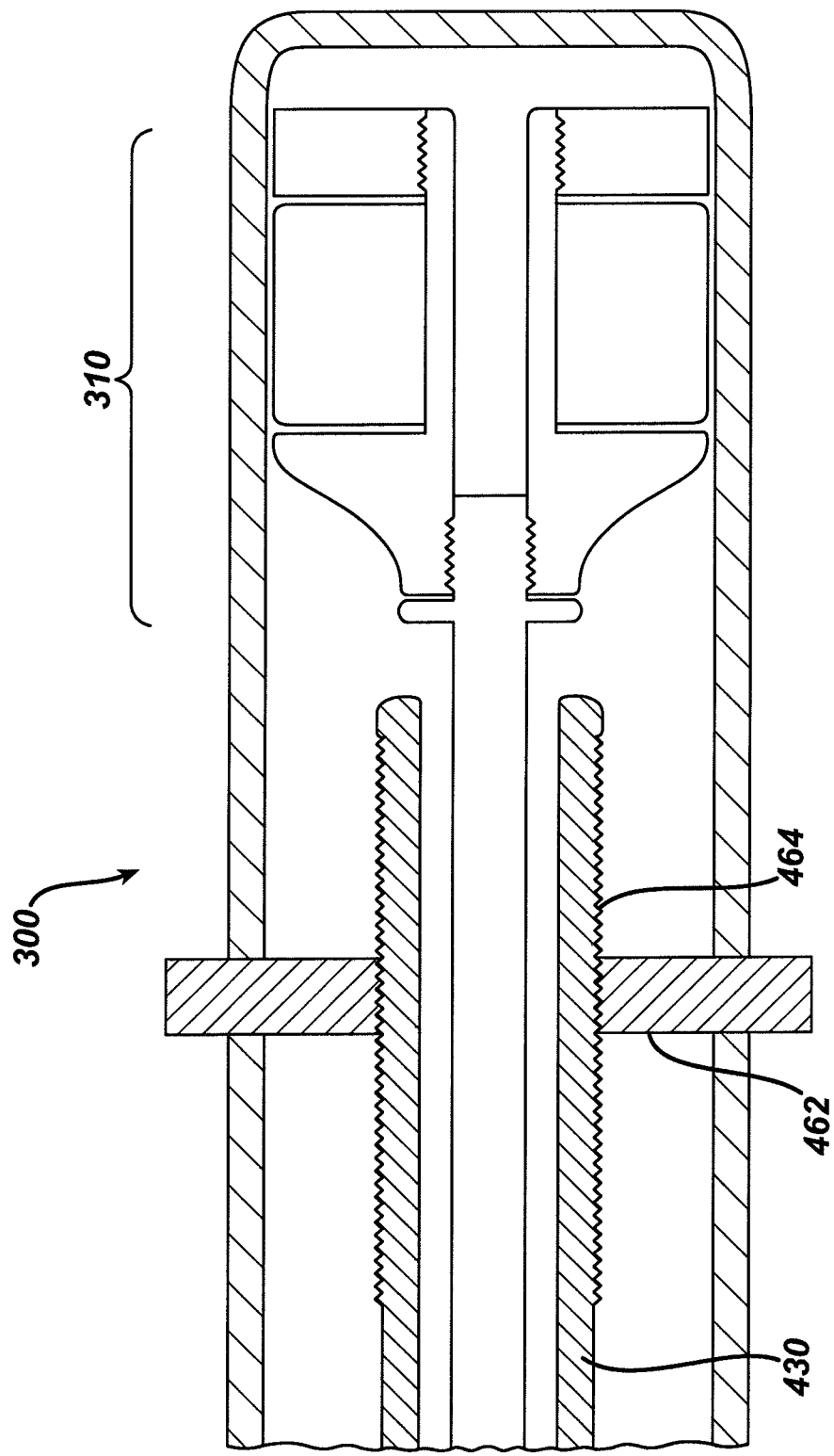
FIGS. 27 and 28 are a schematic side views of medical hand piece assemblies relating to operation of the probe sheath.
Figure 28:
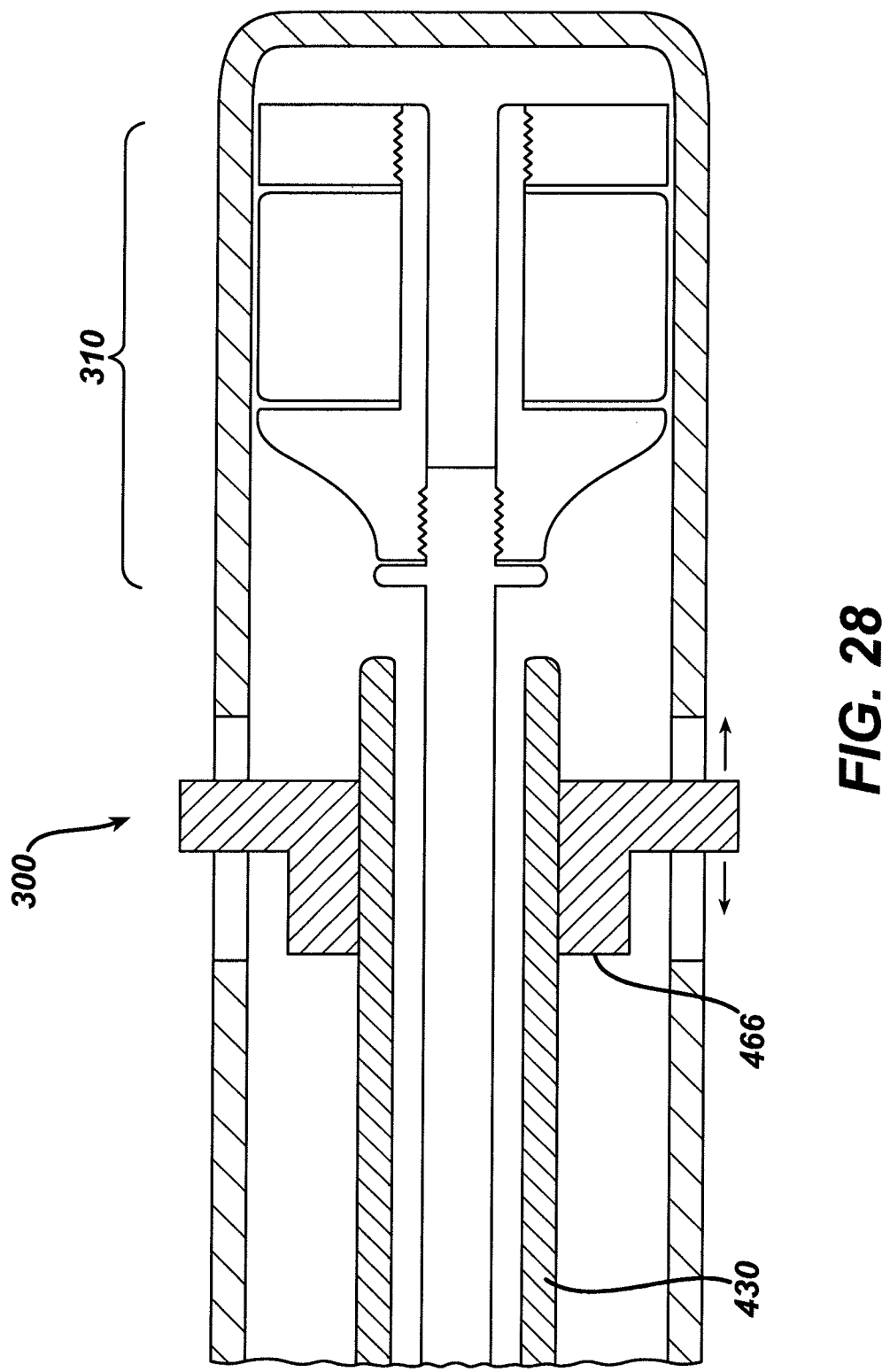

In a third expression of the fourth embodiment, shown in FIGS. 27 and 28, a proximal portion of the ultrasonically inactive probe sheath 430 is coupled to an adjustment mechanism 460 configured to positively position the distal end of the probe sheath 430 over at least the distal probe tip 422. In one construction, the adjustment mechanism 460 includes an internally threaded drive member 462 that couples to external threads 464 on the proximal portion of the probe sheath 430. Such threads may be integral to the proximal portion of the probe sheath 430 or be part of an adapter bound to the proximal portion of the probe sheath 430. In another construction, the adjustment mechanism includes a slide member 466 that is mechanically linked or chemically bound to the proximal portion of the probe sheath 430. The adjustment mechanism is manually or mechanically actuated to slidably operate the distal end of the probe sheath 430 over at least the distal probe tip 422.

The adjustment mechanism is preferably a component of the medical ultrasound handpiece assembly 400. Positive positioning of the distal end of the probe sheath 430 over at least the distal probe 422 from a handpiece assembly enables ready modification of the contact length between tissue and at least the distal probe tip 422 to a length suitable for the intended target. For example, the distal most-end of the probe sheath 430 may be retracted to expose a predetermined length of the probe tip 422 (and potentially the probe neck 424, as further discussed below) corresponding to the spread of tiers in which a dermal filler has been injected. Where a single, small tier has been injected, only a small contact length is needed, with greater contact lengths increasing the risk of unintended tissue damage. Where multiple tiers have been injected, a larger contact length may be desired so as to permit shear-thinning of the entire tiered depth in a single procedure. Finally, in other procedures, and particularly procedures such as liposuction, very large contact lengths may be required into order to employ the surgical device efficiently. For further example, as noted above, dermal fillers may be injected even below musculature in some procedures. Positive positioning of the distal end of the probe sheath 430 over the distal probe tip 422 from the handpiece assembly enables shallower tissues proximate the insertion track, even stiff or tough tissues, to be substantially protected from ultrasonically active portions of the probe after further advancement of ultrasonically active portions of the probe.

Figure 29:
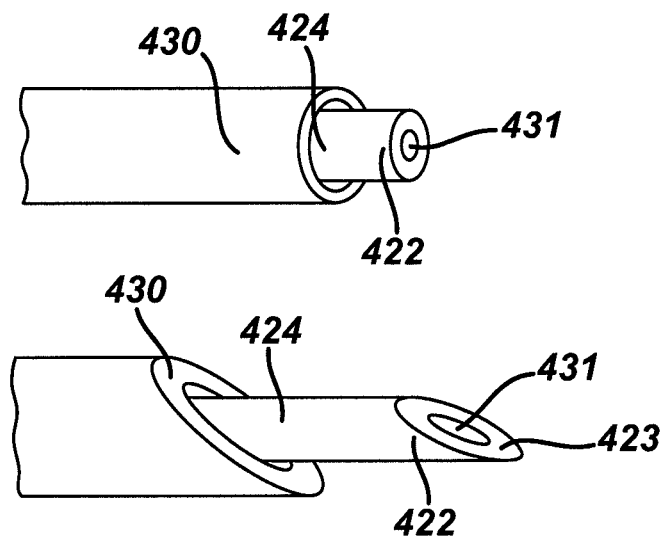
FIGS. 29-31 are perspective views of varying probe configurations.

In implementations of the expressions of the fourth embodiment, shown in FIG. 29, the distal probe tip 422 may be a blunt tip with an opening to an internal lumen 431 continuing through the probe neck 424 and ultrasonically active shaft 428 to establish fluid communication with the handpiece assembly 400. The blunt tip is atraumatic and will tend to stay within structures like fat pockets once it has been introduced. The blunt tip may also be used in other procedures to sculpt bone and cartilage or to remove deposits. Alternately, the probe tip 422 may be a beveled needle tip with a distal-most blade portion 423 and an opening to the internal lumen 431. The needle tip is useful for penetrating tough tissues such as fascia. Probe tip and probe neck configurations such as those described in the context of the third embodiment are envisioned as well. Finally, the distal-most portion of the ultrasonically inactive probe sheath 430 may be blunt, but may alternately be beveled to aid in insertion into soft tissue.

Figure 30:
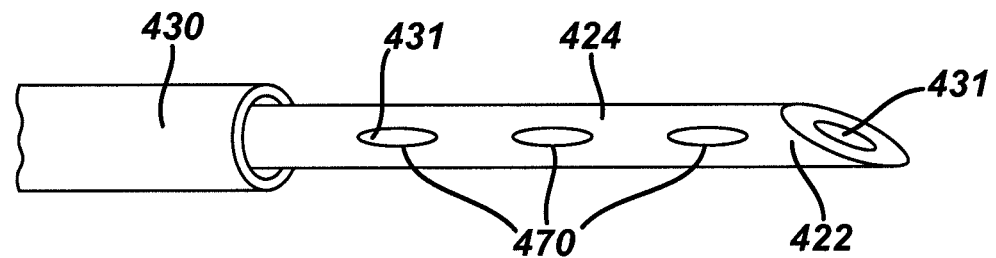
Figure 31:
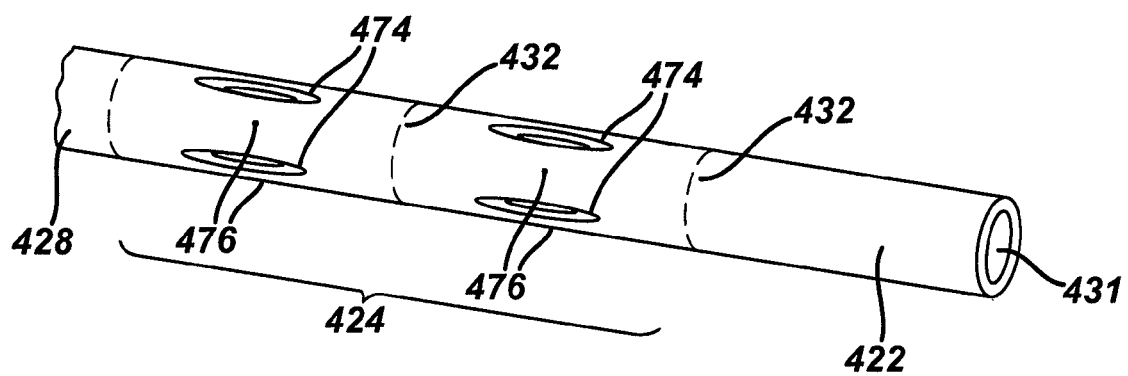
Figure 32:
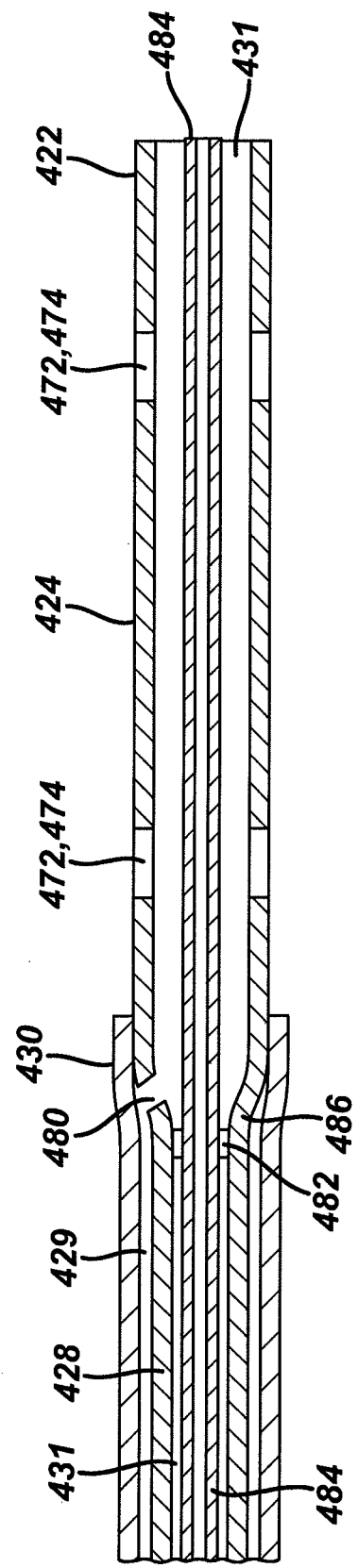
FIG. 32 is a schematic side view of a probe configuration including a cannula.

In further implementations of the expressions of the fourth embodiment, shown in FIGS. 30 and 31, the probe neck 424 may include a plurality of slots 470 opening into an internal lumen 431. As indicated earlier, probe tip configurations such as those described in the context of the third embodiment are envisioned as well, so that internal lumen 431 may or may not extend distally into distal probe tip 422. In a first construction, the plurality of slots is configured as a longitudinal array of slots 472. This allows the device to provide additional injection or suction capability along an extended length of the active probe when the probe neck 424 is exposed. In a second construction, the plurality of slots is configured as a plurality of longitudinally elongated, circumferentially arrayed slots 474 alternating with plurality of similarly elongated and disposed bridges 476. The bridges, of course, join proximal and distal portions of the probe neck 424. However, the bridges will also develop a transverse mode of vibration when the probe neck 424 (and ultrasonically active shaft 428 and probe tip 422) are driven longitudinally by the ultrasound transducer 410. The plurality of slots 474 and alternating bridges 476 are preferably located at a node 434. When the bridges 476 experience transverse vibration, proximate dermal filler will be readily shear-thinned. Where tissue removal can be performed, or in other procedures such a liposuction, soft tissues proximate to the bridges 476 will be readily lysed for suction by the end effector 420. The applicants note that in other procedures, the probe sheath 430 may be partially or completely omitted in favor of a separate obturator, with the remainder of the probe scaled to dimensions generally unsuitable for dermal applications. A probe sheath 430, if any, would serve to protect the user from accidental contact with the active portions of the probe 428 at the proximal end of the end effector 420, with a distal end of the end effector being exposed for several inches or more. The longitudinal array of slots 472 may then be configured as a longitudinal array where each longitudinal position in the array includes a plurality of longitudinally elongated, circumferentially arrayed slots 474 alternating with plurality of similarly elongated and disposed bridges 476. The longitudinal positions in the array may correspond to nodes 434. Such a extended-length device may be usefully employed in conventional liposuction procedures occurring essentially within the hypodermis.

In yet further implementations of the expressions of the fourth embodiment, where all of the ultrasonically active shaft 428, probe neck 424, and distal probe tip 422 include an internal lumen 431, and the shaft 428 and ultrasonically inactive probe sheath 430 form an interstitial space 429, a proximal portion of the probe neck 424 may include a lateral aperture 480 for fluid communication between the internal lumen 431 and the interstitial space 429, and a seal 482 disposed proximally from the lateral aperture 480 to seal the internal lumen 431. At least one cannula 484 providing an inner lumen 486 may penetrate the seal 482 and extend distally from the lateral aperture 480. In one variation, the cannula 484 extends distally to the distal probe tip 422. In another variation, the proximal portion of the probe neck 484 is configured as a distally-opening bell 486, with the lateral aperture 480 being disposed in the narrowing portion of the bell. In this variation, the probe sheath preferably seals (generally—the seal does not need to be complete or particularly efficient) against the probe neck 424. The cannula 484 may be used for suction or to inject materials such as dermal filler or irrigation fluids. The distal portion of the internal lumen 431, i.e., that portion distal from the seal 482, may be also be for suction or to inject materials such as dermal filler or irrigation fluids. In a preferred mode of operation, the cannula 484 is used for suction and the internal lumen is used for irrigation. The slots 472 or 474 described previously may present. In the preferred mode of operation, the slots 472 or 474 may serve as irrigation paths to establish a longitudinally-oriented 'flushing circuit' for tissue and tissue debris generated by ultrasonic operation of the probe tip 422 and probe neck 424.

In a method of using the expressions of the fourth embodiment, the distal probe tip 422 of the device is inserted beneath the surface of the skin 14. The probe tip 422 may be inserted through an existing perforation in the skin 14 (such as made by an applicator or obturator) or through a perforation made by a distal-most blade portion 423 of the probe tip 422. The ultrasound transducer 410 is powered to operate the probe tip 422. The distal end of the ultrasonically inactive probe sheath 430 is inserted beneath the surface of the skin 14. As the probe tip is advanced, the distal end of the probe sheath 430 is retracted to expose a greater length of at least probe tip 422. In one variation, the retraction of the distal end of the probe sheath 430 is caused by a longitudinal resistance to the advancement of the distal end of the probe sheath 430. In another variation, the user retracts the distal end of the probe sheath using an adjustment mechanism 460. In another variation, the distal end of the probe sheath 430 initially covers substantially all proximal portions of the probe tip 422, with retraction of the distal end of the probe sheath exposing proximal portions of the probe tip only after an initial penetration of the skin.

In an implementation of the method, a dermal filler 12 is injected into the facial feature 10. The dermal filler 12 may be injected before or after insertion of the probe tip 422 within the skin, depending upon the source of the dermal filler, e.g., separate applicator or injection through a fluid lumen of the end effector 420 (such as interstitial space 429 or internal lumen 431). The probe tip is used to shear-thin the dermal filler 12. In one variation of the implementation, the ultrasound transducer 410 is depowered and the dermal filler 12 is manipulated from the surface of the skin 14 while in a shear-thinned state. In another variation of the method, the ultrasound transducer 410 is depowered, and the probe tip 422 and probe sheath 430 withdrawn from the skin, whereupon the dermal filler 12 is manipulated from the surface of the skin 14 while in a shear-thinned state.

In another implementation of the method, the device is used to perform blepheroplasty. The distal probe tip 422 is inserted beneath the surface of the skin above a periorbital fat pad. Upon reaching the interior of the periorbital fat pad, the distal probe tip 422, and potentially a distal portion of the probe neck 424, may be manipulated within the periorbital fat pad while the ultrasound transducer 410 is powered to fluidize and shift or lyse and remove periorbital fat. The distal probe tip 422 may also be used to shear-thin a dermal filler 12 that has been injected into the periorbital fat pad in order to further shape the pad, or to inject a dermal filler 12 to take the place of previously removed fat. In a variation of the method, presented in the context of the present implementation, the distal end of the ultrasonically inactive probe sheath 430 is separable from the ultrasonic surgical instrument, e.g., by separating a frangible portion of the probe sheath 430 providing a perforated or scored periphery, or uncoupling coupling between distal and proximal portions of the probe sheath. The distal end of the probe sheath 430 is separated from the instrument (although still coaxially positioned on the instrument), whereupon the instrument is withdrawn while the separated distal end of the probe sheath remains in place beneath the surface of the skin. The separated distal end of the probe sheath 430 can thus function as an obturator, and the ultrasonic surgical instrument can later be reinserted through this obturator. Also, other surgical instruments, exploratory instruments, cannulae, and the like can be inserted through this obturator as part of a greater surgical procedure. The separated distal end of the probe sheath is, of course, eventually withdrawn from beneath the skin to complete that stage of the overall surgical procedure.

The expressions of the third and fourth embodiments advantageously shear-thin dermal fillers to make injection procedures more precise while simultaneously enabling the use of highly molecular weight, high longevity biomaterials. The same ultrasound end effector may be used to inject dermal fillers and to facilitate the bloodless dissection of tissue, as well as to create pockets for dermal filler and/or to remove unwanted tissue, such as fat. The end effectors 320 and 420 also may be used in vivo to thin previously injected filler so that it can be finger massaged to the desired location and thickness, as well as to remove excess filler if it has been inadvertently injected. If irrigation of a tissue pocket is desired, the same fluid lumen may be used for suction irrigation as for dermal filler injection and adjustment.

In a fifth embodiment of the invention, shown in FIGS. 33-64, the active portions of medical ultrasound handpiece assemblies 300 or 400 (and similar devices) and contact end effectors 320 or 420 (and similar devices) may be constructed from a single crystal or poly-crystalline resonating material, principally silicon, although germanium, diamond, and sapphire may also be used. Preferably, these structures are manufactured from a semiconductor wafer so as to be manufacturable using existing semiconductor processes. In addition, the transducer material may be a lead-free piezoelectric material, such as barium titanate, or a magnetostrictive material, such as nickel or "GALFENOL" (gallium-iron alloys marketed by ETREMA Products, Inc. of Ames, Iowa), so that the device may be both inexpensive enough to be employed as a single use device and suitable for disposal as ordinary medical waste, as opposed to lead-bearing hazardous waste. Other transducing materials, including ceramic PZT materials and electrostrictive materials as well as single crystal materials can also be used. PZT materials are lead-bearing, but have generally better peizoelectric performance. Electrostrictive materials are frequently lead-bearing, exhibit less hysteresis than piezoelectrics, have higher strain energy densities than piezoelectrics, and do not need to be poled; however electrostrictive martertials also have greater temperature sensitivity, require greater differential voltages, and require different modes of electrical control (since strain varies quadratically rather than linearly with respect to the applied voltage).

Figure 33:
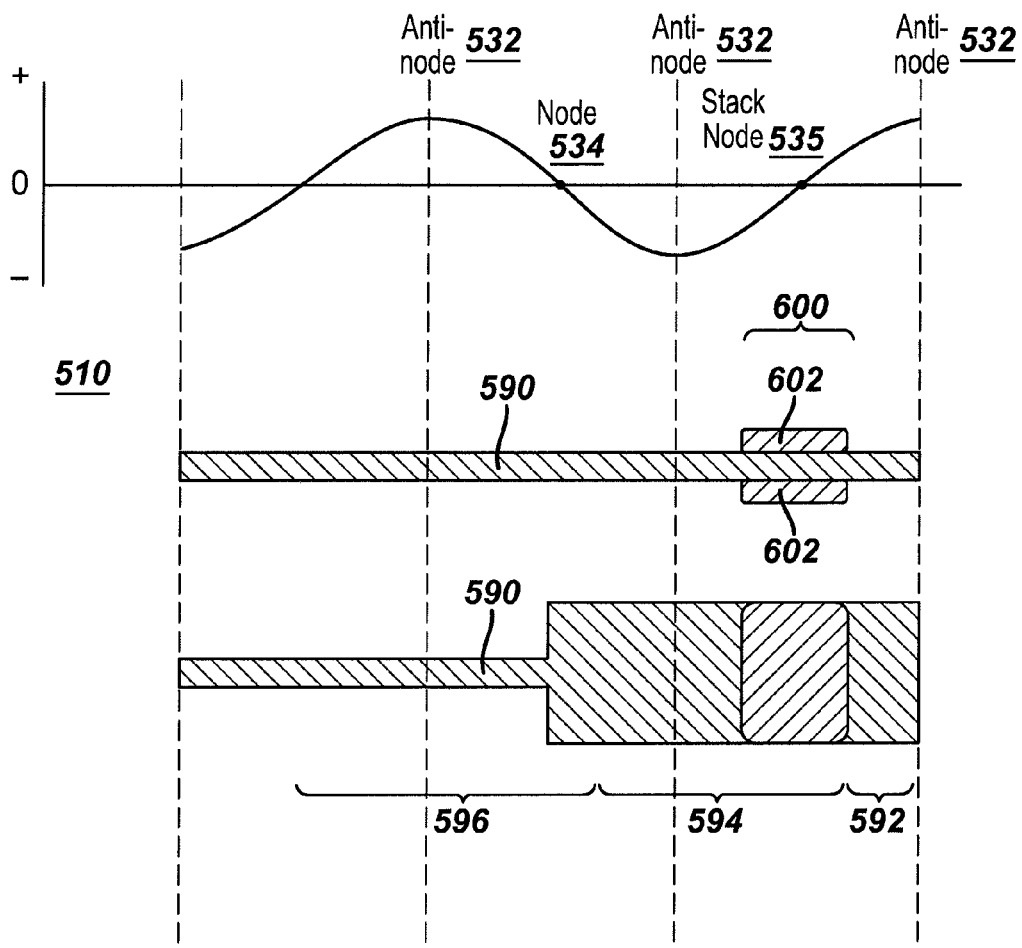
FIG. 33 is schematic view with side and edge views of an ultrasonic core.
Figure 34:
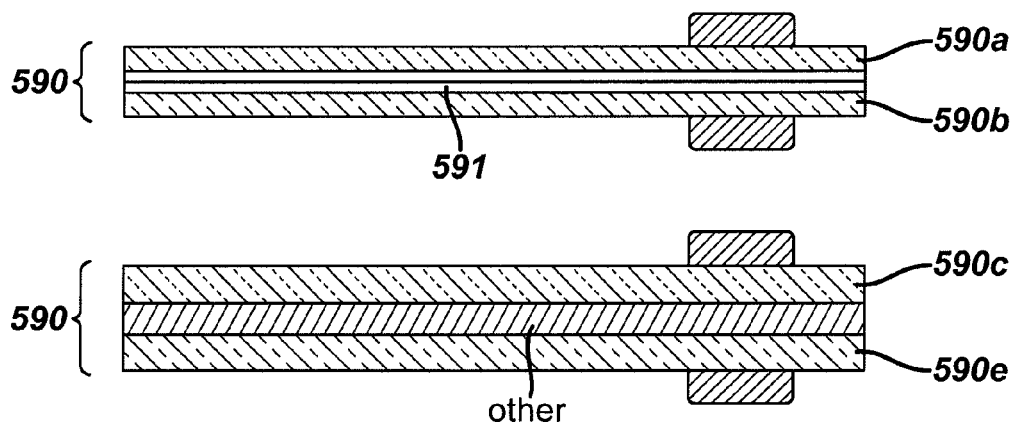
FIG. 34 is a schematic edge view of exemplary laminated ultrasonic core constructions.

The fifth embodiment, illustrated schematically in FIGS. 33 and 34, includes an ultrasonic core 510 for an ultrasound surgical apparatus including a longitudinally elongated, generally planar waveguide 590 constructed from a single crystal or polycrystalline material, and a transducing structure 600 affixed to the waveguide 590. The waveguide material is preferably silicon. For sake of clarity in the following discussion, the term "end" will be understood as referring to a longitudinal boundary, or a surface representing such a boundary; the term "edge" will be understood as referring to a lateral boundary, or surface representing such boundary, in a direction within the plane of the waveguide 590; and the term "side" will be understood as referring to a lateral boundary, or surface representing such a boundary, in a direction perpendicular to the plane of the waveguide 590.

Figure 35:
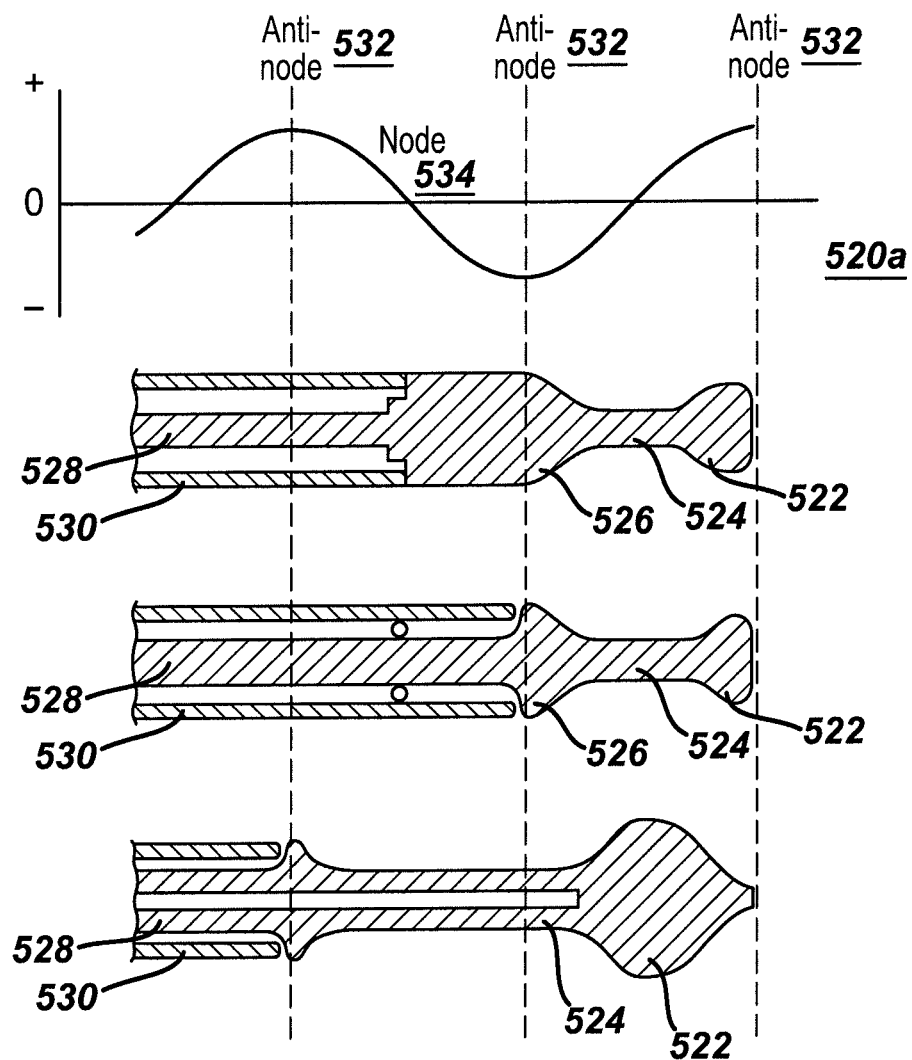
FIG. 35 is a cross-sectional side view of exemplary end effector portions.
Figure 36:
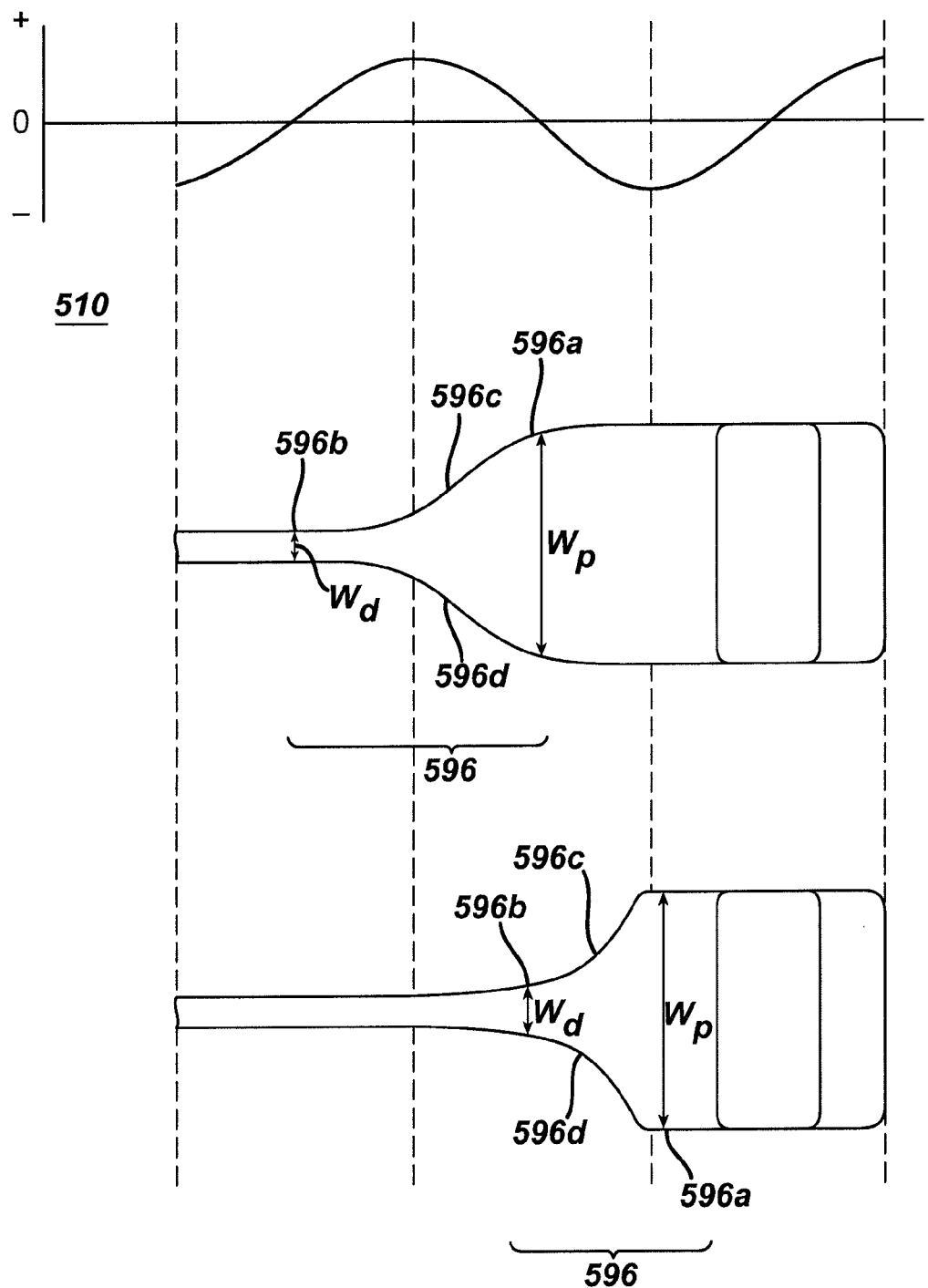
FIGS. 36 and 37 are schematic side views of exemplary second resonator configurations.

The waveguide 590 includes, in order, a first resonator or proximal end portion 592, a transduction portion 594, and a second resonator or distal end portion 596, as well as optional ancillary structures such as mounts or mount connections, intermediate gain stage structures, and the like which may be formed between components 592, 594, and 596. In one construction, the waveguide 590 is a monolithic structure. In another construction, shown in FIG. 34, the waveguide 590 is a laminated structure including a plurality of planar layers 590a, 590b, etc of the material. In one variation of the latter construction, two adjoining layers, e.g., 590a and 590b, may define a longitudinal channel, or other internal voids, which may serve, for example, as an internal lumen 591. In another variation of the latter construction, adjacent layers 590c and 590e may be separated by other materials, as further described below, in the laminated structure. The fifth embodiment may also include a single or polycrystalline material end effector portion 520a configured to serve at least as an ultrasonically active shaft 528. The end effector portion 520a preferably is configured to serve as a complete surgical probe (excepting ultrasonically inactive components such as the probe sheath 530); for example and as shown in FIG. 35, one having an ultrasonically active shaft 528, a probe dilation region 526 (if provided), a probe neck 524, and a distal probe tip 522. In one construction, the end effector portion 520a and the waveguide 590 (or a plurality of the layers thereof) are a monolithic structure, and thus monolithically coupled. Such a construction is suitable for precision microsurgical procedures such as dermatological procedures, dermal filler procedures like those described above, or neurological or hand surgeries. In another construction, the end effector portion 520a and the waveguide 590 are resonantly adjoining, i.e., resonantly connected at a node 534 for the transmission of a mode of vibration, and thus resonantly coupled. The various expressions and constructions of the fifth embodiment may be used as the active structures of the third or fourth embodiments, or may be combined with the various non-transducer structures described in those embodiments, or may be combined with other ultrasonic surgical instrument handpiece and/or end effector constructions known in the art.

Figure 37:
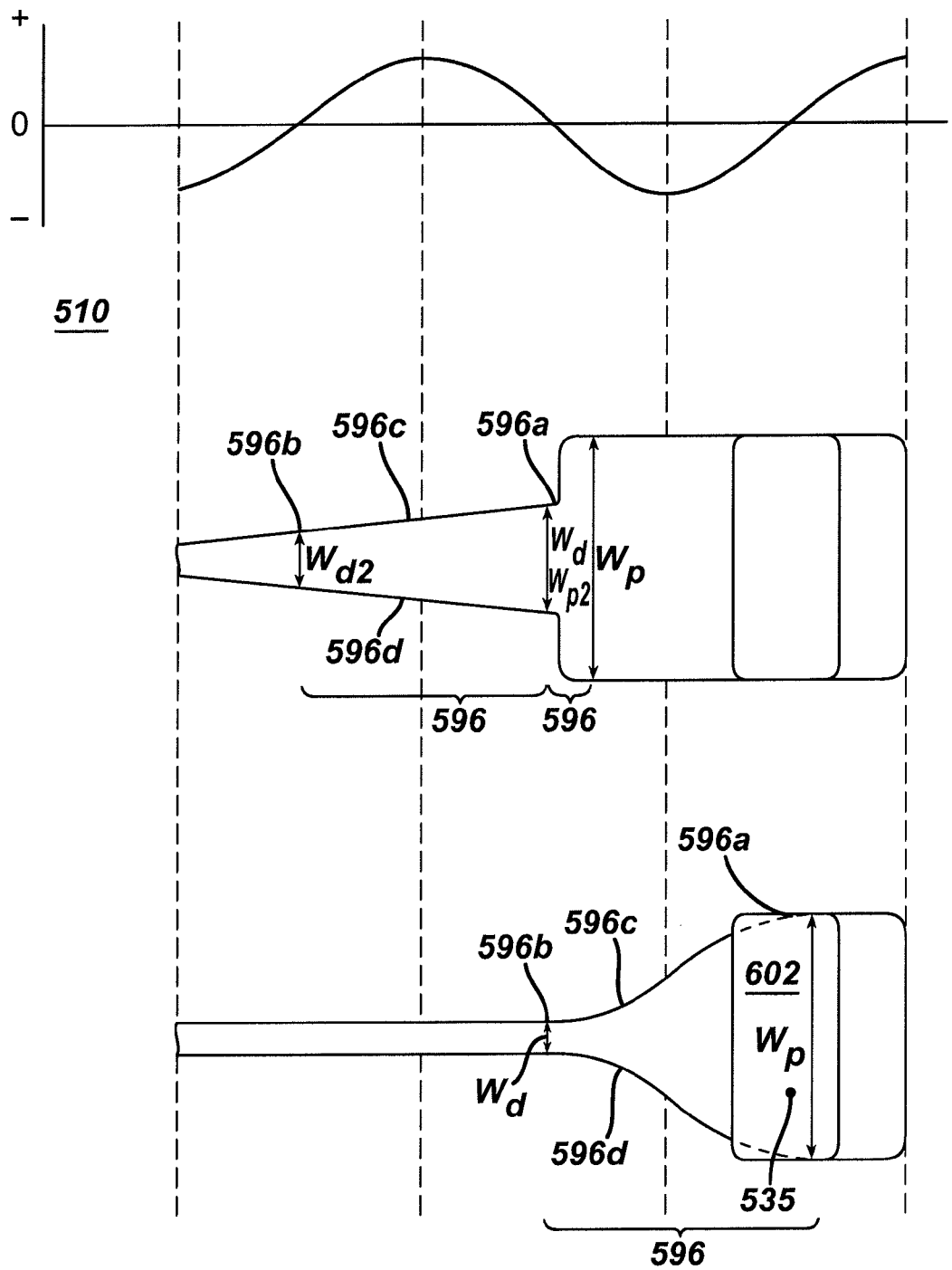

In a first expression of the fifth embodiment, shown in FIGS. 36-41, the second resonator 596 of waveguide 590 is configured to vary the magnitudes and/or modes of ultrasonic vibration created in the transduction portion 594 prior to transmission into an end effector portion 520a. The second resonator 596 includes a proximal end 596a having first transverse extent, e.g., a width $w_p$, a distal end 596b having a second, lesser transverse extent, e.g., a width $w_d$, and a body generally narrowing between the first and second transverse extents so as to create vibrational gain. In various constructions, the edges 596c and 596d of the second resonator 596 may be sinusoidally curved (FIG. 37 bottom), convexly or concavely curved (FIG. 36, top and bottom), constantly tapered (FIG. 37 top left), discontinuously stepped (FIG. 37 top right), or a shaped with a combination of any of the foregoing to vary the mode of ultrasonic vibration and, typically, to separate desirable modes of vibration from undesirable modes of vibration. As shown in FIG. 37, bottom instance, portions of a transducer 602 may extend over the proximal end 596a of the second resonator 596, which in a monolithic structure such as the present waveguide 590 is generally distinguished as a rapid change in geometry near a node 534, or (as in FIG. 37 bottom) a distal stack node 535.

Figure 38:
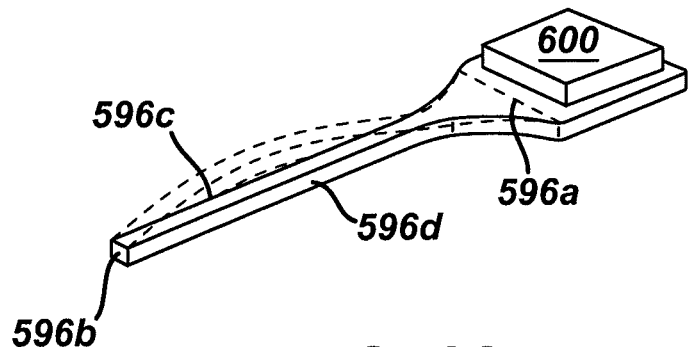
FIG. 38 is a perspective view of an exemplary second resonator configuration, with a resonant transverse mode of vibration shown in an exaggerated physical representation in phantom lines (top side only).
Figure 39:
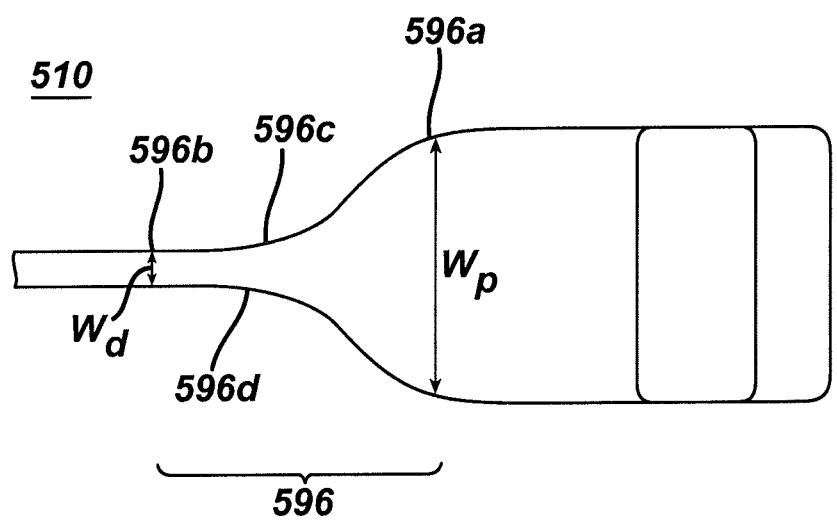
FIGS. 39 and 40 are schematic side views of exemplary second resonator configurations.
Figure 40:
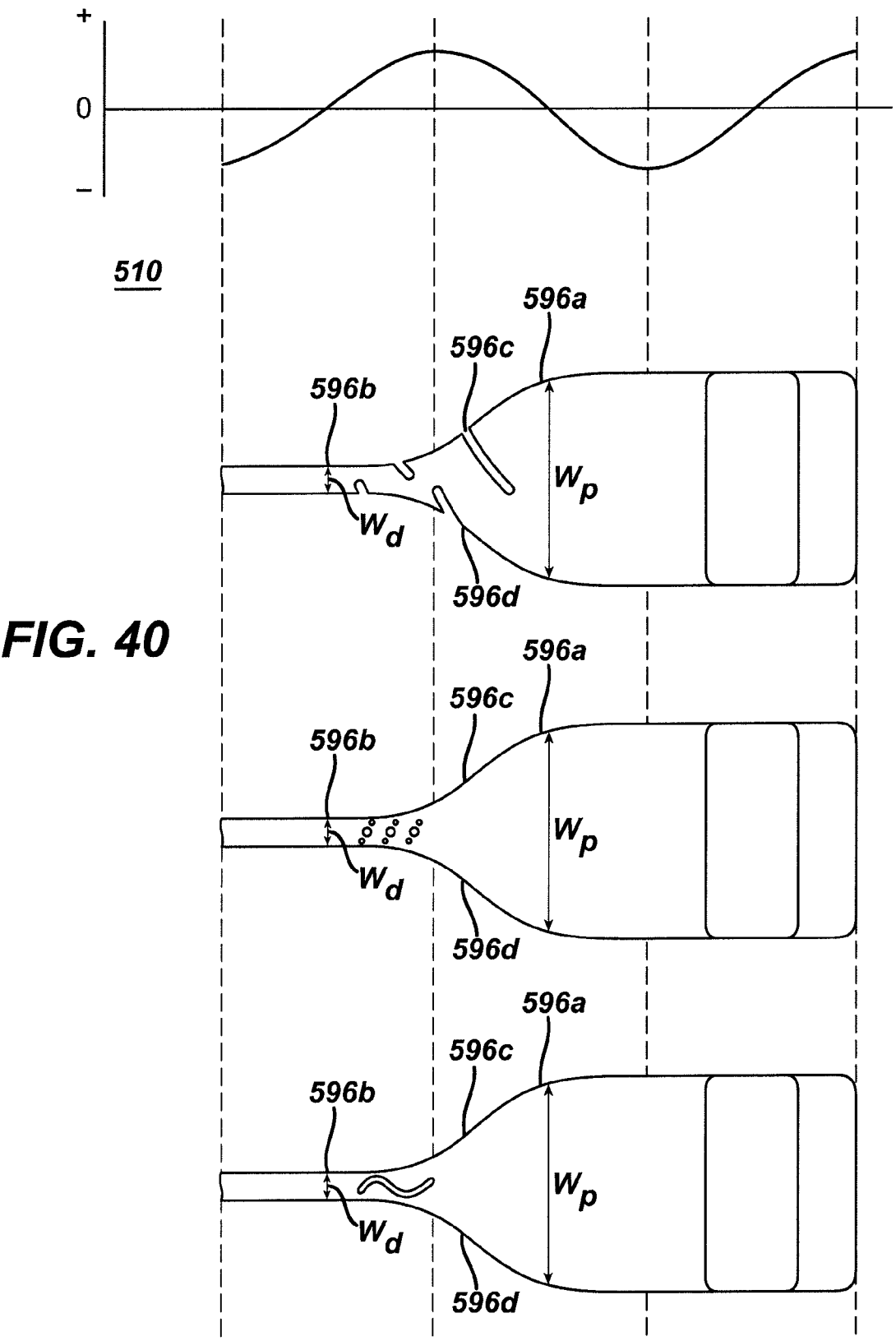

In a first construction of the first expression, shown in FIG. 38, the second resonator 596 is symmetric with respect to the central longitudinal axis of the waveguide 590 and has a substantial body portion with an essentially invariant transverse extent matching the second transverse extent of the distal end 596b. This symmetric and highly uniform construction can create a transverse mode of vibration at a subharmonic frequency, $\omega_n/N$ (where N=1, 2, 3, etc.), when transduction portion 594 is longitudinally vibrated at a primary frequency, $\omega_n$, due to autoparametric resonance. An end effector portion 520a coupled to the second resonator 596 may be configured to operate in a transverse working mode at a frequency equal to the subharmonic frequency, so that the mode of ultrasonic vibration is effectively transformed from a longitudinal driving mode at frequency $\omega_n$ to a transverse working mode at frequency $\omega_n/N$.

In a second construction of the first expression, the second resonator 596 is asymmetric with respect to the central longitudinal axis of the waveguide 590. In an exemplary construction, shown in FIG. 39, the edges of the second resonator are asymmetric with respect to the central longitudinal axis of the wave guide 590, with one edge 596c of the second resonator 596 being sinusoidally curved and the opposite edge 596d of the second resonator 596 being concavely curved. In other exemplary constructions, edges 596c and 596d may be shaped with one or more of the foregoing shapes, but are not identically shaped. These asymmetric constructions cause symmetric shear mode vibrations which create an additional transverse mode of vibration in proximal end 596a when transduction portion 594 is longitudinally vibrated. In another exemplary construction, shown FIG. 40, the body of the second resonator is rendered asymmetric with respect to the central longitudinal axis of the wave guide 590 by at least one aperture 597. The aperture 597 may be a slot extending partially longitudinally and partially laterally inwards from an edge 596c or 596d of the second resonator 596. In one modification (FIG. 40 middle) apertures 597 may be a staggered array of holes. In another modification (FIG. 40 bottom) the aperture 597 may be a longitudinally extending, sinusoidal slot. These asymmetric constructions cause the longitudinal resonant mode to couple into an additional torsional mode of vibration when transduction portion 594 is longitudinally vibrated.

Figure 41:
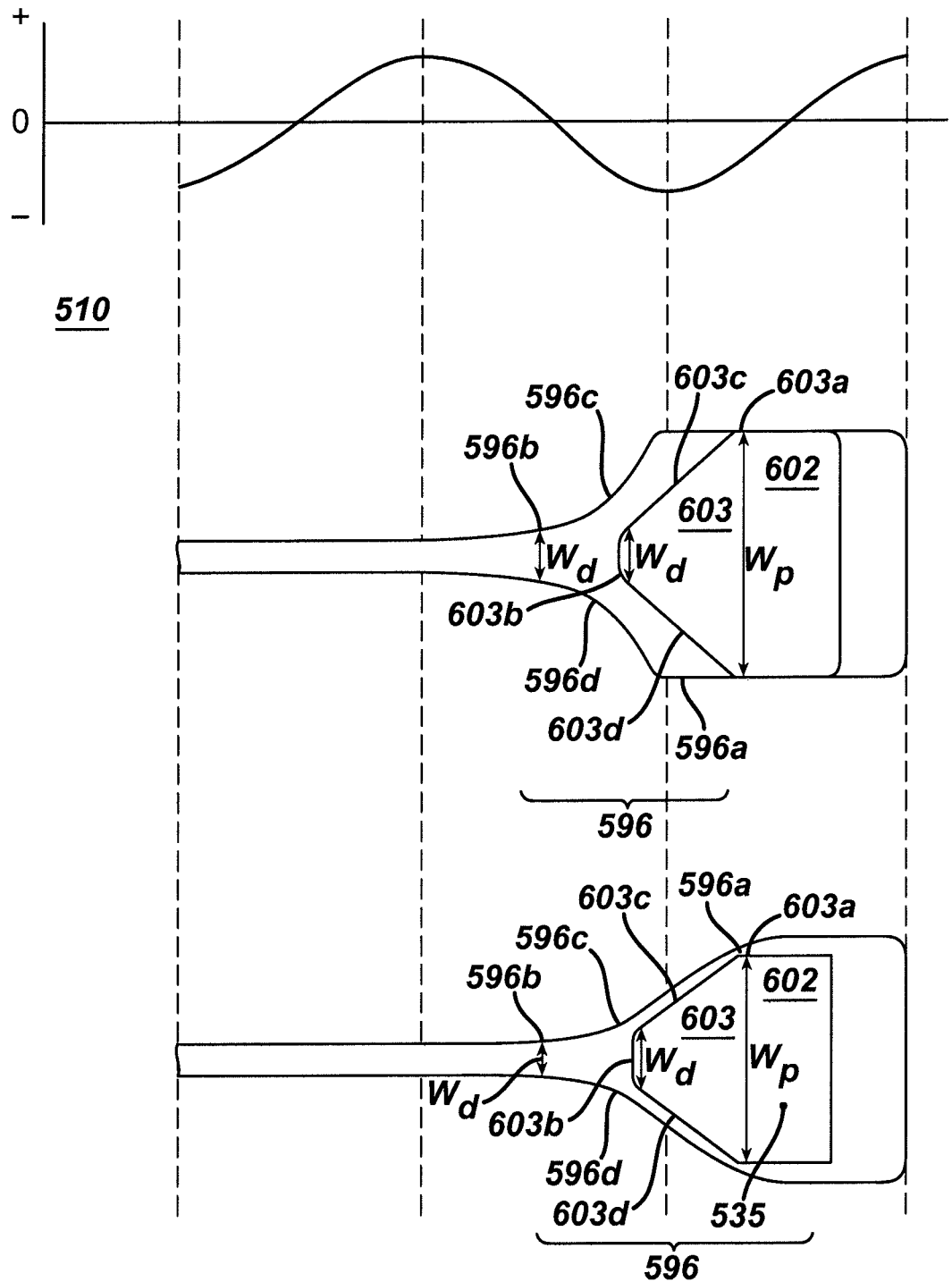
FIG. 41 is a schematic side view of exemplary second resonator configurations including a transducer gain portion.
Figure 42:
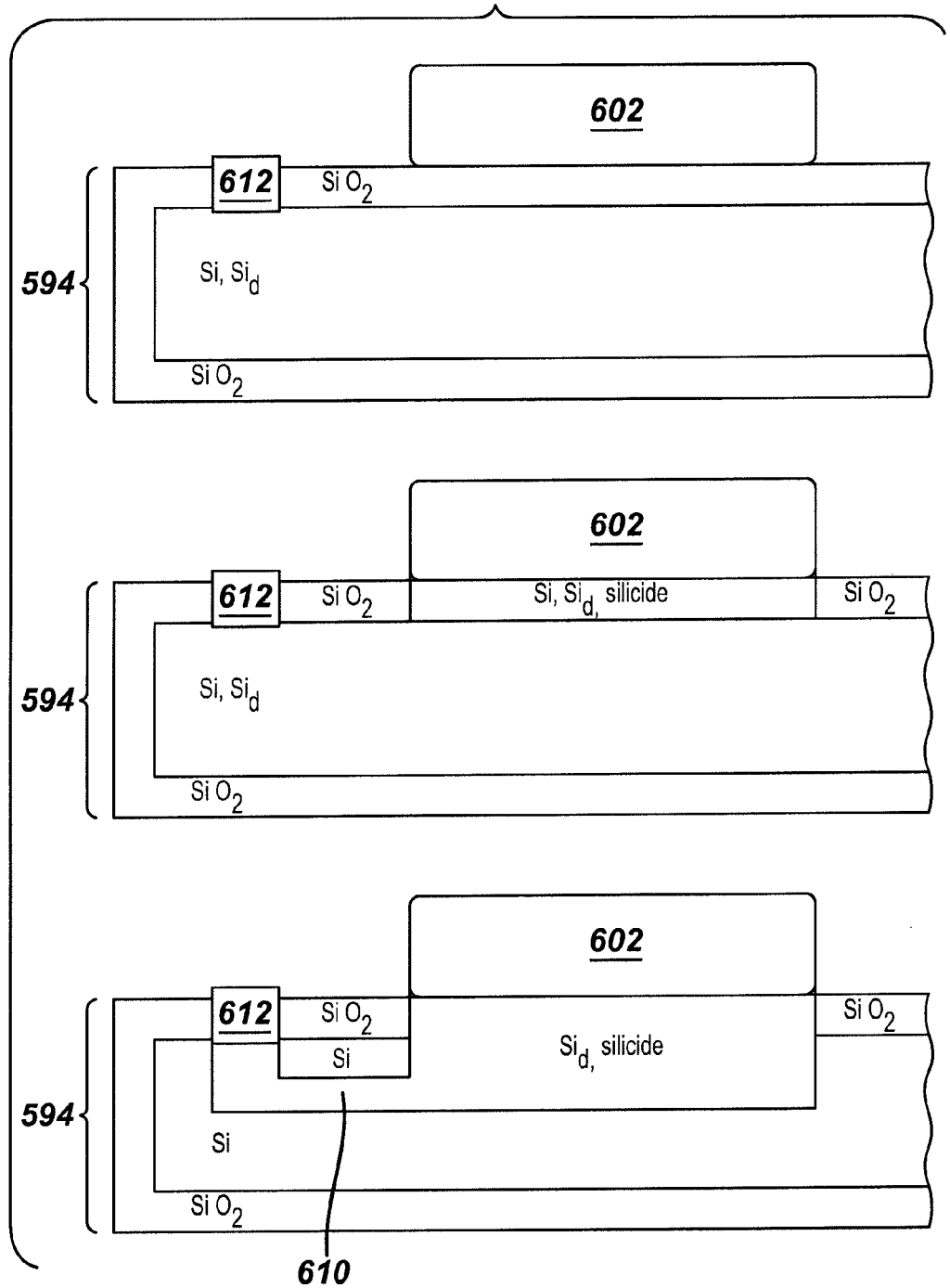
FIG. 42 is a schematic end view of exemplary transducer-to-waveguide bond and power structures.

In a third construction of the first expression, shown in FIG. 41, the second resonator 596 may include a gain portion 603 of a transducer 602 generally affixed to the adjoining transduction portion 594 of waveguide 590. The gain portion 603 may include a proximal end 603a having first transverse extent, e.g., a width $w_p$, a distal end 603b having a second, lesser transverse extent, e.g., a width $w_d$, and a body generally narrowing between the first and second transverse extents so as to create vibrational gain. In various constructions, the edges 603c and 603d of the gain portion 603 may be sinusoidally curved, convexly or concavely curved, constantly tapered, discontinuously stepped, or a shaped with a combination of any of the foregoing to vary the mode of ultrasonic vibration at the a distal end 596b of second resonator 596. The gain portion 603 may structured, affixed to the second resonator 596, and powered in essentially the same manners discussed below in the context of the transducer 602 and the transduction portion 594. The exposed side of the gain portion 603 may also be tapered from the proximal end 603a to the distal end 603b, i.e., the gain portion 603 may gradually reduce in thickness, as an additional means of increasing gain.

Figure 43:
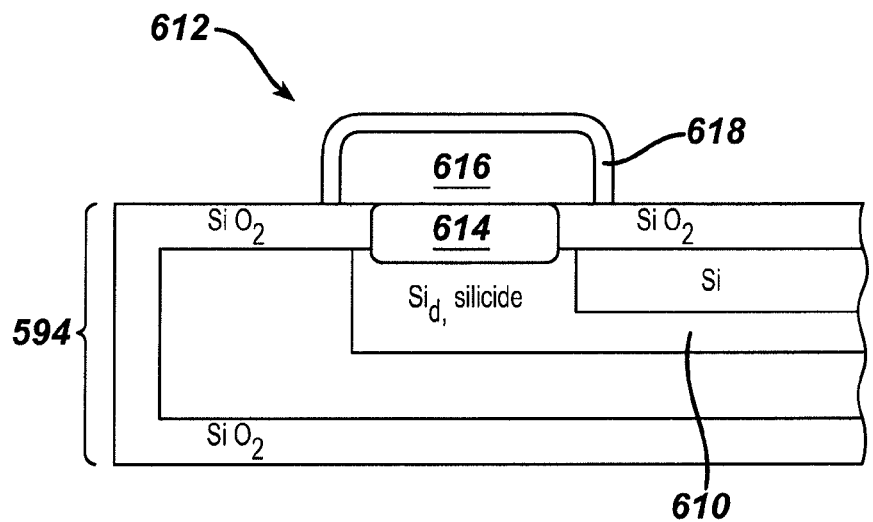
FIG. 43 is a schematic detail view of a waveguide electrical contact (Note: structure of transduction portion 594 is exemplary only).

In a second expression of the fifth embodiment, shown in FIGS. 42-53, at least one transducer 602 is affixed to a side of the transduction portion 594 of waveguide 590. In a first construction of the second expression, shown in FIG. 42, the transducer 602 is a piezoelectric or electrostrictive ceramic directly bonded to a side of the transduction portion 594. In a first variation of the first construction, the bonded surface of the transduction portion 594 may consist essentially of an oxygen rich surface layer, e.g., silicon dioxide ($SiO_2$), to insulate the transducer 602 from the transduction portion 594. In a second variation of the first construction, the bonded surface of the transduction portion 594 may consist essentially of elemental silicon (Si), elemental silicon containing a dopant ($Si_d$), or a silicide. The substrate of the transduction portion 594 in the second variation may consist essentially of elemental silicon or elemental silicon containing a dopant (i.e., bulk-doped silicon). Where the subsurface of the transduction portion 594 consists essentially of undoped elemental silicon, an embedded path 610 of silicon containing a dopant, or silicide, may be present to provide a preferential electrical path. Other surfaces of the waveguide 590 may be insulated by an oxygen rich surface layer formed on the waveguide 590 to prevent unintentional grounding. At least one electrical contact 612 may be provided on the waveguide, e.g., on an exposed surface of the transduction portion 594, proximate a node 534. An exemplary electrical contact 612, shown in cross section in FIG. 43, is a solder pad penetrating the oxygen rich surface layer (if present), in electrical contact with the subsurface of the transduction portion, and in electrical contact with the embedded path 610 (if present). In one exemplary construction, the electrical contact 612 includes an aluminum-copper alloy bonding layer 614, a nickel pad 616, and a gold top coat 618. A ground wire may be soldered to the electrical contact 612 to complete the ground path for the transducer 602.

Figure 44:
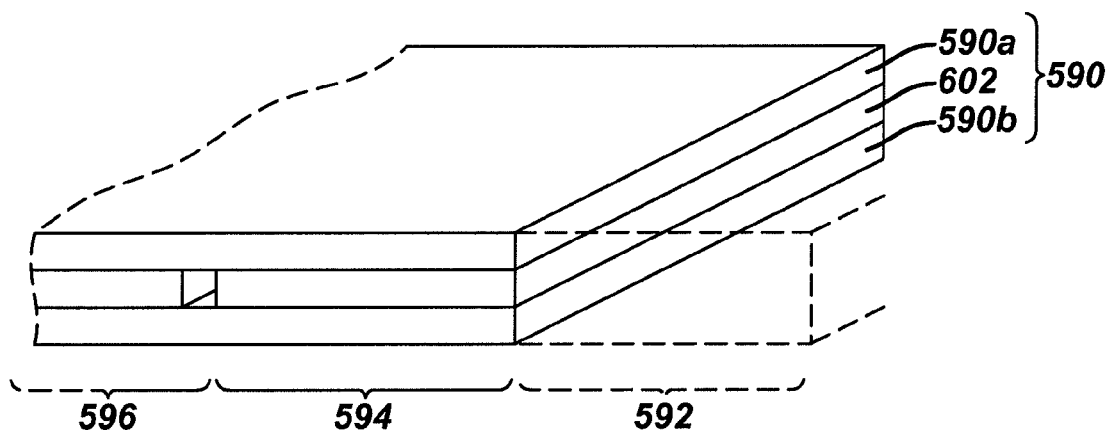
FIG. 44 is a schematic perspective view of a laminated waveguide with internal transducer. First resonator 592 is omitted but partially outlined in phantom lines for context.
Figure 45:
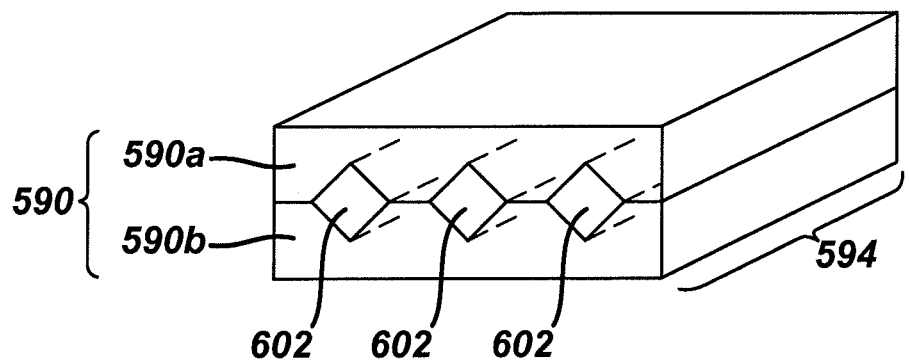
FIG. 45 is a schematic perspective view of a transduction portion, with first and second resonators omitted.

In a third variation of the first construction, shown in FIGS. 44 and 45, the transducer 602 is a piezoelectric or electrostrictive ceramic directly bonded on opposite sides to the transduction portions 594 of adjacent or adjoining layers 590a and 590b of a laminated waveguide 590. In a further variation, one layer may serve as an electrical source for the interstitially-disposed transducer 602 (when wired to an electrical source), and the other adjacent or adjoining layer may serve as an electrical ground (when wired to ground). In such a variation, the structure of the transduction portions 594 of both layers 590a and 590b may be the same as that described above, with an oxygen rich surface layer insulating adjoining portions, if any, of the transduction portions 594 of the layers. Alternately, the laminant between adjoining layers 590a and 590b may be an insulator. An exemplary laminant (not intended to be interpreted as "other materials" or to cause layers 590a and 590b to be considered adjacent rather than adjoining) is a silicon-to-silicon anodic bonding glass layer.

Figure 46:
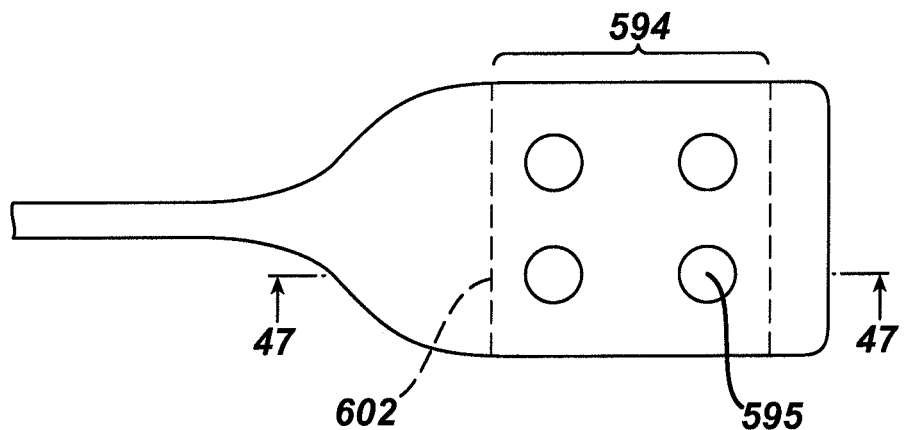
FIG. 46 is a side view of a transduction portion of a waveguide with the position of a transducer shown in phantom lines for context.
Figure 47:
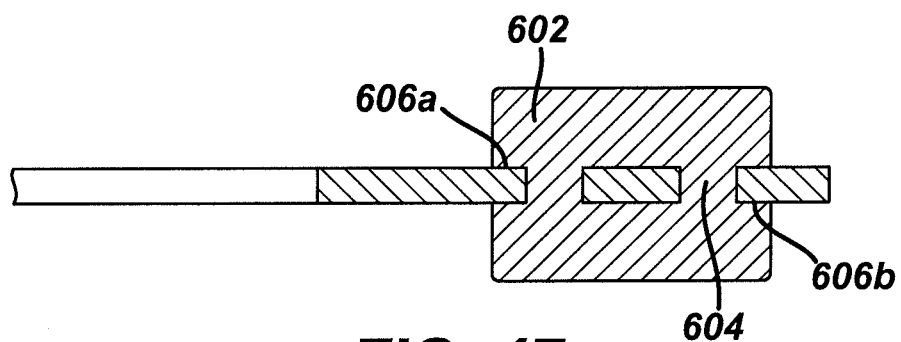
FIG. 47 is a cross-sectional edge view of the waveguide of FIG. 46.
Figure 48:
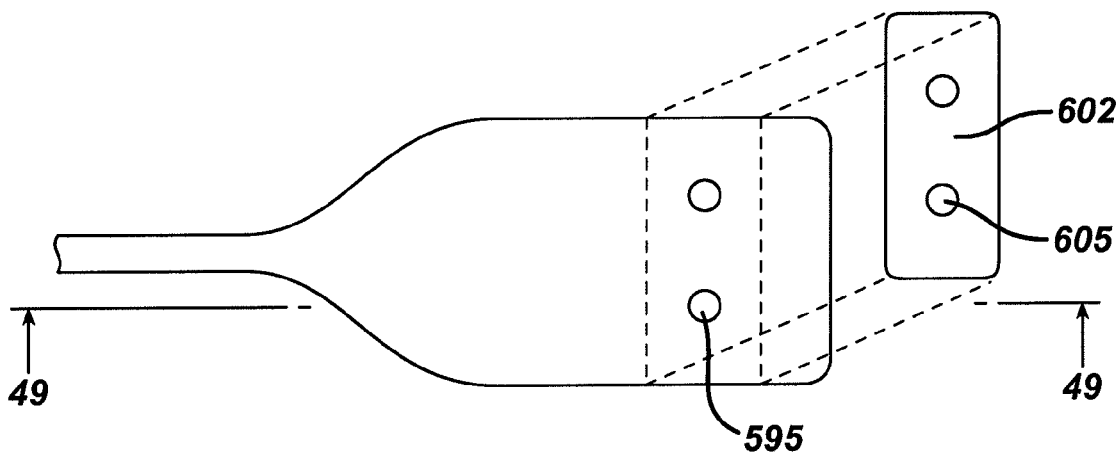
FIG. 48 is an exploded side view of a transduction portion of a waveguide.
Figure 49:
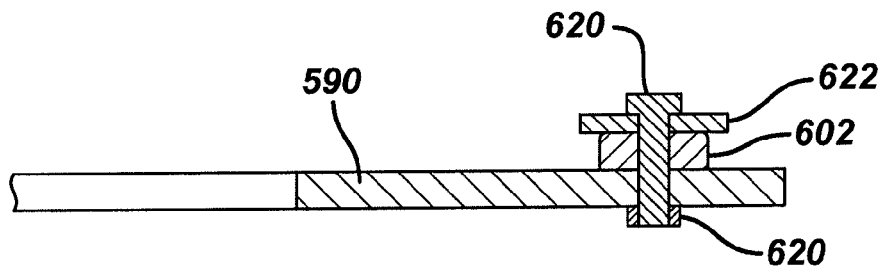
FIG. 49 is a cross-sectional edge view of the waveguide of FIG. 48, including a plate and compressive fastener.

In a fourth variation of the first construction, shown in FIGS. 46 and 47, the transducer 602 is a piezoelectric or electrostrictive ceramic directly bonded to both sides of the transduction portion 594. The transduction portion 594 includes at least one aperture 595 which is filled by a bridging portion 604 of a monolithic transducer 602. Abutment portions 606a and 606b of the transducer 602 abut the respective sides of the transduction portion 594 adjacent the at least one aperture 595. In addition to direct bonding of the transducer 602 with the transduction portion 594, mechanical abutment between the portions 604, 606a, 606b of the transducer 602 and the transduction portion 594 further affixes the transducer to the sides of the transduction portion 594. The transducer 602 may be formed in place by slip-forming and sintering the transducer material on the transduction section 594.

Figure 50:
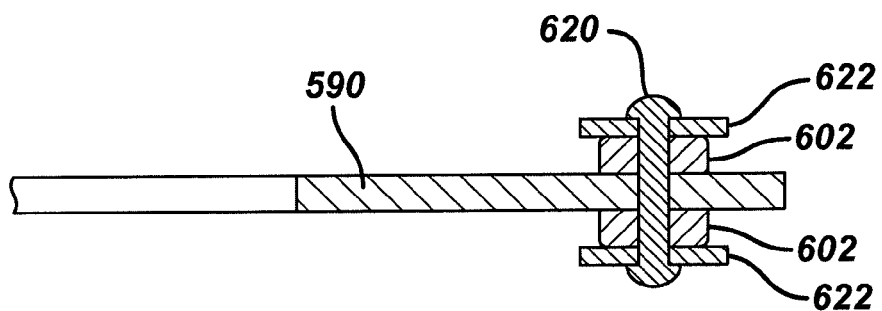
FIG. 50 is a cross-sectional edge view of a device similar to that shown in FIG. 48, but with a symmetrically disposed transducers, plates, and a compressive fastener.
Figure 51:
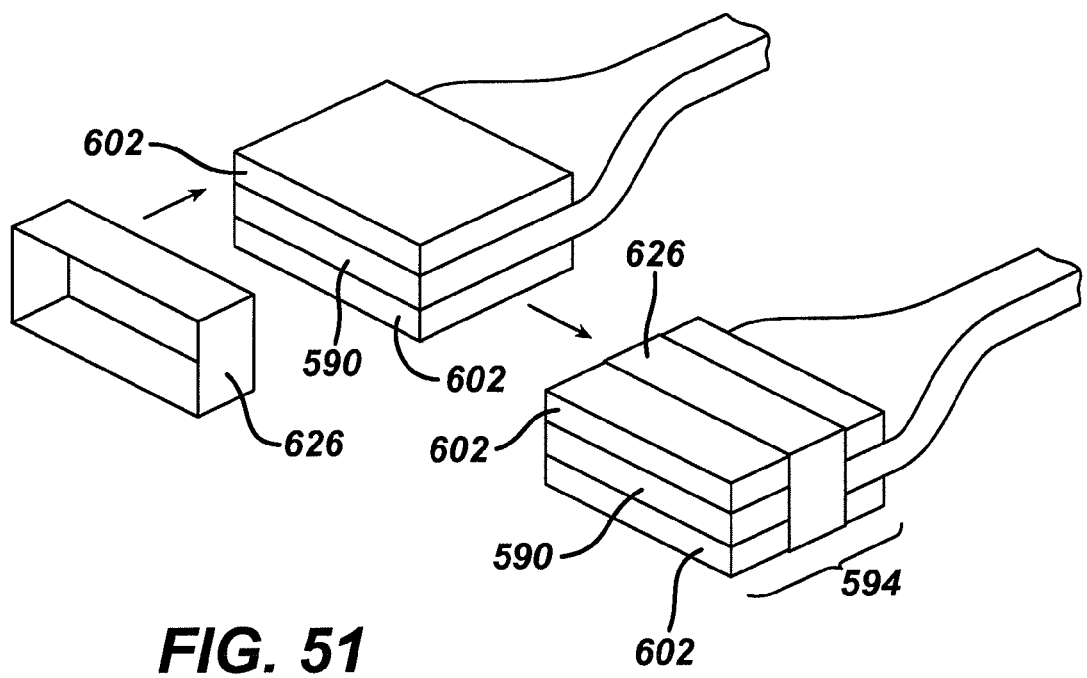
FIG. 51 is a perspective view of a transduction portion of a waveguide before and after the application of metal band.
Figure 52:
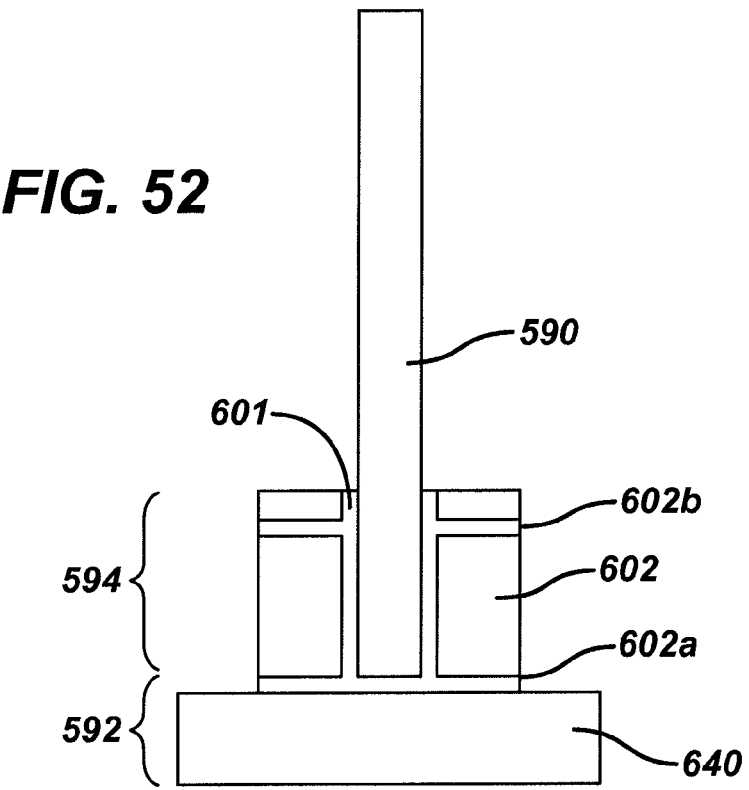
FIG. 52 is an edge view of a waveguide, with braze 601 exaggerated for visual clarity.

In a second construction of the second expression, the transducer 602 is clamped to a side of the transduction portion 594. This clamped construction is a simple mechanism for attachment, but also may be used to preload ceramic and single crystal transducers to increase power and displacement during shear mode operation of the transducer 602. In a first variation of the second construction, shown in FIGS. 48 and 49 the transduction portion 594 includes at least one aperture 595 and the transducer 602 includes at least one corresponding aperture 605. The aperture(s) 595 are preferably positioned at an anti-node 532. The corresponding apertures 595 and 605 are axially aligned and receive a compressive fastener 620, such as a bolt or rivet. In one modification, a plate 622 is disposed between an otherwise exposed side of the transducer 602 and the fastener 620 to distribute clamping forces over the transducer 602. In another modification (not specifically shown), a plate 624 is disposed between an otherwise exposed side of the transduction portion 594 and the fastener 620 to relieve local stress on the transduction portion 594 adjacent the aperture 595. As illustrated in FIG. 50, multiple transducers 602 and, if appropriate, multiple plates 622 may be clamped to the transduction portion 594 by the same compressive fastener 620. In a second variation of the second construction, shown in FIG. 51, a metal band 626 may be secured around the transduction portion 594 and transducer 602. The metal band is preferably heated, positioned, and allowed to cool to generate the clamping force. In one modification, a plate 622 is disposed between an otherwise exposed side of the transducer 602 and the metal band 626 to distribute clamping forces over the transducer 602. In another modification (not specifically shown), a plate 624 is disposed between an otherwise exposed side of the transduction portion 594 and the metal band 626 to relieve local stress on the transduction portion 594 under the metal band 626. As illustrated in FIG. 51, multiple transducers 602 and, if appropriate, multiple plates 622 may be clamped to the transduction portion 594 by the same metal band 626.

In a third construction of the second expression, the transducer 602 is indirectly bonded to the transduction portion 594 by an adhesive or braze 601. Exemplary adhesives are epoxies and cyanoacrylates, while exemplary brazes are set out in Table 1. In a first variation of the third construction, a proximal end 602a and a distal end 602b of the ultrasound transducer 602 are longitudinally compressed during bonding with the adhesive or braze 601. Once the adhesive has cured or the braze has cooled, the ultrasound transducer 602 remains residually compressed by the established bond between the transducer 602, the adhesive or braze 601, and the transduction portion 594. In a further variation, shown in FIG. 52, a distal end plate 628 may be similarly bonded to the waveguide 590, in an abutting relationship with the distal end 602b, to resist decompression of the transducer 602 at the exposed side and, during construction, to distribute compressive forces over distal end 602b of the transducer 602. The distal end plate 628 may conveniently be similarly bonded to the distal end 602b to form an integrally bonded assembly. In a yet further variation, also shown in FIG. 52, an end mass 640 may be similarly bonded to the first resonator or proximal end portion 592 of the waveguide 590, in an abutting relationship with the proximal end 602a, to resist decompression of the transducer 602 at the exposed side and, during construction, to distribute compressive forces over the proximal end 602a of the transducer 602. Where necessary or desirable, an adhesion layer may be applied to the bonding surfaces. The adhesion layer for an electrically conductive surface to be brazed with one of the compositions described herein may be prepared, for example, with a nickel plate and a gold top coat.

TABLE 1

Brazing Compositions and Temperatures

| Alloy composition | Melting range solidus | | Melting range liquidus | | Mushy range | |
|---|---|---|---|---|---|---|
| | °C. | °F. | °C. | °F. | °C. | °F. |
| 70 Sn/30 Pb | 183 | 361 | 193 | 380 | 10 | 19 |
| 63 Sn/37 Pb | 183 | 361 | 183 | 361 | 0 | 0 |
| 60 Sn/40 Pb | 183 | 361 | 190 | 375 | 7 | 14 |
| 50 Sn/50 Pb | 183 | 361 | 216 | 420 | 33 | 59 |
| 40 Sn/60 Pb | 183 | 361 | 238 | 460 | 55 | 99 |
| 30 Sn/70 Pb | 185 | 365 | 255 | 491 | 70 | 126 |
| 25 Sn/75 Pb | 183 | 361 | 266 | 511 | 83 | 150 |
| 10 Sn/90 Pb | 268 | 514 | 302 | 575 | 34 | 61 |

TABLE 1-continued

Brazing Compositions and Temperatures

| Alloy composition | Melting range solidus °C. | Melting range solidus °F. | Melting range liquidus °C. | Melting range liquidus °F. | Mushy range °C. | Mushy range °F. |
|---|---|---|---|---|---|---|
| 5Sn/95Pb | 308 | 586 | 312 | 594 | 4 | 8 |
| 62 Sn/36 Pb/2 Ag | 179 | 355 | 179 | 355 | 0 | 0 |
| 10 Sn/88 Pb/2 Ag | 268 | 514 | 290 | 554 | 22 | 40 |
| 5 Sn/95 Pb | 308 | 586 | 312 | 594 | 4 | 8 |
| 625 Sn/36 Pb/ 2.5 Ag | 179 | 355 | 179 | 355 | 0 | 0 |
| 10 Sn/88 Pb/ 2Ag | 268 | 514 | 290 | 554 | 22 | 40 |
| 5 Sn/90 Pb/ 5Ag | 292 | 558 | 292 | 558 | 0 | 0 |
| 5 Sn/92.5 Pb/ 2.5 Ag | 287 | 549 | 296 | 564 | 9 | 15 |
| 5 Sn/93.5 Pb/ 1.5 Ag | 296 | 564 | 301 | 574 | 5 | 10 |
| 2 Sn/95.5 Pb/ 2.5 Ag | 299 | 570 | 304 | 579 | 5 | 9 |
| lSn/97.5 Pb/ 1.5 Ag | 309 | 588 | 309 | 588 | 0 | 0 |
| 96.5 Sn/3.5Ag | 221 | 430 | 221 | 430 | 0 | 0 |
| 95 Sn/5 Sb | 235 | 455 | 240 | 464 | 5 | 9 |
| 42 Sn/58Bi | 138 | 281 | 138 | 281 | 0 | 0 |
| 43 Sn/43 Pb/14 Bi | 144 | 291 | 163 | 325 | 19 | 34 |
| 52 Sn/48 In | 118 | 244 | 131 | 268 | 13 | 24 |
| 70 In/30 Pb | 160 | 320 | 174 | 345 | 14 | 25 |
| 60 In/40 Pb | 174 | 345 | 185 | 365 | 11 | 20 |
| 70 Sn/18 Pb/ 12In | 162 | 324 | 162 | 324 | 0 | 0 |
| 90 Pb/5 In/5 Ag | 290 | 554 | 310 | 590 | 20 | 36 |
| 92.5 Pb/51 In/ 2.5 Ag | 300 | 572 | 310 | 590 | 10 | 18 |
| 97.5 Pb/2.5 Ag | 303 | 578 | 303 | 578 | 0 | 0 |

Source: Charles A. Harper, Electronic Packaging and Interconnection Handbook (4th Ed.), McGraw-Hill, 2004.

Figure 53:
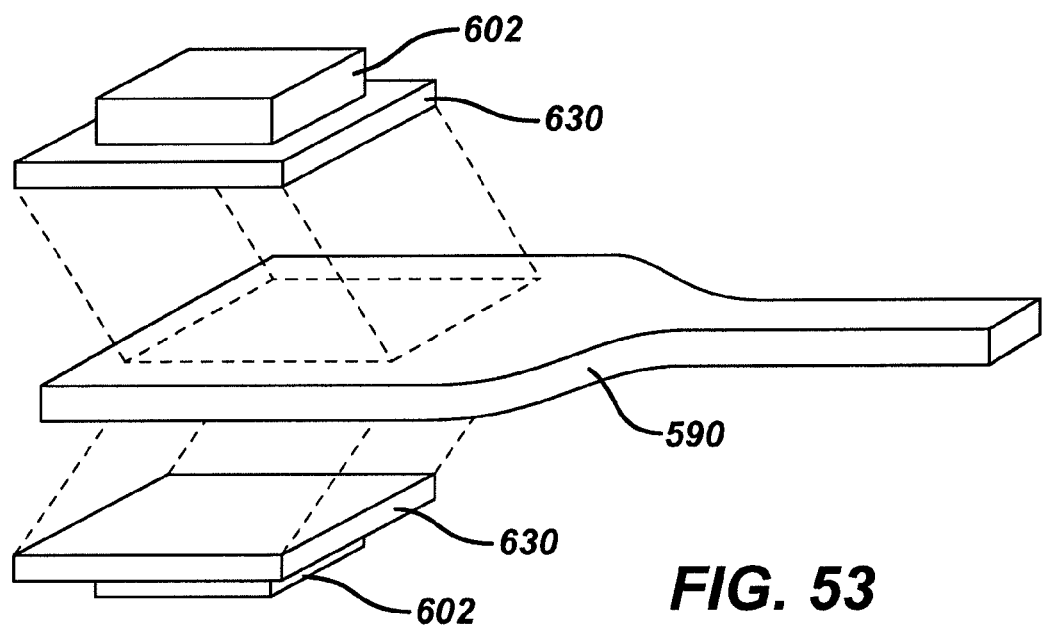
FIG. 53 is an exploded perspective view of a transduction portion of a waveguide.

In a second variation of the third construction, shown in FIG. 53, the transducer 602 is indirectly bonded to a carrier 630 by a braze 601, and the carrier 630 is bonded to the transduction portion 594 as a subassembly. The carrier 630 is preferably constructed from silicon, but other similarly temperature resistant substrates may be used. The carrier-transducer subassembly may advantageously be prepared separately from preparation of the waveguide 590, non-transducer structures such as the first resonator 592, the second resonator 596, and any end effector portion 520a. The carrier 630 may also be bonded to the transduction portion 594 with a low temperature process, permitting the emplacement of electrical contacts, e.g., electrical contact 612, prior to the attachment of the carrier-transducer subassembly to the transduction portion 524 and preventing the potential depoling of the transducers 602. This may be particularly advantageous if the transducer 602 would otherwise be bonded to silicon with a high temperature braze (solidus melting point of >275° C.). In a further variation, the carrier 630 is indirectly bonded to the transduction portion 594 by a low temperature braze 601, such as the Sn—Bi and Sn—In alloys listed in Table 1. In another further variation, a silicon carrier 630 is laminated to the transduction portion 594 by silicon-glass-silicon anodic bonding. Silicon dioxide layers can be grown on the silicon carrier 630 and transduction portion 594, and a glass layer can be sputtered or deposited by a sol-gel process on one of the silicon dioxide layers, followed by assembly and bonding using a DC voltage applied across the assembly, resulting in covalent bonding between the silicon dioxide and glass layers.

Figure 54:
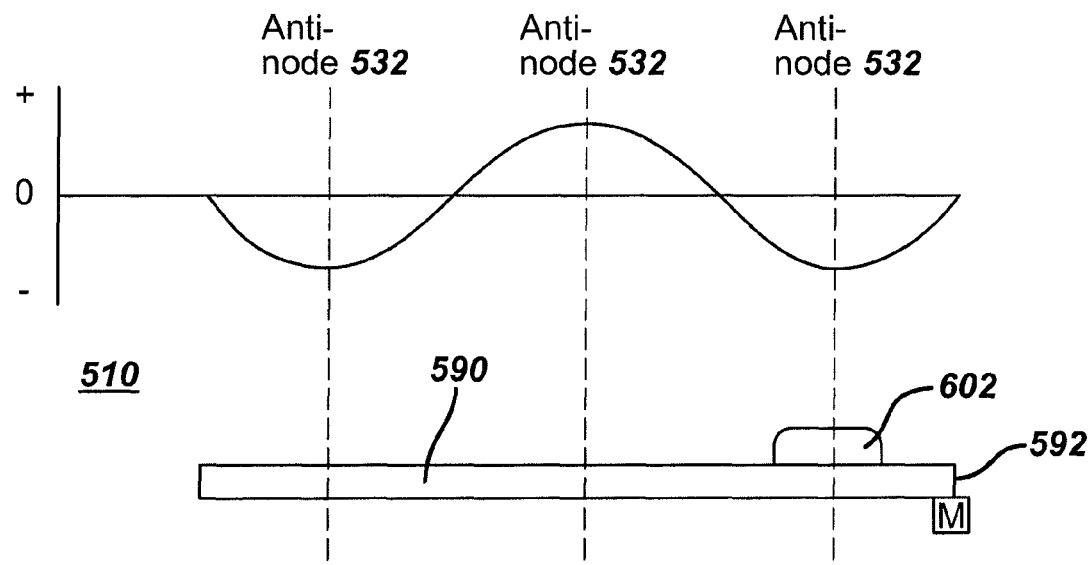
FIGS. 54 and 55 are schematic edge views of ultrasonic core transducer structures.
Figure 55:
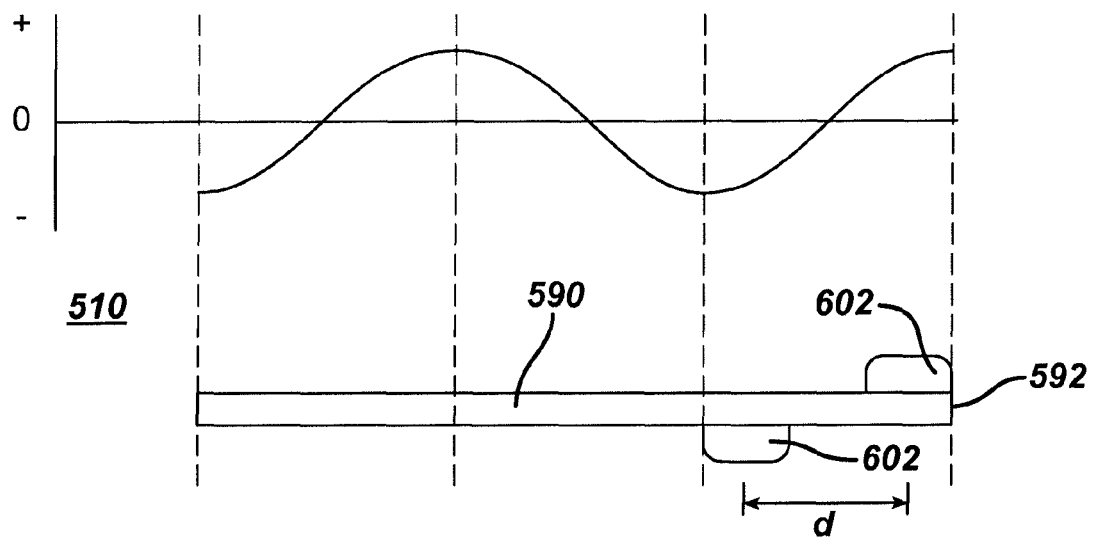
Figure 56:
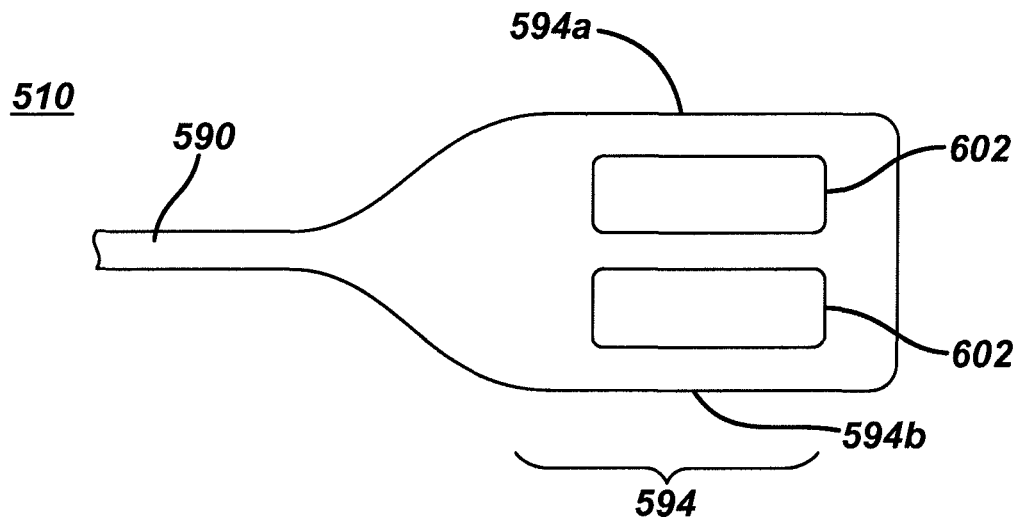
FIG. 56 is a schematic side view of an ultrasound core transducer structure.

In a fourth construction of the second expression, shown in FIGS. 54-56, at least one transducer 602 is affixed to the transduction portion 594 of waveguide 590 and configured to create a transverse mode of vibration. In a first variation of the fourth construction, shown in FIG. 54, a transducer 602 is affixed to an exposed side of the transduction portion 594, and configured to operate in a transverse resonant mode perpendicular to the plane of the waveguide 590. No transducer is affixed to the opposite exposed side of the transduction portion 594. A proximal portion of the transduction portion 594 is fixed against vibration, e.g., by a handpiece mount M, at a longitudinal distance, d, from the center of mass of the transducer 602. Operation of the transducer 602 creates an antinode 532 at the center of mass of the transducer 602, and a transverse mode of vibration out of the plane of the waveguide 590. Variation of the longitudinal distance d will vary the frequency of the resonant mode of vibration, i.e., the wavelength of the standing wave. In a modification of the first construction, a large end mass 640 is affixed to the first resonator or proximal end portion 592 to create a virtual node 534 due to the resistance of the large rest mass to displacement. Varying the longitudinal separation of the centers of mass of the transducer 602 and the end mass 640 will vary the frequency of the resonant mode of vibration.

In a second variation of the fourth construction, shown in FIG. 55, a first transducer 602 is affixed to an exposed side of the transduction portion 594, and a second transducer 602 is affixed to an opposite exposed side of the transduction portion 594. The centers of mass of the first and second transducers 602 are separated by a longitudinal distance, d, and configured to operate in a transverse resonant mode perpendicular to the plane of the waveguide 590, with the first transducer 602 180 degrees out of phase with the second transducer 602. Operation of the transducers creates a transverse mode of vibration out of the plane of the waveguide 590, as well as a node between the first and second transducers at d/2. Variation of the longitudinal distance d will vary the frequency of the resonant mode of vibration, i.e., the wavelength of the standing wave, as well as the amplitude of the mode of vibration.

In a third variation of the fourth construction, shown in FIG. 56, a first transducer 602 is affixed adjacent one edge 594a of the transduction portion 594, and a second transducer 602 is affixed adjacent to the opposite edge 594b of the transduction portion 594, with the first and second transducers being separated by the central longitudinal axis of the waveguide 590. The first and second transducers 602 are configured to operate in a longitudinally-oriented shear mode where the first transducer 602 is 180 degrees out of phase with the second transducer 602. Operation of the transducers creates a primary transverse mode of vibration within the plane of the waveguide 590, and a secondary longitudinal mode of vibration.

In implementations of the second expression, the transducer 602 may be configured as a multi-element piezoelectric, electrostrictive, or, in come instances, magnetostrictive transducer stack. A multi-element transducer stack, in general, increases the power and amplitude of the modes of vibration created within the waveguide. A magnetostrictive transducer is preferably configured as a multi-element transducer stack to reduce eddy current losses during magnetic excitation. It is to be understood that references to an ultrasound transducer 602, with respect to the fifth embodiment in particular and to combinations with other embodiments or known devices generally, are intended to include both a transducer configured as a single element transducer and a transducer configured as a multi-element transducer.

Figure 57:
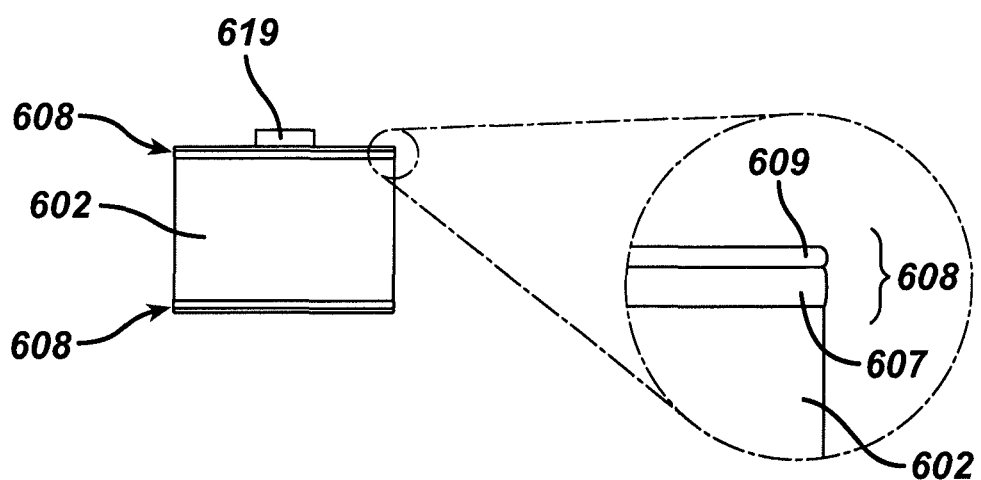
FIG. 57 is an edge view, with detail inset, of an ultrasound transducer electrode structure.

In a fifth construction of the second expression, the transduction portion 594 is configured to have at least one electrical contact 612 disposed on an exposed side of the transduction portion 594, and the transducer 602 is configured to have an electrode portion 608 for surface mount electrical connection to the electrical contact 612, with the electrode portion 608 electrically joined to the electrical contact 612 by a braze 601. The electrical contact 612 and transduction portion 594 may be configured as previously described, however in this construction the electrical contact may be disposed adjacent to or even under the transducer 602, which, rather than being directly bonded to the transduction portion 594, is indirectly bonded to the transduction portion through at least the electrode portion 608. The transducer 602 may also be bonded to the transduction portion 594 with an adhesive for mechanical stability. The electrode portion 608 may have a similar construction to that of the electrical contact 612, with, for example, a nickel pad 607 and a gold top coat 609. As shown in FIG. 57, the electrode 608 may be formed directly upon the transducer 602, and an electrical source such as a wire or shim 619 may soldered or brazed to an electrode 608 disposed on the exposed side of the transducer 602.

Figure 58:
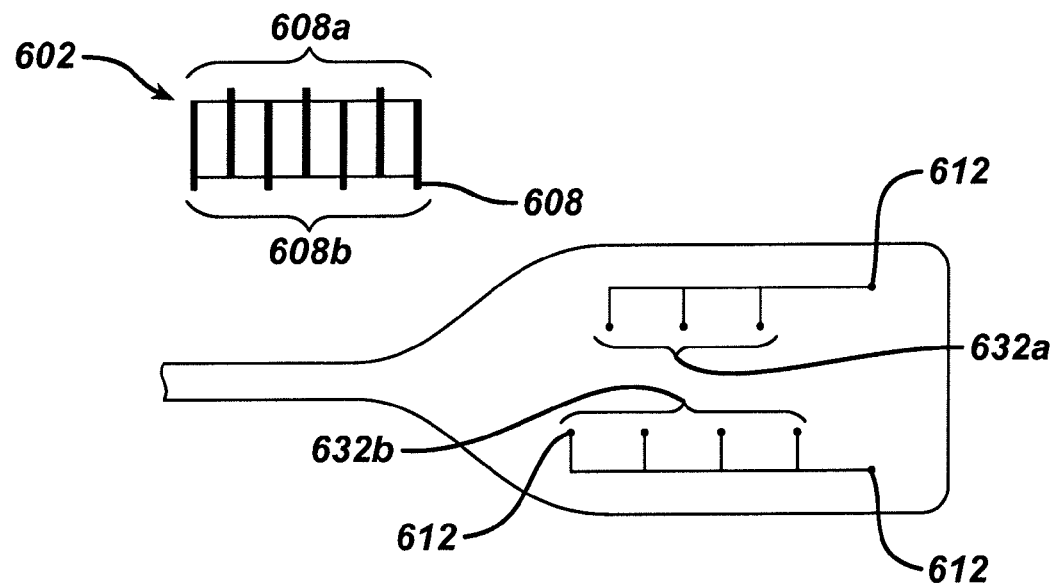
FIG. 58 is a schematic side view of an ultrasound transducer and waveguide configured for surface mount assembly.
Figure 59:
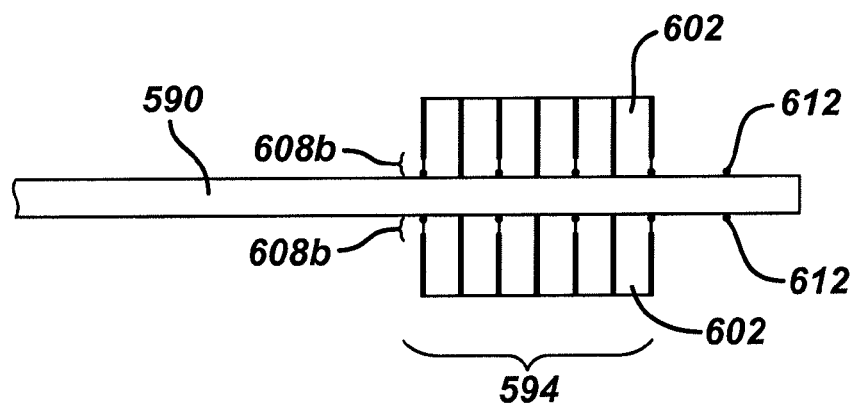
FIG. 59 is a schematic edge view of a waveguide with a surface mounted ultrasound transducer.
Figure 60:
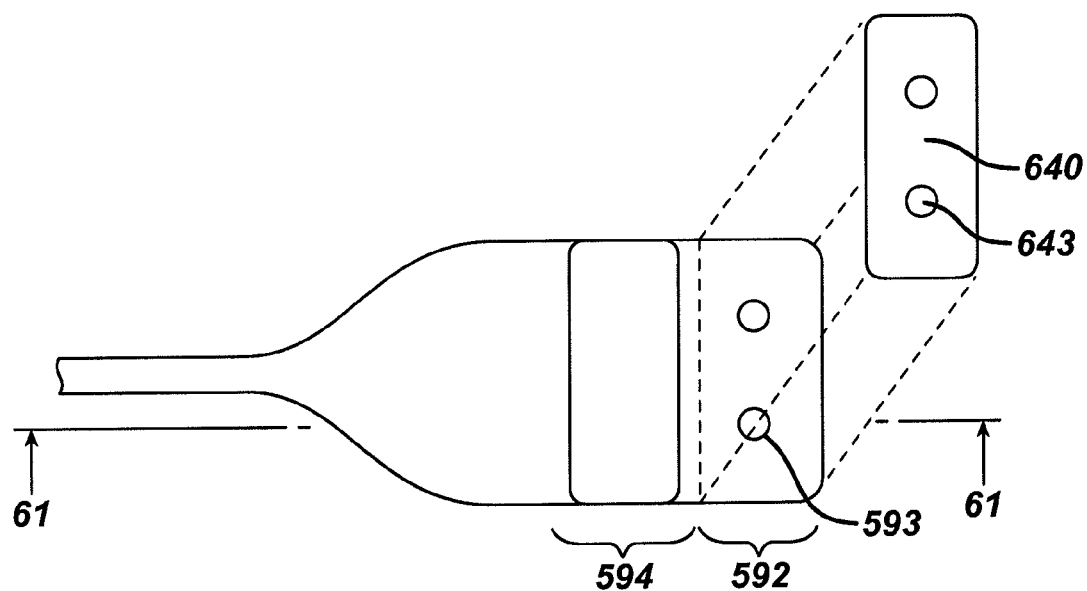
FIG. 60 is an exploded side view of a first resonator of a waveguide.

In a second variation of the fifth construction, shown in FIGS. 58 and 59, the transduction portion 594 is configured to have first 632a and second 632b generally linear arrays of electrical contacts 612 disposed on an exposed side of the transduction portion 594. The first array 632a is electrically connected to a remote electrical contact 612 which is electrically connectable to an electric source, and the second array 632b is electrically connected to a remote electrical contact 612 which is electrically connectable to ground. The electrical connections may be the embedded paths discussed above, or may be surface traces of a conductive material overlaying an oxygen rich surface layer, e.g., silicon dioxide ($SiO_2$). Such surface traces may be formed by screen printing techniques using materials such as DuPont 7723, a low temperature firing silver ink suitable for printing on glass. The transducer 602 is configured as a multi-element transducer stack having first 608a and second 608b generally linear arrays of electrode portions 608 extending from stack electrodes disposed between every element of the stack, with the first 608a and second 608b arrays being alternatingly connected to successive stack electrodes through the stack. The first 608a and second 608b arrays of the transducer 608 are configured for surface mount electrical connection to the first 632a and second 632b arrays of electrical contacts 612, respectively, with the individual electrode portions 608a and 608b electrically joined to corresponding individual electrical contacts 612 by a braze 601.

In other variations of the fifth construction, the transduction portion 594 may be configured to have a first plurality of source electrical contacts 632c and a second plurality of ground electrical contacts 632d, with both pluralities 632c and 632d disposed on an exposed side of the transduction portion 594. The first plurality 632c is electrically connected to an electric source, and the second plurality 632d is electrically connected to an electric ground. A multi-element transducer stack 602 is indirectly bonded to the transduction portion 594 at least through a first plurality of source electrical contacts 608c, electrically connected to the elements of the stack to supply power, and a second plurality of ground contacts 608d, electrically connected to the elements of the stack to provide ground, with the first plurality of source electrical contacts 608c of the transducer stack 602 conductively bonded to the first plurality of source electrical contacts 632c of the transduction portion 594, and the second plurality of ground electrical contacts 608d of the transducer stack 602 conductively bonded to the second plurality of ground electrical contacts 632d of the transduction portion 594. The first 608c and second 608d pluralities of contacts of the transducer stack may project from the transducer stack, may be disposed on the transducer stack, may be disposed on the transduction-portion-bonding surface of a carrier 630, or be a combination of any of the foregoing.

Figure 61:
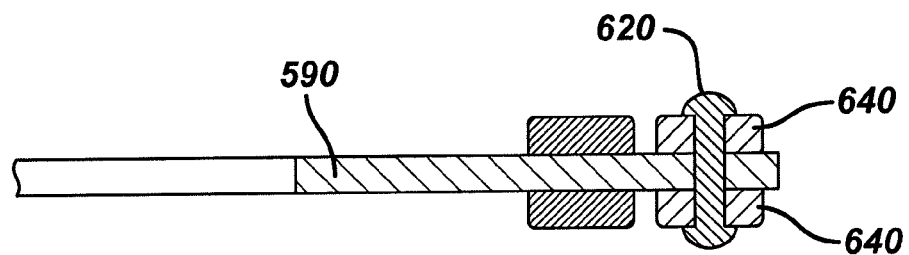
FIG. 61 is a cross-sectional edge view of the waveguide of FIG. 60, including a compressive fastener.

In a third expression of the fifth embodiment, shown in FIGS. 60-63, an end mass 640 is affixed to the first resonator 592. In a first construction of the third expression, shown in FIGS. 60 and 61, the first resonator 592 includes at least one aperture 593 and the end mass 640 includes at least one corresponding aperture 643. The corresponding apertures 593 and 643 are axially aligned and receive a compressive fastener 620, such as a bolt or rivet. As illustrated in FIG. 61, multiple end masses 640 may be affixed to the first resonator 592 by the same compressive fastener 620.

Figure 62:
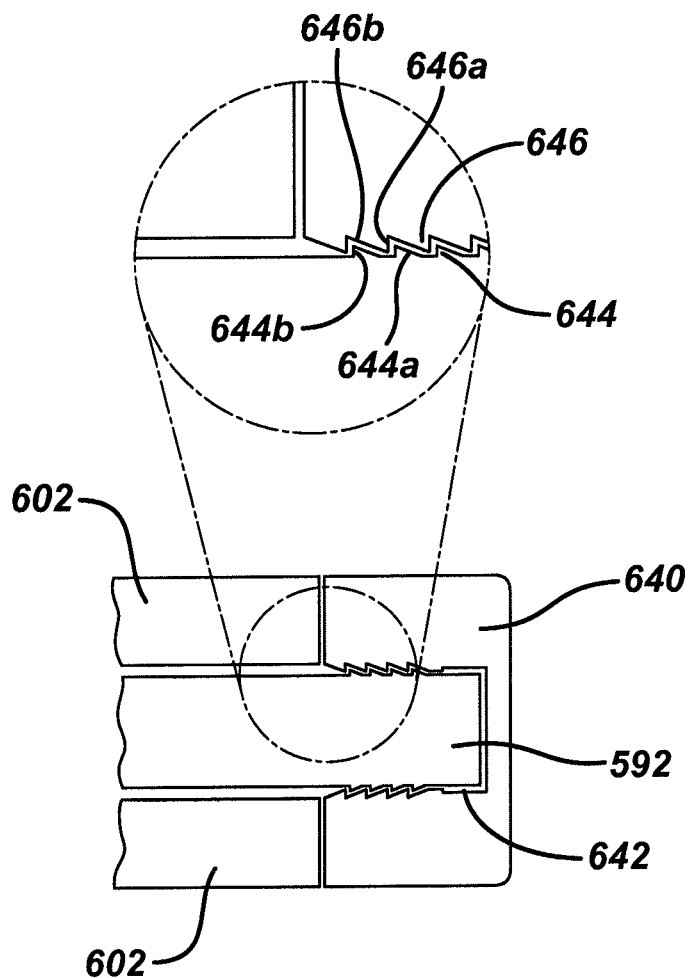
FIG. 62 is an edge view of a first resonator, with inset detail of a toothed connection.

In a second construction of the third expression, shown in FIG. 62, the sides of the first resonator 592 include teeth 644 with substantially inclined proximal surfaces 644a and substantially perpendicular distal surfaces 644b. The end mass 640 has a channel 642 configured to receive the first resonator 592 and teeth 646 with substantially vertical proximal surfaces 646a and correspondingly inclined distal surfaces 646b. Teeth 644 and 646 essentially irreversibly mesh when channel 642 receives first resonator 592. The second construction may be used to compress the transducers 602 as the transducers are formed, or to place pre-formed transducers under compression.

Figure 63:
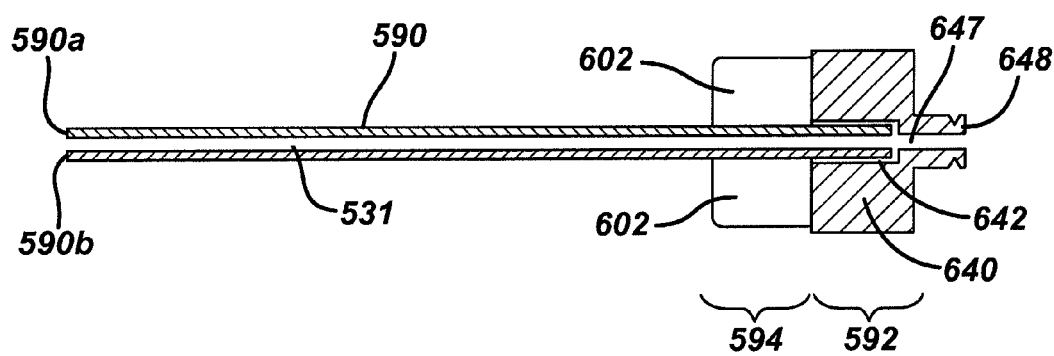
FIG. 63 is a cross-sectional edge view of a first resonator and end mass with interconnecting lumen.
Figure 64:
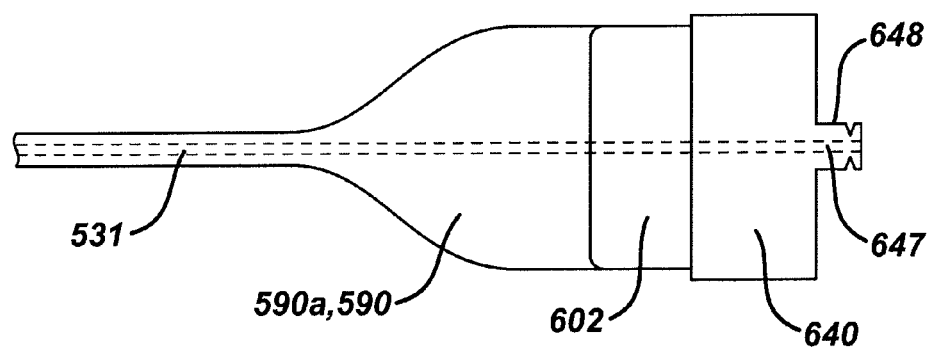
FIG. 64 is a schematic side view of the first resonator and end mass of FIG. 63, with the interconnecting lumen shown in phantom lines for context.

In a third construction of the third expression, shown in FIGS. 63 and 64, the end mass has a channel 642 configured to receive the first resonator 592. The end mass 640 is indirectly bonded to the first resonator 592 by an adhesive or braze 601. In a variation of the third construction, the first resonator 592 is a laminated structure having a lumen 531, for example, the top structure shown in FIG. 34, and the end mass has a correspondingly positioned lumen 647. The lumen 647 may communicate with a fitting 648, e.g., a leur fitting, on the proximal end of the end mass 640.

In implementations of the constructions of the third expression, the distal end of the end mass 640 may abut a transducer 602. Structures such as the aperture 593 of the first resonator 592 may be configured to require the end mass 640 to longitudinally compress the transducer 602. Structures such as the teeth 644 and 646 of the first resonator 592 and end mass 640 may mechanically lock the end mass 640 into longitudinal compression with the transducer 602. Finally, first resonator 592 and channel 642 of end mass 640 may be dimensioned such end mass 640 may be bonded to first resonator while end mass is longitudinally compressing the transducer 602. Once the adhesive has cured or the braze has cooled, the ultrasound transducer 602 remains residually compressed by the established bond between the first resonator 592 and the end mass 640.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

What is claimed is:

1. An ultrasonic surgical apparatus comprising:
 a medical ultrasound handpiece assembly having an ultrasound transducer; and
 an end effector coupled to the ultrasound transducer, the end effector having, in order, a distal probe tip, a probe neck, a probe dilation region, and an ultrasonically active shaft, with the shaft being coaxially held within an ultrasonically inactive probe sheath and conducting a standing ultrasonic wave between the ultrasound transducer and the distal probe tip;

wherein the probe dilation region is configured to have an average outside diameter that is equal to or greater than the average outside diameter of the probe tip and the average outside diameter of the probe neck;

wherein the probe sheath is configured to have an outside diameter that is approximately equal to the outside diameter of the probe dilation region, with the probe sheath and the probe dilation region forming an annular junction about the distal end of the ultrasonically active shaft; and wherein the probe dilation region is located proximate the first anti-node of the standing ultrasonic wave proximal from the distal probe tip.

2. The ultrasonic surgical apparatus of claim 1, wherein the annular junction is located at a node of the standing ultrasonic wave proximal from said first anti-node.

3. The ultrasonic surgical apparatus of claim 1, wherein the annular junction is located at said first anti-node.

4. An ultrasonic surgical apparatus comprising:
a medical ultrasound handpiece assembly having an ultrasound transducer; and
an end effector coupled to the ultrasound transducer, the end effector having, in order, a distal probe tip, a probe neck, a probe dilation region, and an ultrasonically active shaft, with the shaft being coaxially held within an ultrasonically inactive probe sheath and conducting a standing ultrasonic wave between the ultrasound transducer and the distal probe tip;
wherein the distal probe tip has an undulating periphery in transverse cross-section;
wherein the probe dilation region is configured to have an average outside diameter that is equal to or greater than the average outside diameter of the probe tip and the average outside diameter of the probe neck; and
wherein the probe sheath is configured to have an outside diameter that is approximately equal to the outside diameter of the probe dilation region, with the probe sheath and the probe dilation region forming an annular junction about the distal end of the ultrasonically active shaft.

5. The ultrasonic surgical apparatus of claim 4, wherein the distal probe tip has a high aspect ratio in transverse cross-section, with portions of the probe tip being wider than the width of the probe dilation region.

6. An ultrasonic surgical apparatus comprising:
a medical ultrasound handpiece assembly having an ultrasound transducer; and
an end effector coupled to the ultrasound transducer, the end effector having, in order, a distal probe tip, a probe neck, a probe dilation region, and an ultrasonically active shaft, with the shaft being coaxially held within an ultrasonically inactive probe sheath and conducting a standing ultrasonic wave between the ultrasound transducer and the distal probe tip;
wherein the probe dilation region is configured to have an average outside diameter that is equal to or greater than the average outside diameter of the probe tip and the average outside diameter of the probe neck;
wherein the probe neck has an undulating periphery in transverse cross-section; and
wherein the probe sheath is configured to have an outside diameter that is approximately equal to the outside diameter of the probe dilation region, with the probe sheath and the probe dilation region forming an annular junction about the distal end of the ultrasonically active shaft.

7. The ultrasonic surgical apparatus of claim 6, wherein a portion of the probe neck is configured to include a plurality of longitudinally extending, circumferentially arrayed slats with openings to an internal lumen.

8. The ultrasonic surgical apparatus of claim 6, wherein a proximal portion of the probe neck is configured as a solid rod defining a plurality of longitudinally extending, circumferentially arrayed ribs alternating with a plurality of longitudinally extending, circumferentially arrayed indentations.

9. An ultrasonic surgical apparatus comprising:
a medical ultrasound handpiece assembly having an ultrasound transducer; and
an end effector coupled to the ultrasound transducer, the end effector having, in order, a distal probe tip, a probe neck, a probe dilation region, and an ultrasonically active shaft, with the shaft being coaxially held within an ultrasonically inactive probe sheath and conducting a standing ultrasonic wave between the ultrasound transducer and the distal probe tip;
wherein the probe dilation region is configured to have an average outside diameter that is equal to or greater than the average outside diameter of the probe tip and the average outside diameter of the probe neck;
wherein the probe sheath is configured to have an outside diameter that is approximately equal to the outside diameter of the probe dilation region, with the probe sheath and the probe dilation region forming an annular junction about the distal end of the ultrasonically active shaft;
wherein the medical ultrasound handpiece assembly includes at least one fluid lumen in fluid communication with the end effector, and the ultrasonically active shaft includes an internal lumen, with the at least one fluid lumen of the medical ultrasound handpiece assembly in fluid communication with the internal lumen; and
wherein the ultrasonically active shaft projects from an internal fluid path within the ultrasound transducer; and wherein the at least one fluid lumen comprises an oppositely projecting portion of the ultrasonically active shaft which projects from a proximal end of the ultrasound transducer and within a handpiece port of the medical ultrasound handpiece assembly.

10. The ultrasonic surgical apparatus of claim 9, wherein the handpiece port is configured for connection to a syringe having a syringe tip, and the oppositely projecting portion is configured to project at least within the syringe tip and have a free end which does not contact the syringe and syringe tip.

* * * * *